(12) United States Patent
Kang et al.

(10) Patent No.: US 10,993,903 B2
(45) Date of Patent: May 4, 2021

(54) COVALENT TREATMENT WITH THIOLS OF KERATIN-CONTAINING MATERIALS

(71) Applicant: Living Proof, Inc., Boston, MA (US)

(72) Inventors: Soo-Young Kang, Boston, MA (US); Zhaoxia Ji, Boston, MA (US); Sara A. Johnson, Boston, MA (US); Dinara A. Villanueva, Boston, MA (US); Nawodi Abeyrathna, Boston, MA (US); Jeremiah A. Johnson, Boston, MA (US)

(73) Assignee: Living Proof, Inc., Boston, MA (US)

( * ) Notice: Subject to any disclaimer, the term of this patent is extended or adjusted under 35 U.S.C. 154(b) by 0 days.

(21) Appl. No.: 16/279,620

(22) Filed: Feb. 19, 2019

(65) Prior Publication Data

US 2019/0254955 A1   Aug. 22, 2019

Related U.S. Application Data

(60) Provisional application No. 62/632,947, filed on Feb. 20, 2018.

(51) Int. Cl.
*A61K 8/91* (2006.01)
*A61K 8/46* (2006.01)
(Continued)

(52) U.S. Cl.
CPC ............... *A61K 8/91* (2013.01); *A61K 8/22* (2013.01); *A61K 8/38* (2013.01); *A61K 8/46* (2013.01); *A61K 8/65* (2013.01); *A61Q 5/12* (2013.01); *A61K 2800/88* (2013.01); *A61K 2800/94* (2013.01); *A61K 2800/95* (2013.01);
(Continued)

(58) Field of Classification Search
CPC ....................................................... A61K 8/91
See application file for complete search history.

(56) References Cited

U.S. PATENT DOCUMENTS

| 3,242,052 A | 3/1966 | Sheffner |
| 3,768,490 A | 10/1973 | Kalopissis et al. |

(Continued)

OTHER PUBLICATIONS

International Search Report for International Application No. PCT/US2019/018581 dated Jul. 17, 2019.

*Primary Examiner* — Benjamin J Packard
(74) *Attorney, Agent, or Firm* — McCarter & English, LLP; Michael J. DeGrazia

(57) ABSTRACT

Disclosed are methods of preparing thiol keratin-containing materials, comprising applying a mixture comprising one or more thiol compounds and a catalyst. Methods of preparing cross-linked keratin-containing materials by applying a mixture comprising one or more thiol compounds and an oxidizing agent are also disclosed. Methods of grafting monomeric and polymeric materials on keratin-containing materials to provide a covalent coating on keratin-containing materials are disclosed. A mixture comprising one or more thiol compounds is applied to the keratin-containing material sample. The keratin-containing material sample then comprises a plurality of free thiol groups. A monomer is optionally applied to the keratin-containing material sample to form a plurality of covalent bonds between the free thiol groups and the monomers. The disclosed grafting methods can be carried out with or without catalyst.

13 Claims, 46 Drawing Sheets

(51) Int. Cl.
  *A61Q 5/12*   (2006.01)
  *A61K 8/22*   (2006.01)
  *A61K 8/38*   (2006.01)
  *A61K 8/65*   (2006.01)
  *C08F 2/48*   (2006.01)
  *C08F 20/18*  (2006.01)
  *C08F 22/40*  (2006.01)
(52) U.S. Cl.
  CPC ............... *C08F 2/48* (2013.01); *C08F 20/18* (2013.01); *C08F 22/40* (2013.01)

(56) References Cited

U.S. PATENT DOCUMENTS

| | | |
|---|---|---|
| 4,738,841 A | 4/1988 | Pigiet |
| 5,241,973 A | 9/1993 | Salce et al. |
| 2005/0002886 A1 | 1/2005 | Philippe et al. |
| 2007/0134185 A1 | 6/2007 | Samain et al. |
| 2011/0229430 A1 | 9/2011 | Hawkins et al. |
| 2016/0271151 A1* | 9/2016 | Sinko ............... A61K 47/34 |
| 2016/0346182 A1 | 12/2016 | Itaya et al. |

* cited by examiner

Figure 4

| Monomer | Structure |
|---|---|
| Pentaerythrityl tetrathiol | 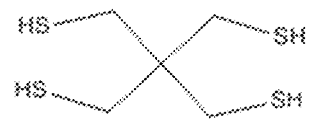 |
| Pentaerythritol tetrakis (3-mercaptopropionate) | 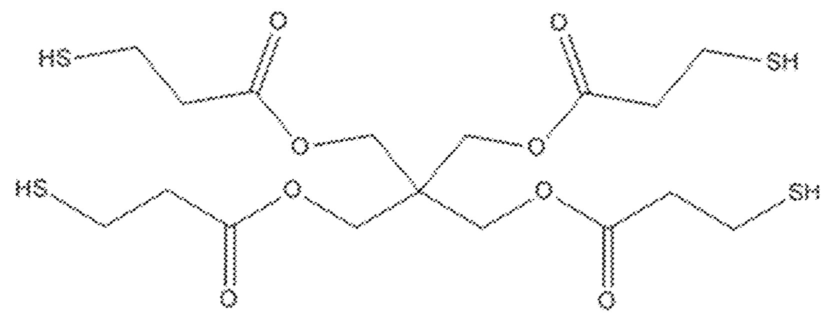 |
| 4-arm poly(ethylene glycol) thiol | 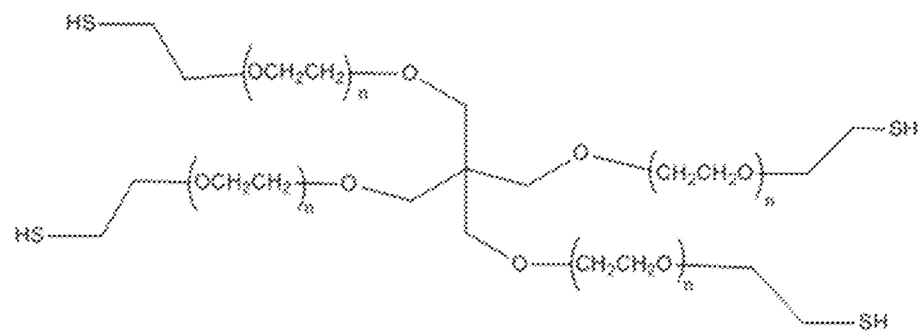 |

Initiation

Propagation (polar solvent)

|  | A | B | C |
|---|---|---|---|
| NALC, pH=2 | + | + | + |
| Rinse | - | + | - |
| Monomer, pH=9.5 | + | - | - |
| GLCA-NAG | + | + | + |
| Flat Iron | + | + | + |

After 15 Washes

COVALENT TREATMENT WITH THIOLS OF KERATIN-CONTAINING MATERIALS

RELATED APPLICATIONS

This application claims the benefit of priority to U.S. Provisional Patent Application Ser. No. 62/632,947, filed Feb. 20, 2018.

BACKGROUND

The human body includes a number of keratinous components, including hair, eyebrows, eyelashes, fingernails and toenails. These protein-based structures serve in various ways to enhance the body's functions—for example, hair helps protect the body from extreme temperatures, eyelashes and eyebrows stop debris from falling into the eyes, and fingernails provide a counterpressure to the fingertips that improve dexterity.

These keratinous substances consist primarily of the protein keratin, but in their virgin form also contain important small molecule components that improve functionality. For instance, fingernails and toenails function best (i.e. have optimal mechanical properties and flexibility) when they contain functional phospholipid molecules.[1] These molecules can be removed during normal wear and tear, and are particularly susceptible to harsh cleaning solvents. The consumer can partially mitigate this functional degradation through the use of moisturizers, but they must frequently spend time re-applying these products. A long-term method for achieving healthy, strong, virgin-like nails is still an unmet need.

Likewise, upon emerging from the follicle, mammalian hair is covered with a thin covalently bound lipid layer of 18-methyl eicosanoic acid (18-MEA) bonded to the outermost proteinaceous cell membrane layer (FIG. 1). The 18-MEA molecule is covalently attached to the outermost keratin layer of the cuticle via a thioester linkage, and lends the hair enhanced hydrophobicity and a conditioned, smooth feeling while acting as a boundary lubricant to decrease friction resistance.[2-6]

When hair is repeatedly weathered in response to stresses such as washing, drying, brushing, combing, rubbing, styling, and sun exposure, the 18-MEA layer is lost and the hair surface becomes more hydrophilic, negatively charged, and damaged-feeling. In addition, hair chemical services such as permanent waving (perming), straightening, relaxing, and smoothing all involve the cleavage of disulfide bonds to produce free thiol groups, i.e., hair reduction, as the first step. Although the reduction chemistry is well-known, strong reducing agents like ammonium thioglycolate (ATG) are typically used to achieve reduction throughout the entire hair fiber, which may cause extensive cuticle damage and hair fiber breakage. There are many products to address hair weathering and damage, including conditioners, leave-on creams, and smoothing oils. These products contain emollient and conditioning molecules such as natural oil derivatives, long-chain alcohols, carboxylic acids, and quaternary compounds, but, since the conditioning molecules in these products are deposited only on the surface of the hair via non-covalent interactions, they are routinely washed out of the hair and the effect is short-lived. Therefore, the consumer must frequently re-apply these products. A long-lived method for achieving healthy, strong, virgin-like hair is still an unmet need.

SUMMARY

In one aspect, the disclosure provides a method for treating a keratin-containing material, comprising:

i) providing a keratin-containing material sample comprising a plurality of disulfide bonds; and ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds.

In one aspect, the disclosure provides a method for treating a keratin-containing material, comprising:

i) providing a keratin-containing material sample comprising a plurality of disulfide bonds; and ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of functional groups.

In one aspect, the disclosure provides a method for treating a keratin-containing material, comprising:

i) providing a keratin-containing material sample comprising a plurality of disulfide bonds; and ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups.

In another aspect, the disclosure provides a method for treating a keratin-containing material, comprising:

i) providing a keratin-containing material sample comprising a plurality of disulfide bonds;

ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds; and iii) applying an oxidizing agent, thereby producing a cross-linked keratin-containing material sample, wherein the cross-linked keratin-containing material sample comprises a plurality of covalent bonds between the covalently bonded keratin-containing material sample and the thiol compounds.

In another aspect, the disclosure provides a method for treating a keratin-containing material, comprising:

i) providing a keratin-containing material sample comprising a plurality of disulfide bonds;

ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of functional groups; and iii) applying an oxidizing agent, thereby producing a cross-linked keratin-containing material sample, wherein the cross-linked keratin-containing material sample comprises a plurality of disulfide bonds between the keratin-containing material sample and the thiol compounds.

In another aspect, the disclosure provides a method for treating a keratin-containing material, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
  iii) applying an oxidizing agent, thereby producing a cross-linked keratin-containing material sample, wherein the cross-linked keratin-containing material sample comprises a plurality of disulfide bonds between the keratin-containing material sample and the thiol compounds.

In another aspect, the disclosure provides a method for treating a keratin-containing material, comprising:
  i) providing a keratin-containing material sample comprising a plurality of disulfide bonds;
  ii) applying to the keratin-containing material sample for a period of time a mixture, comprising one or more thiol compounds, thereby producing a covalently bonded keratin-containing material sample, wherein the covalently bonded keratin-containing material sample comprises a plurality of disulfide bonds between the keratin-containing material sample and the thiol compounds; and
  iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers.

In another aspect, the disclosure provides a method for treating a keratin-containing material, comprising:
  i) providing a keratin-containing material sample comprising a plurality of disulfide bonds;
  ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds; and
  iii) applying a monomer to the covalently bonded keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the covalently bonded keratin-containing material and the monomers.

In another aspect, the disclosure provides a method for treating a keratin-containing material, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
  iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers.

In another aspect, the disclosure provides a method for treating a keratin-containing material, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
  iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers.

In another aspect, the disclosure provides a method for treating a keratin-containing material, wherein a denaturation temperature of a keratin-containing material is improved, comprising:
  i) providing a keratin-containing material sample comprising a plurality of disulfide bonds; and
  ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds;
thereby improving the denaturation temperature of the keratin-containing material.

In another aspect, the disclosure provides a method for treating a keratin-containing material, wherein a denaturation temperature of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
  iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the denaturation temperature of the keratin-containing material.

In another aspect, the disclosure provides a method for treating a keratin-containing material, wherein a denaturation temperature of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups, thereby producing a thiol keratin-containing material sample, wherein the thiol keratin-containing material sample comprises a plurality of free thiol groups; and
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the denaturation temperature of the keratin-containing material.

In another aspect, the disclosure provides a method for treating keratin-containing material, wherein a denaturation temperature of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the denaturation temperature of the keratin-containing material.

In another aspect, the disclosure provides a method for treating a keratin-containing material, wherein a protein loss value of a keratin-containing material is improved, comprising:
i) providing a keratin-containing material sample comprising a plurality of disulfide bonds; and
ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds;

thereby improving the protein loss value of the keratin-containing material.

In another aspect, the disclosure provides a method for treating a keratin-containing material, wherein a protein loss value of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the protein loss value of the keratin-containing material.

In another aspect, the disclosure provides a method for treating a keratin-containing material, wherein a protein loss value of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups, thereby producing a thiol keratin-containing material sample, wherein the thiol keratin-containing material sample comprises a plurality of free thiol groups; and
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the protein loss value of the keratin-containing material.

In another aspect, the disclosure provides a method for treating a keratin-containing material, wherein a protein loss value of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the Young's modulus of the keratin-containing material.

In another aspect, the disclosure provides a method for treating a keratin-containing material, wherein an ultimate tensile strength of a keratin-containing material is improved, comprising:
  i) providing a keratin-containing material sample comprising a plurality of disulfide bonds; and
  ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds;

thereby improving the ultimate tensile strength of the keratin-containing material.

In another aspect, the disclosure provides a method for treating a keratin-containing material, wherein an ultimate tensile strength of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
  iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the ultimate tensile strength of the keratin-containing material.

In another aspect, the disclosure provides a method for treating a keratin-containing material, wherein an ultimate tensile strength of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least two free thiol groups, thereby producing a thiol keratin-containing material sample, wherein the thiol keratin-containing material sample comprises a plurality of free thiol groups; and
  iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the ultimate tensile strength of the keratin-containing material.

In another aspect, the disclosure provides a method for treating a keratin-containing material, wherein an ultimate tensile strength of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
  iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the ultimate tensile strength of the keratin-containing material.

In another aspect, the disclosure provides a method for treating a keratin-containing material, wherein hydrophobicity of a keratin-containing material is improved, comprising:
  i) providing a keratin-containing material sample comprising a plurality of disulfide bonds; and
  ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds;

thereby improving the hydrophobicity of the keratin-containing material.

In another aspect, the disclosure provides a method for treating a keratin-containing material, wherein hydrophobicity of a keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
  iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the hydrophobicity of the keratin-containing material.

In another aspect, the disclosure provides a method for treating a keratin-containing material, wherein hydrophobicity of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least two free thiol groups, thereby producing a thiol keratin-containing material sample, wherein the thiol keratin-containing material sample comprises a plurality of free thiol groups; and iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the hydrophobicity of the keratin-containing material.

In another aspect, the disclosure provides a method for treating a keratin-containing material, wherein hydrophobicity of the keratin-containing material is improved, comprising:

i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the hydrophobicity of the keratin-containing material.

BRIEF DESCRIPTION OF THE FIGURES

FIG. 4 depicts molecular structures of representative thiol compounds for thiol delivery.

DETAILED DESCRIPTION

Overview

Figure 1:
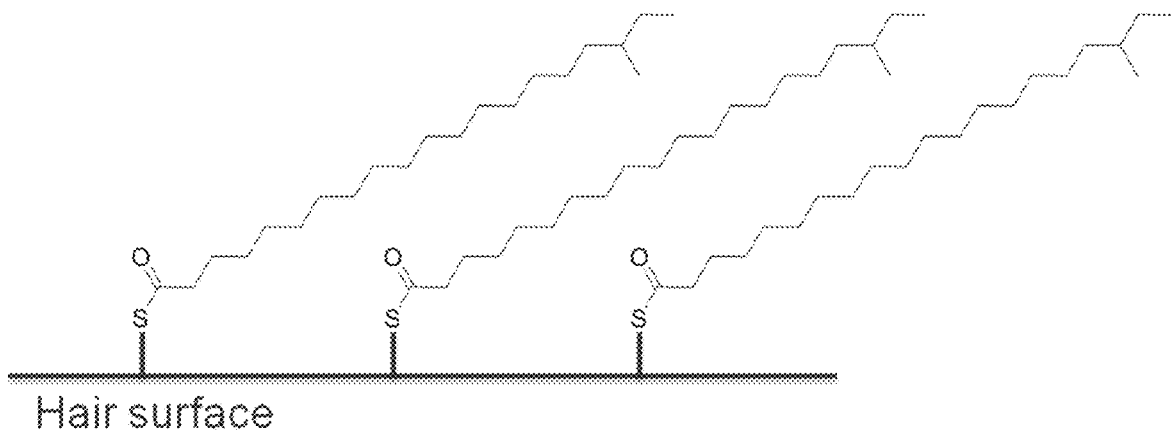
FIG. 1 depicts a cartoon illustrating the covalent attachment of the hydrophobic molecule 18-MEA to the surface of hair via a thioester linkage.

A keratin-containing material becomes weathered and damaged in response to stresses, including normal wear and tear, harsh cleaning agents (including solvents), washing, drying, brushing, combing, rubbing, styling, bleaching, dyeing, and sun exposure. Hair chemical services, such as permanent waving (perming), straightening, relaxing, and smoothing, all involve as the first step the cleavage of disulfide bonds to produce free thiol groups (i.e., hair reduction). Although the reduction chemistry is well known, strong reducing agents like ammonium thioglycolate (ATG) often are used to achieve reduction throughout the entire hair fiber, which may cause extensive cuticle damage and hair fiber breakage. Damage leads to functional degradation of a keratin-containing material. For example, when the natural 18-MEA layer is lost, and the hair surface becomes more hydrophilic, negatively charged, and damaged-feeling. An alternative method for generating free thiol groups in keratin-containing materials, also called a "thiol delivery" process, that is less damaging is still an unmet need. A long-term method for achieving healthy, strong, virgin-like keratin-containing material (e.g., nails and hair) is still an unmet need.

Exemplary Methods for Treating a Keratin-Containing Material

Provided herein are methods of delivering one or more thiol compounds to keratin-containing materials with minimal damage to the keratin-containing materials. In some embodiments, each thiol compound comprises at least one free thiol group. In some embodiments, each thiol compound comprises at least two free thiol groups. In some embodiments, at least one thiol compound comprises at least two free thiol groups.

In some embodiments, the keratin-containing material is selected from the group consisting of hair (including facial hair such as eyebrows, eyelashes, beards, and moustaches), fingernails and toenails. In some embodiments, the keratin-containing material is selected from the group consisting of hair, eyebrows, eyelashes, fingernails and toenails. In some embodiments, the keratin-containing material is hair. In some embodiments, the keratin-containing material is fingernails or toenails.

The disclosed methods provide for the formation of a disulfide bond between functional groups comprising the amino acid cysteine in keratin with a thiol group of a thiol compound, which forms in the presence of a catalyst.

In some embodiments of the methods disclosed herein, each thiol compound is independently selected from the group consisting of a monothiol compound, a protected thiol compound, a dithiol compound, a trithiol compound, a tetrathiol compound, a thiomer, and a cyclic disulfide compound. In one aspect, the disclosure provides a method for treating keratin-containing material, comprising:
  i) providing a keratin-containing material sample comprising a plurality of disulfide bonds; and
  ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds.

In some embodiments, the thiol compound is a monothiol compound, which comprises at least one additional functional group. In some embodiments, the thiol compound comprises at least one free thiol groups and at least one additional functional group. In some embodiments, the thiol compound comprises at least two free thiol groups and at least one additional functional group. In some embodiments, the one or more additional functional groups are selected from the group consisting of an alkyl, an alkene, an alkoxyl, an acetate, a cycloalkyl, a heterocycloalkyl, an aryl, a heteroaryl, an aryloxy, a heteroaryloxy, a poly(ethylene glycol), a carborane, an alkyl amine, an alkyl amide, an aralkyl, a heteroaralkyl, and a ferrocene, wherein the alkyl, the alkene, the acetate, the cycloalkyl, the heterocycloalkyl, the aryl, the heteroaryl, the aryloxy, the heteroaryloxy, the poly(ethylene glycol), the carborane, the alkyl amine, the alkyl amide, the aralkyl, the heteroaralkyl, and the ferrocene are optionally substituted.

In some embodiments, the thiol compound is a monothiol compound, which comprises at least one additional functional group. In one aspect, the disclosure provides a method for treating keratin-containing material, comprising:
  i) providing a keratin-containing material sample comprising a plurality of disulfide bonds; and
  ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of functional groups.

Figure 2:
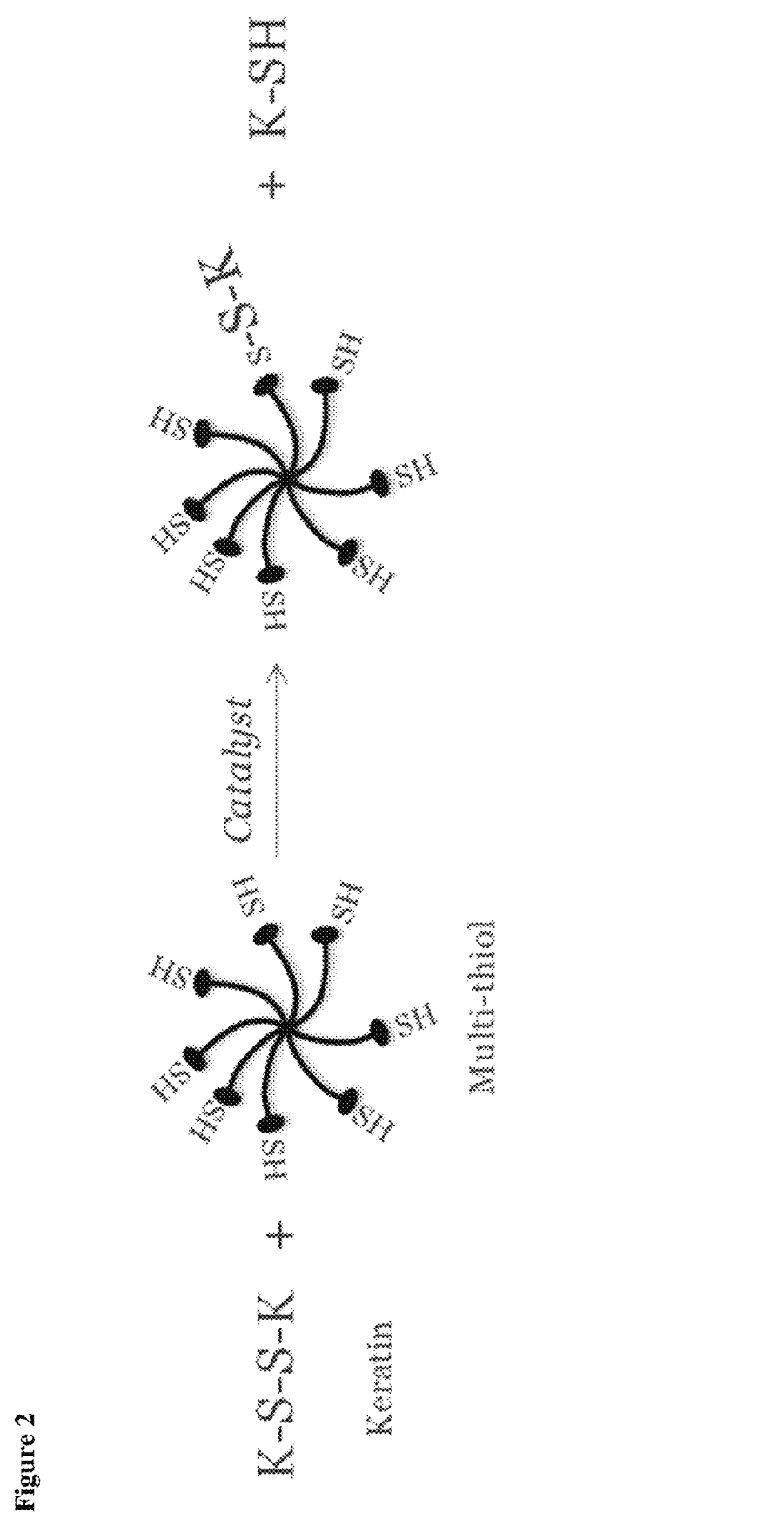
FIG. 2 is a schematic representation of the formation of a disulfide bond between functional groups comprising the amino acid cysteine in keratin with a thiol group of a thiol compound, which forms in the presence of a catalyst.

Without wishing to be bound by any theory, the proposed mechanism for thiol delivery occurs when a multi-thiol molecule reacts with a disulfide bond in keratin-containing materials (K-S-S-K) to generate multiple free thiol groups (FIG. 2). In some embodiments, the free thiol groups are amplified by reaction with a thiol compounds without extensive cleavage of disulfide bonds in the hair. In some embodiments, the free thiol groups can be used for further grafting. In some embodiments, the free thiol groups can be used for other hair treatments. In some embodiments, the disulfide bond in keratin formed between two cysteine residues is broken, and a new disulfide bond is formed between a cysteine residue of keratin and a free thiol group of the thiol compound.

In one aspect, the disclosure provides a method for treating keratin-containing material, comprising:
  i) providing a keratin-containing material sample comprising a plurality of disulfide bonds; and
  ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups.

In some embodiments of the methods disclosed herein, each thiol compound is independently selected from the group consisting of a monothiol compound, a protected thiol compound, a dithiol compound, a trithiol compound, a tetrathiol compound, a thiomer, and a cyclic disulfide compound. In one aspect, the disclosure provides a method for treating keratin-containing material, comprising:
  i) providing a keratin-containing material sample comprising a plurality of disulfide bonds; and
  ii) applying to the keratin-containing material sample for a period of time a mixture, comprising one or more thiol compounds; and an oxidizing agent, thereby producing a cross-linked keratin-containing material sample, wherein the cross-linked keratin-containing material sample comprises a plurality of covalent bonds between the keratin-containing material sample and the thiol compounds.

In some embodiments of the methods disclosed herein, the method for treating a keratin-containing material comprises:
  i) providing a keratin-containing material sample comprising a plurality of disulfide bonds;
  ii) applying to the keratin-containing material sample for a period of time a mixture, comprising one or more thiol compounds selected from the group consisting of L-cysteine, thioglycolic acid, thioglycerin, thiolactic acid, and N-acetyl-L-cysteine, thereby producing a cross-linked keratin-containing material sample wherein the cross-linked keratin-containing material sample comprises a plurality of covalent bonds between the keratin-containing material sample and the thiol compounds.

Figure 3A:
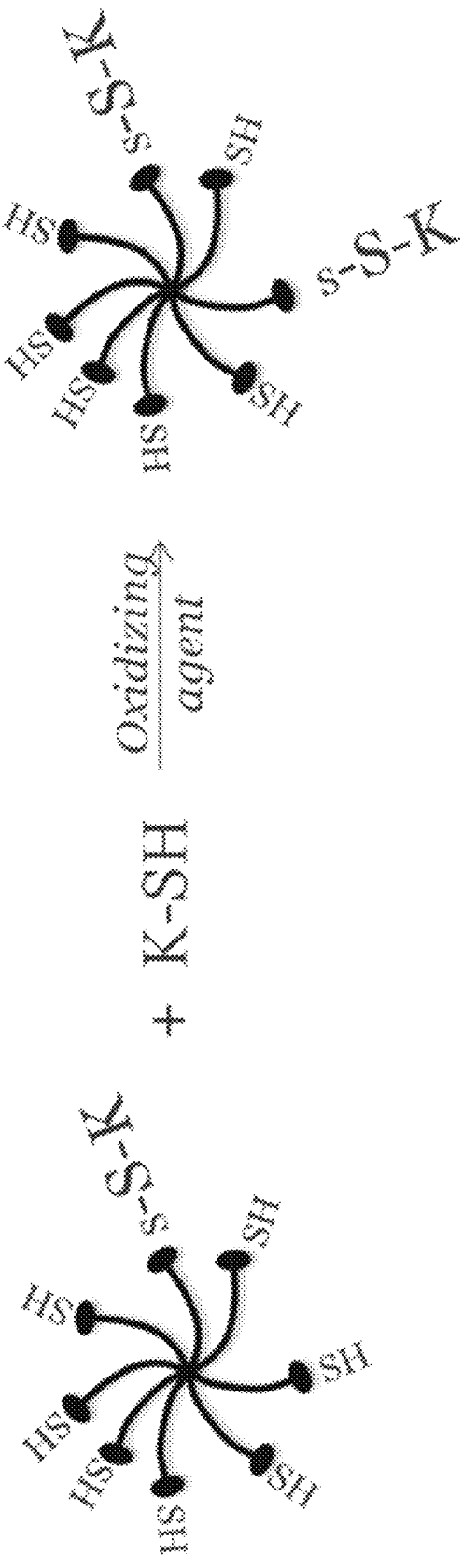
FIG. 3A is a schematic representation of a cross-linked keratin-containing material sample comprising two thiol keratin-containing material samples linked through a multi-thiol compound, which forms in the presence of an oxidizing agent.
Figure 3B:
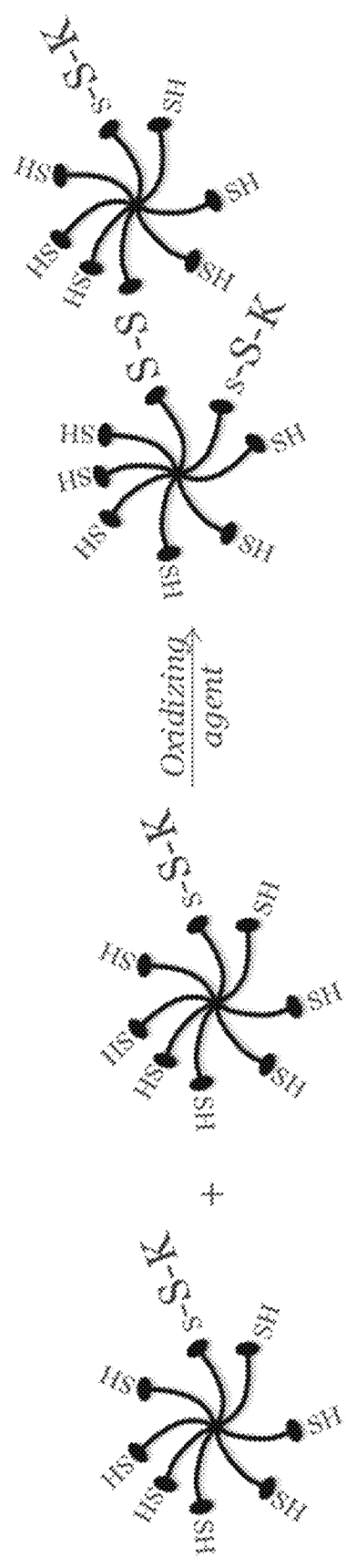
FIG. 3B is a schematic representation of a cross-linked keratin-containing material sample comprising two thiol keratin-containing material samples linked through two multi-thiol compounds, which forms in the presence of an oxidizing agent.

The thiol compound that comprises at least two free thiol groups can act as a cross-linker. In some embodiments, a cross-linked keratin-containing material sample comprises two thiol keratin-containing material samples linked through a multi-thiol compound, which forms in the presence of an oxidizing agent (FIG. 3A). In some embodiments, in the presence of an oxidizing environment, the multi-thiol molecule will react with free thiol group(s) in keratin-containing material to form inter- or intra-hair disulfide bonds. In some embodiments, two or more thiol compounds form disulfide bonds between the thiol compounds as well as disulfide bonds between a thiol compound and a keratin-containing material, so the linked two or more thiol compounds act as a cross-linker. In some embodiments, the cross-linker comprises at least two linked thiol compounds. In some embodiments, the cross-linked keratin-containing material sample comprises two thiol keratin-containing material samples linked through two multi-thiol compounds, which forms in the presence of an oxidizing agent (FIG. 3B). In some embodiments, in the presence of an oxidizing environment, the multi-thiol molecule will react with another multi-thiol molecule leading to the formation a poly-thiol network. In some embodiments, the methods of treating a keratin-containing material comprising an oxidizing agent reinforce and strengthen the keratin-containing material structure.

In some embodiments, the methods of treating a keratin-containing material comprise applying a mixture comprising one or more thiol compounds. In some embodiments, the mixture is applied in portions. In some embodiments, the mixture comprises a first mixture and a second mixture. In some embodiments, the first mixture comprises a first thiol compound. In some embodiments, the second mixture comprises a second thiol compound.

In some embodiments, the method for treating keratin-containing material comprises:
  i) providing a keratin-containing material sample comprising a plurality of disulfide bonds;
  ii) applying to the keratin-containing material sample for a period of time a first mixture, comprising a first thiol compound; and
  iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds.

In some embodiments, the method for treating keratin-containing material comprises:
  i) providing a keratin-containing material sample comprising a plurality of disulfide bonds;
  ii) applying to the keratin-containing material sample for a period of time a first mixture, comprising a first thiol compound and a catalyst; and
  iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds.

In another aspect, the disclosure provides a method for treating keratin-containing material, comprising:
  i) providing a keratin-containing material sample comprising a plurality of disulfide bonds; and
  ii) applying to the keratin-containing material sample for a period of time a mixture, comprising one or more thiol compounds, wherein each thiol compound comprises at least one free thiol group and at least one additional functional group; and an oxidizing agent, thereby producing a cross-linked keratin-containing material sample, wherein the cross-linked keratin-containing material sample comprises a plurality of disulfide bonds between the keratin-containing material sample and the thiol compounds.

In another aspect, the disclosure provides a method for treating keratin-containing material, comprising:
  i) providing a keratin-containing material sample comprising a plurality of disulfide bonds; and
  ii) applying to the keratin-containing material sample for a period of time a mixture, comprising one or more thiol compounds, wherein each thiol compound comprises at least two free thiol groups; and an oxidizing agent, thereby producing a cross-linked keratin-containing material sample, wherein the cross-linked keratin-containing material sample comprises a plurality of disulfide bonds between the keratin-containing material sample and the thiol compounds.

In another aspect, the disclosure provides a method for treating a keratin-containing material, comprising:
  i) providing a keratin-containing material sample comprising a plurality of disulfide bonds;
  ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds; and
  iii) applying an oxidizing agent, thereby producing a cross-linked keratin-containing material sample, wherein the cross-linked keratin-containing material sample comprises a plurality of covalent bonds between the covalently bonded keratin-containing material sample and the thiol compounds.

In another aspect, the disclosure provides a method for treating a keratin-containing material, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of functional groups; and
  iii) applying an oxidizing agent, thereby producing a cross-linked keratin-containing material sample, wherein the cross-linked keratin-containing material sample comprises a plurality of disulfide bonds between the keratin-containing material sample and the thiol compounds.

In another aspect, the disclosure provides a method for treating keratin-containing material, comprising:

i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
iii) applying an oxidizing agent, thereby producing a cross-linked keratin-containing material sample, wherein the cross-linked keratin-containing material sample comprises a plurality of disulfide bonds between the keratin-containing material sample and the thiol compounds.

In some embodiments of the methods disclosed herein, the keratin-containing material sample is first soaked in a solution of one or more thiol compounds, wherein each thiol compound comprises at least two free thiol groups and a catalyst. In some embodiments, the keratin-containing material sample is first soaked in a solution of one or more thiol compounds, wherein each thiol compound comprises at least two free thiol groups; and an oxidizing agent. In some embodiments, the keratin-containing material sample is first soaked in a solution of one or more thiol compounds, wherein each thiol compound comprises at least two free thiol groups; and a catalyst following by applying a solution comprising an oxidizing agent.

In some embodiments of the methods disclosed herein, the method further comprises the step of styling the thiol keratin-containing material sample. In some embodiments, the method further comprises the step of shaping the thiol keratin-containing material sample. In some embodiments, the thiol keratin-containing material sample is hair. In some embodiments, the hair is styled. In some embodiments, the hair is relaxed. In some embodiments, the hair is smoothed. In some embodiments, the hair is shaped. In some embodiments, the hair shape is selected from the group consisting of straightened, crimped, waved, and curled. In some embodiments, the hair is straightened. In some embodiments, the hair is crimped. In some embodiments, the hair is waved. In some embodiments, the hair is curled.

In some embodiments, grafting monomeric and polymeric materials to a thiol keratin-containing material can provide a covalent coating on a thiol keratin-containing material. A keratin-containing material sample comprises a plurality of disulfide bonds. A mixture comprising one or more thiol compounds is applied to the keratin-containing material sample. The thiol keratin-containing material sample then comprises a plurality of free thiol groups. A monomer is applied to the thiol keratin-containing material sample. The free thiol groups react with the monomer to form a plurality of covalent bonds between the free thiol groups and the monomers.

In some embodiments, the method is a two-step method for the attachment of functional molecules to keratin-containing material. In some embodiments, the functional molecules are hydrophobic. First, functional groups are delivered for the covalent attachment of monomers. Keratin-containing material, which consists primarily of the cysteine-rich protein keratin, contains a high concentration of disulfide bonds. In some embodiments, the first step of the grafting process is a thiol delivery step to attach free thiol functional groups to keratin-containing material (FIG. 2). Keratin reduction is commonly used today in salon services, such as permanent waving (perming), permanent straightening (Japanese perming), relaxing, and smoothing, and has been studied extensively for these purposes.[7-10] Although the reduction chemistry is well-known, providing free thiol groups on the keratin-containing material with minimal keratin-containing material damage has not been evaluated. In some embodiments, the thiol compound comprises at least one free thiol group and at least one additional functional group. In some embodiments, the one or more additional functional groups are selected from the group consisting of an alkene, an acrylate, and a methacrylate, In some embodiments, a functionalized keratin-containing material sample is provided after applying one or more thiol compounds followed by a grafted keratin-containing material sample after applying a monomer.

In another aspect, the disclosure provides a method for treating a keratin-containing material, comprising:
i) providing a keratin-containing material sample comprising a plurality of disulfide bonds;
ii) applying to the keratin-containing material sample for a period of time a mixture, comprising one or more thiol compounds, thereby producing a covalently bonded keratin-containing material sample, wherein the covalently bonded keratin-containing material sample comprises a plurality of disulfide bonds between the keratin-containing material sample and the thiol compounds; and
iii) applying a monomer to the covalently bonded keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the covalently bonded keratin-containing material and the monomers.

In another aspect, the disclosure provides a method for treating a keratin-containing material, comprising:
i) providing a keratin-containing material sample comprising a plurality of disulfide bonds;
ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds; and
iii) applying a monomer to the covalently bonded keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the covalently bonded keratin-containing material and the monomers.

In another aspect, the disclosure provides a method for treating a keratin-containing material, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least one free thiol group and at least one additional functional group, thereby producing a functionalized keratin-containing material sample, wherein the functionalized keratin-containing material sample comprises a plurality of free functional groups; and
iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers.

In another aspect, the disclosure provides a method for treating keratin-containing material, comprising:

i) providing a keratin-containing material sample comprising a plurality of disulfide bonds;

ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers.

In some embodiments, a thiol keratin-containing material sample is provided after applying one or more thiol compounds followed by a grafted keratin-containing material sample after applying a monomer. In another aspect, the disclosure provides a method for treating keratin-containing material, comprising:

i) providing a keratin-containing material sample comprising a plurality of disulfide bonds;

ii) applying to the keratin-containing material sample for a period of time a mixture, comprising one or more thiol compounds, wherein each thiol compound comprises at least two free thiol groups, thereby producing a thiol keratin-containing material sample, wherein the thiol keratin-containing material sample comprises a plurality of free thiol groups; and iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers.

In another aspect, the disclosure provides a method for treating keratin-containing material, comprising:

i) providing a keratin-containing material sample comprising a plurality of disulfide bonds;

ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers.

In some embodiments, the method further comprises rinsing the keratin-containing material sample between steps ii) and iii). In some embodiments, the method further comprises washing the keratin-containing material sample between steps ii) and iii). In some embodiments, the method further comprises drying the keratin-containing material sample after washing and before step iii). In some embodiments, the method further comprises washing, rinsing, and drying the keratin-containing material sample between steps ii) and iii).

In some embodiments, the method is semi-simultaneous. In some embodiments, the keratin-containing material sample is first soaked in a solution of one or more thiol compounds, wherein each thiol compound comprises at least two free thiol groups;

optionally, a catalyst; and then monomer is directly added to the keratin-containing material sample. In some embodiments, the keratin-containing material sample is first soaked in a solution of one or more thiol compounds, wherein each thiol compound comprises at least two free thiol groups; optionally, a catalyst; and optionally, an oxidizing agent; and then monomer is directly added to the keratin-containing material sample.

In some embodiments, a keratin-containing material sample is not rinsed between steps ii) and iii). In some embodiments, a keratin-containing material sample is not washed between steps ii) and iii). In some embodiments, a keratin-containing material sample is not washed nor dried between steps ii) and iii). In some embodiments, a keratin-containing material sample is not rinsed, washed, or dried between steps ii) and iii).

In another aspect, the disclosure provides a method for treating keratin-containing material, comprising:

i) providing a keratin-containing material sample comprising a plurality of disulfide bonds;

ii) applying to the keratin-containing material sample for a period of time a mixture, comprising one or more thiol compounds, wherein each thiol compound comprises at least two free thiol groups, in a concentration of about 0.1% by weight to about 15% by weight; and a catalyst, wherein the keratin-containing material sample comprises a plurality of free thiol groups; and iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers.

In some embodiments of the methods disclosed herein, each thiol compound is independently selected from the group consisting of a monothiol compound, a protected thiol compound, a dithiol compound, a trithiol compound, a tetrathiol compound, a thiomer, and a cyclic disulfide compound. In some embodiments, the protected thiol compound is deprotected to form a thiol compound comprising at least one free thiol group. In some embodiments, the thiol compound comprises a thioether group and a thiol protecting group to form a protected thiol compound.

In some embodiments, the thiol compound is a monothiol compound, which comprises at least one additional functional group. In some embodiments, the thiol compound comprises at least one free thiol group and at least one additional functional group. In some embodiments, the thiol compound comprises at least two free thiol groups and at least one additional functional group.

In some embodiments, the additional functional group is selected from the group consisting of an alkyl, an alkene, an alkoxyl, an acetate, a cycloalkyl, a heterocycloalkyl, an aryl, a heteroaryl, an aryloxy, a heteroaryloxy, a poly(ethylene glycol), a carborane, an alkyl amine, an alkyl amide, an aralkyl, a heteroaralkyl, and a ferrocene, wherein the alkyl, the alkene, the acetate, the cycloalkyl, the heterocycloalkyl, the aryl, the heteroaryl, the aryloxy, the heteroaryloxy, the poly(ethylene glycol), the carborane, the alkyl amine, the alkyl amide, the aralkyl, the heteroaralkyl, and the ferrocene are optionally substituted.

In some embodiments, the monothiol compound is selected from the group consisting of 1-butanethiol, 1-decanethiol, 1-dodecanethiol, 1-heptanethiol, 1-hexadecanethiol, 1-hexanethiol, 1-nonanethiol, 1-octadecanethiol, 1-octanethiol, 1-pentadecanethiol, 1-pentanethiol, 1-propanethiol, 1-tetradecanethiol, 1-decanethiol, 1-undecanethiol, 1-dodecanethiol, 11-mercaptoundecyl trifluoroacetate, 1H,1H,2H,2H-perfluorodecanethiol, 2-ethylhexanethiol, 2-methyl-1-propanethiol, 2-methyl-2-propanethiol, 3,3,4,4,5,5,6,6,6-nonafluoro-1-hexanethiol, 3-mercapto-N-nonyl-propionamide, 3-methyl-1-butanethiol, 4-cyano-1-butanethiol, butyl 3-mercaptopropionate, cis-9-octadecene-1-thiol, methyl 3-mercaptopropionate, tert-dodecylmercaptan, tert-nonyl mercaptan, 1,1',4',1"-terphenyl-4-thiol, 1,4-benzenedimethanethiol, 1-adamantanethiol, 1-naphthalenethiol, 2-phenylethanethiol, 4'-bromo-4-mercaptobiphenyl, 4'-mercaptobiphenylcarbonitrile, 4,4'-bis(mercaptomethyl)biphenyl, 4-dimercaptostilbene, 4-(6-mercaptohexyloxy)benzyl alcohol, 4-mercaptobenzoic acid, 9-fluorenylmethylthiol, 9-mercaptofluorene, biphenyl-4-thiol, cyclohexanethiol, cyclopentanethiol, m-carborane-1-thiol, m-carborane-9-thiol, thiophenol, triphenylmethanethiol, L-cysteine, thioglycolic acid, thioglycerin, thiolactic acid, and N-acetyl L-cysteine. In some embodiments, the monothiol compound is selected from the group consisting of 1-butanethiol, 1-decanethiol, 1-dodecanethiol, 1-heptanethiol, 1-hexadecanethiol, 1-hexanethiol, 1-nonanethiol, 1-octadecanethiol, 1-octanethiol, 1-pentadecanethiol, 1-pentanethiol, 1-propanethiol, 1-tetradecanethiol, 1-decanethiol, 1-undecanethiol, 1-dodecanethiol, 11-mercaptoundecyl trifluoroacetate, 1H,1H,2H,2H-perfluorodecanethiol, 2-ethylhexanethiol, 2-methyl-1-propanethiol, 2-methyl-2-propanethiol, 3,3,4,4,5,5,6,6,6-nonafluoro-1-hexanethiol, 3-mercapto-N-nonyl-propionamide, 3-methyl-1-butanethiol, 4-cyano-1-butanethiol, butyl 3-mercaptopropionate, cis-9-octadecene-1-thiol, methyl 3-mercaptopropionate, tert-dodecylmercaptan, tert-nonyl mercaptan, 1,1',4',1"-terphenyl-4-thiol, 1,4-benzenedimethanethiol, 1-adamantanethiol, 1-naphthalenethiol, 2-phenylethanethiol, 4'-bromo-4-mercaptobiphenyl, 4'-mercaptobiphenylcarbonitrile, 4,4'-bis(mercaptomethyl)biphenyl, 4-dimercaptostilbene, 4-(6-mercaptohexyloxy)benzyl alcohol, 4-mercaptobenzoic acid, 9-fluorenylmethylthiol, 9-mercaptofluorene, biphenyl-4-thiol, cyclohexanethiol, cyclopentanethiol, m-carborane-1-thiol, m-carborane-9-thiol, thiophenol, triphenylmethanethiol, thioglycerin, and N-acetyl L-cysteine.

In some embodiments, the monothiol compound is selected from the group consisting of (11-mercaptoundecyl)-N,N,N-trimethylammonium bromide, (11-mercaptoundecyl)hexa(ethylene glycol), (11-mercaptoundecyl)tetra (ethylene glycol), 1-(11-mercaptoundecyl)imidazole, 1-mercapto-2-propanol, 11-(1H-pyrrol-1-yl)undecane-1-thiol, 11-(ferrocenyl)undecanethiol, 11-amino-1-undecanethiol hydrochloride, 11-azido-1-undecanethiol, 11-mercapto-1-undecanol, 11-mercaptoundecanamide, 11-mercaptoundecanoic acid, 11-mercaptoundecylhydroquinone, 11-mercaptoundecylphos-phonic acid, 12-mercaptododecanoic acid, 16-amino-1-hexadecanethiol hydrochloride, 16-mercaptohexadecanamide, 16-mercaptohexadecanoic acid, 3-amino-1-propanethiol hydrochloride, 3-chloro-1-propanethiol, 3-mercapto-1-propanol, 3-mercaptopropionic acid, 4-mercapto-1-butanol, 6-(ferrocenyl)hexanethiol, 6-amino-1-hexanethiol hydrochloride, 6-mercapto-1-hexanol, 6-mercaptohexanoic acid, 8-amino-1-octanethiol hydrochloride, 8-mercapto-1-octanol, 8-mercaptooctanoic acid, 9-mercapto-1-nonanol, triethylene glycol mono-11-mercaptoundecyl ether, L-cysteine, thioglycolic acid, thioglycerin, thiolactic acid, and N-acetyl L-cysteine. In some embodiments, the monothiol compound is selected from the group consisting of (11-mercaptoundecyl)-N,N,N-trimethylammonium bromide, (11-mercaptoundecyl)hexa(ethylene glycol), (11-mercaptoundecyl)tetra (ethylene glycol), 1-(11-mercaptoundecyl)imidazole, 1-mercapto-2-propanol, 11-(1H-pyrrol-1-yl)undecane-1-thiol, 11-(ferrocenyl)undecanethiol, 11-amino-1-undecanethiol hydrochloride, 11-azido-1-undecanethiol, 11-mercapto-1-undecanol, 11-mercaptoundecanamide, 11-mercaptoundecanoic acid, 11-mercaptoundecylhydroquinone, 11-mercaptoundecylphos-phonic acid, 12-mercaptododecanoic acid, 16-amino-1-hexadecanethiol hydrochloride, 16-mercaptohexadecanamide, 16-mercaptohexadecanoic acid, 3-amino-1-propanethiol hydrochloride, 3-chloro-1-propanethiol, 3-mercapto-1-propanol, 3-mercaptopropionic acid, 4-mercapto-1-butanol, 6-(ferrocenyl)hexanethiol, 6-amino-1-hexanethiol hydrochloride, 6-mercapto-1-hexanol, 6-mercaptohexanoic acid, 8-amino-1-octanethiol hydrochloride, 8-mercapto-1-octanol, 8-mercaptooctanoic acid, 9-mercapto-1-nonanol, triethylene glycol mono-11-mercaptoundecyl ether, thioglycerin, and N-acetyl L-cysteine. In some embodiments, the monothiol compound is L-cysteine, thioglycolic acid, thioglycerin, thiolactic acid, and N-acetyl L-cysteine. In some embodiments, the monothiol compound is N-acetyl L-cysteine.

In some embodiments, the thiol compound comprises at least two free thiol groups and at least one additional functional group. In some embodiments, the thiol compound is 4,4'-dimercaptostilbene.

In some embodiments, the thiol compound comprises at least two free thiol groups. In some embodiments, the thiol compound is a multi-thiol compound. In some embodiments, each thiol compound is independently selected from the group consisting of a dithiol compound, a trithiol compound, a tetrathiol compound, a thiomer (i.e., a polymer comprising at least two free thiol groups), and a cyclic disulfide compound.

In some embodiments, the free thiol group of the thiol compound is masked to form a protected thiol compound. In some embodiments, the protected thiol compound comprises a thioether group and a thiol protecting group. In some embodiments, the thiol protecting group is an acetate. In some embodiments, the protected thiol compound is selected from the group consisting of 1,4-butanedithiol diacetate, [11-(methylcarbonylthio)undecyl]hexa(ethylene glycol) methyl ether, [11-(methylcarbonylthio)undecyl]tetra (ethylene glycol), [11-(methylcarbonylthio)undecyl]-trnethylene glycol) acetic acid, [11-(methylcarbonylthio)undecyl] trnethylene glycol) methyl ether, hexa(ethylene glycol) mono-11-(acetylthio)undecyl ether, S,S'-[1,4-Phenylenebis (2,1-ethynediyl-4,1-phenylene)]bis(thioacetate), S-[4-[2-[4-

(2-phenylethynyl)phenyl]ethynyl]-phenyl] thioacetate, S-(10-undecenyl) thioacetate, S-(11-bromoundecyl) thioacetate, S-(4-azidobutyl)thioacetate, S-(4-bromobutyl) thioacetate, and S-(4-cyanobutyl)thioacetate.

In another aspect, the disclosure provides a method for treating keratin-containing material, comprising:
i) providing a keratin-containing material sample comprising a plurality of disulfide bonds; and
ii) applying to the keratin-containing material sample for a period of time a mixture, comprising one or more protected thiol compounds, wherein each protected thiol compound comprises at least one thiol group and at least one thiol protecting group; and an oxidizing agent, thereby producing a thiol keratin-containing material sample, wherein the thiol keratin-containing material sample comprises a plurality of free thiol groups, which further react to produce a cross-linked keratin-containing material sample, wherein the cross-linked keratin-containing material sample comprises a plurality of disulfide bonds between the keratin-containing material sample and the thiol compounds.

In another aspect, the disclosure provides a method for treating keratin-containing material, comprising:
i) providing a keratin-containing material sample comprising a plurality of disulfide bonds;
ii) applying to the keratin-containing material sample for a period of time a mixture, comprising one or more protected thiol compounds, wherein each protected thiol compound comprises at least one thiol group and at least one thiol protecting group; and a catalyst, thereby producing a thiol keratin-containing material sample, wherein the thiol keratin-containing material sample comprises a plurality of free thiol groups; and
iii) applying an oxidizing agent, thereby producing a cross-linked keratin-containing material sample, wherein the cross-linked keratin-containing material sample comprises a plurality of disulfide bonds between the keratin-containing material sample and the thiol compounds.

In some embodiments of the methods disclosed herein, the thiol compound is a protected thiol compound. In some embodiments, the protected thiol compound comprises at least one additional functional group. In some embodiments, the protected thiol compound is deprotected to form a thiol compound comprising at least one free thiol group.

In some embodiments, the thiol compound is a thiomer, wherein the thiomer is a polymer comprising at least two free thiol groups. In some embodiments, the thiol compound is selected from the group consisting of a dithiol compound, a trithiol compound, a tetrathiol compound, a hexathiol compound, and an octathiol compound. In some embodiments, the thiol compound is a tetrathiol compound. In some embodiments, the thiol compound is a multi-arm poly(ethylene glycol) (PEG) comprising at least two free thiol groups or a multi-arm poly(ethylene oxide) comprising at least two free thiol groups. In some embodiments, the thiol compound is selected from the group consisting of 4arm-PEG2K-SH, 4arm-PEG5K-SH, 4arm-PEG10K-SH, 4arm-PEG20K-SH, 4-arm poly(ethylene oxide) thiol-terminated, 8arm-PEG10K-SH (hexaglyerol core), 8arm-PEG10K-SH (tripentaerythritol core), 8arm-PEG20K-SH (hexaglyerol core), 8arm-PEG20K-SH (tripentaerythritol core), and 8-arm poly(ethylene oxide) thiol-terminated. These thiomers are available from Millipore Sigma (formerly Sigma Aldrich). In some embodiments, the thiol compound is 4-arm poly(ethylene oxide) thiol-terminated. In some embodiments, the thiol compound is 4arm-PEG2K-SH (also referred to as a 4-arm poly(ethylene glycol) thiol; see FIG. 4).

In some embodiments, the thiol compound is selected from the group consisting of dithiothreitol (DTT); 1,2-ethanedithiol; 1,3-propanedithiol; 1,4-butanedithiol; 1,5-pentanedithiol; 1,6-hexanedithiol; 1,7-heptanedithiol; 1,8-octanedithiol; 1,9-nonanedithiol; 1,10-decanedithiol; 1,11-undecanedithiol; 1,12-dodecanedithiol; 1,13-tridecanedithiol; 1,14-tetradecanedithiol; 1,16-hexadecanedithiol; dithiolbutylamine (DTBA); tetra(ethylene glycol) dithiol; hexa(ethylene glycol) dithiol; 2-mercaptoethyl ether; 2,2'-thiodiethanethiol; 2,2'-(ethylenedioxy)diethanethiol; propane-1,2,3-trithiol; trimethylolpropane tris(2-mercaptoacetate); trimethylolpropane tris(3-mercaptoacetate); pentaerythrityl tetrathiol; pentaerythritol tetrakis(3-mercaptopropionate); 1,2-dithiane-4,5-diol; lipoic acid (alpha lipoic acid and beta lipoic acid); 3H-1,2-dithiole; 3-propyl-1,2-dithiolane; 3-acetyl-1,2-dithiolane; 1,2-dithiolane-4-carboxylic acid; 1,2-dithiolane-3-pentanol; 1,2,4-dithiazolidine; 1,2-dithiane; 1,2-dithiepane; 1,2-dithiocane; and 1,2-dithiocane-3,8-diol. In some embodiments, the thiol compound is selected from the group consisting of dithiothreitol (DTT), 1,2-ethanedithiol, 1,3-propanedithiol, 1,4-butanedithiol, 1,5-pentanedithiol, 1,6-hexanedithiol, 1,7-heptanedithiol, 1,8-octanedithiol, 1,9-nonanedithiol, 1,10-decanedithiol, 1,11-undecanedithiol, 1,12-dodecanedithiol, 1,13-tridecanedithiol, 1,14-tetradecanedithiol, 1,16-hexadecanedithiol, dithiolbutylamine (DTBA), tetra(ethylene glycol) dithiol, hexa(ethylene glycol) dithiol, 2-mercaptoethyl ether, 2,2'-thiodiethanethiol, 2,2'-(ethylenedioxy)diethanethiol, propane-1,2,3-trithiol, trimethylolpropane tris (2-mercaptoacetate), trimethylolpropane tris(3-mercaptoacetate), pentaerythrityl tetrathiol, and pentaerythritol tetrakis(3-mercaptopropionate). In some embodiments, the dithiol compound is selected from the group consisting of dithioerythritol, DTT, and dihydrolipoic acid. In some embodiments, the tetrathiol compound is pentaerythritol tetrakis(3-mercaptopropionate).

In some embodiments, the thiol compound is a cyclic disulfide compound. In some embodiments, the thiol compound is a cyclic disulfide compound selected from the group consisting of 1,2-dithiane-4,5-diol; lipoic acid (alpha lipoic acid and beta lipoic acid); 3H-1,2-dithiole; 3-propyl-1,2-dithiolane; 3-acetyl-1,2-dithiolane; 1,2-dithiolane-4-carboxylic acid; 1,2-dithiolane-3-pentanol; 1,2,4-dithiazolidine; 1,2-dithiane; 1,2-dithiepane; 1,2-dithiocane; and 1,2-dithiocane-3,8-diol. In some embodiments, the thiol compound is alpha lipoic acid. In some embodiments, the cyclic disulfide has a structural formula selected from the group consisting of:

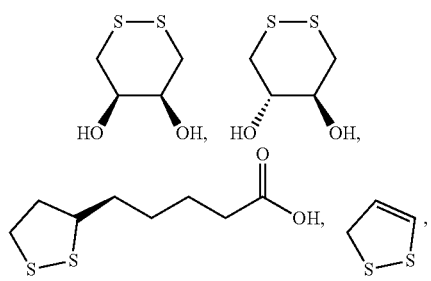

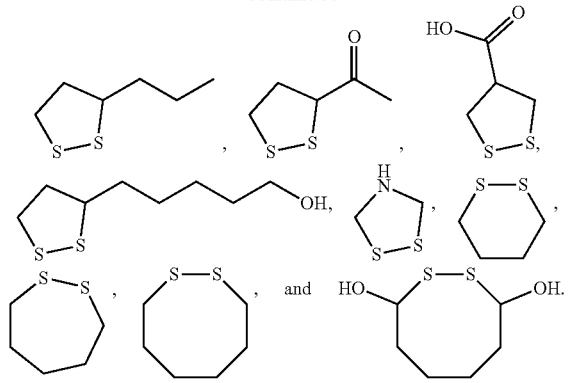

In some embodiments of the methods disclosed herein, the concentration of the thiol compound in the mixture is about 0.05% by weight to about 60% by weight. In some embodiments of the methods disclosed herein, the concentration of the thiol compound in the mixture is about 0.05% by weight to about 50% by weight. In some embodiments, the concentration of the thiol compound in the mixture is selected from the group consisting of about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.08%, about 0.9%, about 0.95%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, and about 50% by weight. In some embodiments, the concentration of the thiol compound in the mixture is about 0.1% by weight to about 11% by weight. In some embodiments, the concentration of the thiol compound in the mixture is about 3% by weight to about 10% by weight. In some embodiments, the concentration of the thiol compound in the mixture is about 5% by weight to about 10% by weight. In some embodiments, the concentration of the thiol compound in the mixture is about 7% by weight to about 9% by weight. In some embodiments, the concentration of the thiol compound in the mixture is about 0.05% by weight to about 5% by weight. In some embodiments, the concentration of the thiol compound in the mixture is about 5% by weight to about 20% by weight. In some embodiments, the concentration of the thiol compound in the mixture is about 0.1% by weight to about 5% by weight. In some embodiments, the concentration of the thiol compound in the mixture is about 0.5% by weight to about 5% by weight. In some embodiments, the concentration of the thiol compound in the mixture is about 1% by weight to about 4% by weight. In some embodiments, the concentration of the thiol compound in the mixture is about 8% by weight. In some embodiments, the concentration of the thiol compound in the mixture is about 5% by weight. In some embodiments, the concentration of the thiol compound in the mixture is about 2.5% by weight.

In some embodiments, the concentration of the thiol compound in the mixture is low. In some embodiments, the concentration of the thiol compound in the mixture is less than about 11% by weight. In some embodiments, the concentration of the thiol compound in the mixture is less than about 10% by weight. In some embodiments, the concentration of the thiol compound in the mixture is less than about 9% by weight. In some embodiments, the concentration of the thiol compound in the mixture is less than about 8% by weight. In some embodiments, the concentration of the thiol compound in the mixture is less than about 7% by weight. In some embodiments, the concentration of the thiol compound in the mixture is less than about 6% by weight. In some embodiments, the concentration of the thiol compound in the mixture is less than about 5% by weight. In some embodiments, the concentration of the thiol compound in the mixture is less than about 4% by weight. In some embodiments, the concentration of the thiol compound in the mixture is less than about 3% by weight. In some embodiments, the concentration of the thiol compound in the mixture is less than about 2% by weight. In some embodiments, the concentration of the thiol compound in the mixture is less than about 1% by weight.

In some embodiments, the method for treating keratin-containing material minimizes keratin-containing material damage. In some embodiments, the keratin-containing material is hair. In some embodiments, the disclosed methods for treating hair are less damaging than a method of permanently waving hair. In some embodiments, applying the disclosed methods for treating hair are less damaging than a method of permanently straightening hair. In some embodiments, applying the disclosed methods for treating hair are less damaging than a method of shaping hair.

In some embodiments of the methods disclosed herein, the ratio by weight of the mixture to the keratin-containing material sample (also referred to herein as a liquor ratio) is about 1:10 to about 500:1. In some embodiments, the ratio is selected from the group consisting of about 1:10, about 2:10, about 3:10, about 4:10, about 5:10, about 6:10, about 7:10, about 8:10, about 9:10, about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, about 30:1, about 31:1, about 32:1, about 33:1, about 34:1, about 35:1, about 36:1, about 37:1, about 38:1, about 39:1, about 40:1, about 41:1, about 42:1, about 43:1, about 44:1, about 45:1, about 46:1, about 47:1, about 48:1, about 49:1, about 50:1, about 51:1, about 52:1, about 53:1, about 54:1, about 55:1, about 56:1, about 57:1, about 58:1, about 59:1, about 60:1, about 61:1, about 62:1, about 63:1, about 64:1, about 65:1, about 66:1, about 67:1, about 68:1, about 69:1, about 70:1, about 71:1, about 72:1, about 73:1, about 74:1, about 75:1, about 76:1, about 77:1, about 78:1, about 79:1, about 80:1, about 81:1, about 82:1, about 83:1, about 84:1, about 85:1, about 86:1, about 87:1, about 88:1, about 89:1, about 90:1, about 91:1, about 92:1, about 93:1, about 94:1, about 95:1, about 96:1, about 97:1, about 98:1, about 99:1, about 100:1, about 101:1, about 102:1, about 103:1, about 104:1, about 105:1, about 106:1, about 107:1, about 108:1, about 109:1, about 110:1, about 115:1, about 120:1, about 125:1, about 130:1, about 135:1, about 140:1, about 145:1, about 150:1, about 155:1, about 160:1, about 165:1, about 170:1, about 175:1, about 180:1, about 185:1, about 190:1, about 195:1, about 200:1, about 205:1, about 210:1, about 215:1, about 220:1, about 225:1, about 230:1, about 235:1, about 240:1, about 245:1, about 250:1, about 255:1, about 260:1, about 265:1, about 270:1, about 275:1, about 280:1, about 285:1, about 290:1, about 295:1, about 300:1, about 310:1, about 320:1, about 330:1, about 340:1, about 350:1, about 360:1, about 370:1, about 380:1, about 390:1, about 400:1, about 410:1, about 420:1, about 430:1, about 440:1, about 450:1, about 460:1, about 470:1, about 480:1, about 490:1, and about 500:1. In some embodiments, the ratio is about 1:10 to about 100:1. In some embodiments, the ratio is about 1:1 to about 100:1. In some embodiments, the ratio is about 1:1 to about 20:1. In some embodiments, the ratio is about 2:1 to about 10:1. In some embodiments, the ratio is about 3:1 to about 10:1. In some embodiments, the ratio is about 5:1.

In some embodiments, the liquor ratio is low. In some embodiments, the ratio is less than about 50:1. In some embodiments, the ratio is less than about 20:1. In some embodiments, the ratio is less than about 10:1.

In some embodiments of the methods disclosed herein, the mixture is applied overnight. In some embodiments of the methods disclosed herein, the mixture is applied for about 1 hour to about 12 hours. In some embodiments, the mixture is applied for a period of time selected from the group consisting of about 1 hour, about 1.25 hours, about 1.5 hours, about 1.75 hours, about 2 hours, about 2.25 hours, about 2.5 hours, about 2.75 hours, about 3 hours, about 3.25 hours, about 3.5 hours, about 3.75 hours, about 4 hours, about 4.25 hours, about 4.5 hours, about 4.75 hours, about 5 hours, about 5.25 hours, about 5.5 hours, about 5.75 hours, about 6 hours, about 6.25 hours, about 6.5 hours, about 6.75 hours, about 7 hours, about 7.25 hours, about 7.5 hours, about 7.75 hours, about 8 hours, about 8.25 hours, about 8.5 hours, about 8.75 hours, about 9 hours, 9.25 hours, about 9.5 hours, about 9.75 hours, about 10 hours, about 10.25 hours, about 10.5 hours, about 10.75 hours, about 11 hours, about 11.25 hours, about 11.5 hours, about 11.75 hours, and about 12 hours. In some embodiments, the mixture is applied for about 5 hours to about 12 hours. In some embodiments, the mixture is applied for about 6 hours to about 10 hours. In some embodiments, the mixture comprises one or more thiol compounds. In some embodiments, the mixture comprises one or more thiol compounds in a concentration of about 0.1% by weight to about 15% by weight.

In some embodiments of the methods disclosed herein, the mixture is applied for about 30 seconds to about 180 minutes. In some embodiments, the mixture is applied for a period of time selected from the group consisting of about 30 seconds, about 45 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 125 minutes, about 130 minutes, about 135 minutes, about 140 minutes, about 145 minutes, about 150 minutes, about 155 minutes, about 160 minutes, about 165 minutes, about 170 minutes, about 175 minutes, and about 180 minutes. In some embodiments, the mixture is applied for about 30 seconds to about 60 minutes. In some embodiments, the mixture is applied for about 1 minute to about 45 minutes. In some embodiments, the mixture is applied for about 15 minutes to about 45 minutes. In some embodiments, the mixture is applied for about 30 minutes. In some embodiments, the mixture is applied for about 1 minute to about 25 minutes. In some embodiments, the mixture comprises one or more thiol compounds and a catalyst. In some embodiments, the mixture comprises one or more thiol compounds and an oxidizing agent.

In some embodiments, the mixture is applied for a short time. In some embodiments, the mixture is applied for less than about 60 minutes. In some embodiments, the mixture is applied for less than about 45 minutes. In some embodiments, the mixture is applied for less than about 40 minutes. In some embodiments, the mixture is applied for less than about 30 minutes.

In some embodiments, the monomer is applied to the thiol keratin-containing material sample within about 30 minutes after applying the mixture to the keratin-containing material sample. In some embodiments, the monomer is applied to the thiol keratin-containing material sample within a period of time selected from the group consisting of about 30 seconds, about 45 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, and about 30 minutes after applying the mixture to the keratin-containing material sample. In some embodiments, the monomer is applied to the thiol keratin-containing material sample within about 15 minutes of applying the mixture to the keratin-containing material sample. In some embodiments, the monomer is applied to the thiol keratin-containing material sample within about 10 minutes of applying the mixture to the keratin-containing material sample. In some embodiments, the monomer is applied to the thiol keratin-containing material sample within about 5 minutes of applying the mixture to the keratin-containing material sample. In some embodiments, the monomer is applied to the thiol keratin-containing material sample within about 1 minute of applying the mixture to the keratin-containing material sample.

In some embodiments of the methods disclosed herein, the monomer is applied for about 30 seconds to about 180 minutes. In some embodiments, the monomer is applied for a period of time selected from the group consisting of about 30 seconds, about 45 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 125 minutes, about 130 minutes, about 135 minutes, about 140 minutes, about 145 minutes, about 150 minutes, about 155 minutes, about 160 minutes, about 165 minutes, about 170 minutes, about 175 minutes, and about 180 minutes. In some embodiments, the monomer is applied for about 30 seconds to about 60 minutes. In some embodiments, the monomer is applied for about 1 minute to about 30 minutes. In some embodiments, the monomer is applied for about 15 minutes to about 30 minutes. In some embodiments, the monomer is applied for about 30 minutes. In some embodiments, the monomer is applied for about 15 minutes. In some embodiments, the monomer is applied for about 1 minute to about 10 minutes.

In some embodiments of the methods disclosed herein, the mixture further comprises a buffer solution. In some embodiments, the buffer solution is selected from the group consisting of phosphate, phosphate buffered saline, imidazole-HCl, 4-morpholineethanesulfonic acid (MES); bis(2-hydroxyethyl)-amino-tris(hydroxymethyl)methane (bis-Tris); N-(2-acetamido)iminodiacetic acid; N-(2-acetamido)-2-aminoethanesulfonic acid; 1,4-piperazinediethanesulfonic acid; 3-morpholino-2-hydroxypropanesulfonic acid (MOPSO); 1,3-bis[tris(hydroxymethyl)methyl-amino]propane; N,N-bis(2-hydroxyethyl)-2-aminoethanesufonic acid; 4-morpholinepropanesulfonic acid (MOPS); 2-[(2-hydroxy-1,1-bis(hydroxymethyl)ethyl)-amino]ethanesulfonic acid; 4-(2-hydroxyethyl)piperazine-1-ethanesulfonic acid (HEPES); 3-(N,N-bis[2-hydroxyethyl]amino)-2-hydroxypropanesulfonic acid; 4-(N-morpholino)butane-sulfonic acid; 2-hydroxy-3-[tris(hydroxymethyl)methylamino]-1-propanesulfonic acid; tris(hydroxymethyl)aminomethane; piperazine-N,N'-bis(2-hydroxypropanesulfonic acid); 4-(2-hydroxyethyl)-1-piperazinepropane-sulfonic acid; N-[tris(hydroxymethyl)methyl]glycine; diglycine; N,N-bis(2-hydroxyethyl)-glycine, N-(2-hydroxyethyl)piperazine-N'-(4-butanesulfonic acid); N-[tris(hydroxymethyl)-methyl]-3-aminopropanesulfonic acid; N-(1,1-dimethyl-2-hydroxyethyl)-3-amino-2-hydroxypropanesulfonic acid; 2-(cyclohexylamino)-ethanesulfonic acid; 3-(cyclohexylamino)-2-hydroxy-1-propanesulfonic acid; 2-amino-2-methyl-2-propanol; sodium carbonate-sodium bicarbonate; 3-(cyclohexylamino)-1-propanesulfonic acid; and 4-(cyclohexylamino)-1-butanesulfonic acid.

In some embodiments of the methods disclosed herein, the pH of the mixture is about 0.1 to about 14. In some embodiments, the pH of the mixture is about 1 to about 13. In some embodiments of the methods disclosed herein, the pH of the mixture is about 5 to about 14. In some embodiments of the methods disclosed herein, the pH of the mixture is selected from the group consisting of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, about 12.0, about 12.1, about 12.2, about 12.3, about 12.4, about 12.5, about 12.6, about 12.7, about 12.8, about 12.9, about 13.0, about 13.1, about 13.2, about 13.3, about 13.4, about 13.5, about 13.6, about 13.7, about 13.8, about 13.9, and about 14.0. In some embodiments, the pH of the mixture is about 7 to about 14. In some embodiments, the pH of the mixture is about 8 to about 13. In some embodiments, the pH of the mixture is about 10 to about 11.

In some embodiments of the methods disclosed herein, the pH of the mixture is about 0.1 to about 6. In some embodiments of the methods disclosed herein, the pH of the mixture is selected from the group consisting of about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, and about 6.0. In some embodiments, the pH of the mixture is about 1 to about 5. In some embodiments, the pH of the mixture is about 1 to about 4.

In some embodiments of the methods disclosed herein, the method further comprises applying to the keratin-containing material sample for a period of time an additive. In some embodiments, the additive is applied to the keratin-containing material sample between steps i) and ii). In some embodiments, the additive is applied to the keratin-containing material sample as a pre-treatment. In some embodiments of the methods disclosed herein, the mixture further comprises an additive. In some embodiments, the mixture of step ii) further comprises an additive. In some embodiments, the additive is applied to the keratin-containing material sample after step ii). In some embodiments, the additive is applied to the keratin-containing material sample after step iii). In some embodiments, the additive is applied to the keratin-containing material sample as a post-treatment.

In some embodiments of the methods disclosed herein, the method for treating a keratin-containing material comprises:

i) providing a keratin-containing material sample comprising a plurality of disulfide bonds;
ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds; and
iii) applying to the keratin-containing material sample for a period of time an additive.

In some embodiments, the method for treating keratin-containing material comprises:
i) providing a keratin-containing material sample comprising a plurality of disulfide bonds;
ii) applying to the keratin-containing material sample for a period of time a first mixture, comprising a first thiol compound;
iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds; and
iv) applying to the keratin-containing material sample for a period of time an additive.

In another aspect, the disclosure provides a method for treating a keratin-containing material, comprising:
i) providing a keratin-containing material sample comprising a plurality of disulfide bonds;
ii) applying to the keratin-containing material sample for a period of time a mixture, comprising one or more thiol compounds, thereby producing a covalently bonded keratin-containing material sample, wherein the covalently bonded keratin-containing material sample comprises a plurality of disulfide bonds between the keratin-containing material sample and the thiol compounds;
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
iv) applying to the keratin-containing material sample for a period of time an additive.

In some embodiments, the method for treating keratin-containing material comprises:
i) providing a keratin-containing material sample comprising a plurality of disulfide bonds;
ii) applying to the keratin-containing material sample for a period of time a first mixture, comprising a first thiol compound;
iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds;
iv) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
v) applying to the keratin-containing material sample for a period of time an additive.

In some embodiments, the additive is selected from the group consisting of preservatives, emollients, monoterpenoids, fatty alcohols, fatty acids, fatty esters, fluorinated small molecules (e.g., perfluoromethylcyclopentane, perfluoroperhydrophenanthrene, perfluoro-1,3-dimethylcyclohexane, perfluoromethyldecalin, and perfluoroperhydrobenzyltetralin). In some embodiments, the additive is selected from the group consisting of citric acid, ethylenediaminetetraacetic acid (EDTA), tert-Butyl alcohol, tert-Amyl alcohol, 3-Methyl-3-pentanol, Ethchlorvynol, 1-Octanol, Pelargonic alcohol, 1-Decanol (or decyl alcohol or capric alcohol), Undecyl alcohol (or 1-undecanol, undecanol, or hendecanol), Lauryl alcohol (or dodecanol or 1-dodecanol), Tridecyl alcohol (or 1-tridecanol, tridecanol, or isotridecanol), Myristyl alcohol (or 1-tetradecanol), Pentadecyl alcohol (or 1-pentadecanol or pentadecanol), Cetyl alcohol (or 1-hexadecanol), Palmitoleyl alcohol (or cis-9-hexadecen-1-ol), Heptadecyl alcohol (or 1-n-heptadecanol or heptadecanol), Stearyl alcohol (or 1-octadecanol), Oleyl alcohol, Nonadecyl alcohol (or 1-nonadecanol), Arachidyl alcohol (or 1-eicosanol), Heneicosyl alcohol (or 1-heneicosanol), Behenyl alcohol (or 1-docosanol), Erucyl alcohol (or cis-13-docosen-1-ol), Lignoceryl alcohol (or 1-tetracosanol), Ceryl alcohol (or 1-hexacosanol), 1-Heptacosanol, Montanyl alcohol, cluytyl alcohol, or 1-octacosanol, 1-Nonacosanol, Myricyl alcohol, melissyl alcohol, or 1-triacontanol, 1-Dotriacontanol (Lacceryl alcohol), Geddyl alcohol (1-tetratriacontanol), Cetearyl alcohol, Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid, Caprylic acid, Capric acid, Lauric acid, Myristic acid, Palmitic acid, Stearic acid, Arachidic acid, Behenic acid, Lignoceric acid, Cerotic acid, linoleic acid, carvone, isoborneol, eucalyptol, camphor, α-pinene, resveratrol, linolenic acid, palmitic acid, myristyl alcohol, cetyl alcohol, oleyl alcohol, octadecanol, hexyl laurate, glyceryl laurate, dicaprylyl ether, octafluoropentyl methacrylate, stearic acid, oleic acid, ethylhexyl palmitate, octyl stearate, isostearyl alcohol, and isoamyl laurate. In some embodiments, the additive is selected from the group consisting of citric acid, ethylenediaminetetraacetic acid (EDTA), tert-butyl alcohol, tert-amyl alcohol, 3-methyl-3-pentanol, ethchlorvynol, 1-octanol, pelargonic alcohol, 1-decanol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, heneicosyl alcohol, behenyl alcohol, erucyl alcohol, lignoceryl alcohol, ceryl alcohol, 1-heptacosanol, montanyl alcohol, cluytyl alcohol, 1-nonacosanol, myricyl alcohol, melissyl alcohol, 1-dotriacontanol, geddyl alcohol, cetearyl alcohol, myristoleic acid, palmitoleic acid, sapienic acid, oleic acid, elaidic acid, vaccenic acid, linoleic acid, linoelaidic acid, linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, carvone, isoborneol, eucalyptol, camphor, α-pinene, resveratrol, hexyl laurate, glyceryl laurate, dicaprylyl ether, octafluoropentyl methacrylate, ethylhexyl palmitate, octyl stearate, isostearyl alcohol, and isoamyl laurate.

In some embodiments, the additive is selected from the group consisting of a fatty acid, a fatty alcohol, an amino acid mixture, a peptide mixture, an acidifier, a polycarboxylic acid, or a mixture thereof.

In some embodiments, the additive is a fatty acid, a fatty alcohol, or a mixture thereof. In some embodiments, the fatty acid or fatty alcohol is selected from the group consisting of butyric acid, caproic acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, linolenic acid, arachidonic acid, eicosapentaenoic acid, erucic acid, docosahexaenoic acid, argan oil, coconut oil, jojoba oil, olive oil, palm oil, capryl alcohol (or 1-octanol), pelargonic alchol (or 1-nonanol), capric alcohol (or 1-decanol or decyl alcohol), undecyl alcohol (or 1-undecanol, undecanol, or hendecanol), lauryl alcohol (or dodecanol or 1-dodecanol), tridecyl alcohol (or 1-tridecanol, tridecanol, or isotridecanol), myristyl alcohol (or 1-tetradecanol), pentadecyl alcohol (or 1-pentadecanol or pentadecanol), cetyl alcohol (or 1-hexadecanol), palmitoleyl alcohol (or cis-9-hexadecen-1-ol), heptadecyl alcohol (or 1-n-heptadecanol or heptadecanol), stearyl alcohol (or 1-octadecanol), oleyl alcohol, nonadecyl alcohol or 1-nonadecanol), arachidyl alcohol (or 1-eicosanol), heneicosyl alcohol (or 1-heneicosanol), behenyl alcohol (or 1-docosanol), erucyl alcohol (or cis-13-docosen-1-ol), lignoceryl alcohol (or 1-tetracosanol), ceryl alcohol (or 1-hexacosanol), 1-heptacosanol, octacosyl alcohol (or 1-octacosanol, montanyl alcohol, or cluytyl alcohol), 1-nonacosanol, myricyl alcohol (or melissyl alcohol or 1-triacontanol), 1-dotriacontanol (or lacceryl alcohol), geddyl alcohol (or 1-tetratriacontanol), cetearyl alcohol (or cetostearyl alcohol or cetylstearyl alcohol), and a mixture thereof. In some embodiments, the fatty acid is selected from the group consisting of butyric acid, caproic acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, linolenic acid, arachidonic acid, eicosapentaenoic acid, erucic acid, docosahexaenoic acid, jojoba oil, argan oil, coconut oil, jojoba oil, olive oil, palm oil, and a mixture thereof. In some embodiments, the fatty acid is selected from the group consisting of oleic acid, linoleic acid, jojoba oil, and a mixture thereof. In some embodiments, the fatty alcohol is selected from the group consisting of capryl alcohol, pelargonic alchol, capric alcohol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, heneicosyl alcohol, behenyl alcohol, erucyl alcohol, lignoceryl alcohol, ceryl alcohol, and a mixture thereof. In some embodiments, the fatty alcohol is cetyl alcohol or cetearyl alcohol.

In some embodiments, the additive is an amino acid mixture or a peptide mixture. In some embodiments, the additive is an amino acid mixture comprising one or more amino acids (naturally occurring L-form or D-form), which may be identified by the conventional three-letter abbreviations indicated in the below table.

TABLE 1

(Amino acid codes)

| Name | 3-letter code |
| --- | --- |
| Alanine | Ala |
| Arginine | Arg |
| Asparagine | Asn |
| Aspartic acid | Asp |
| Cysteine | Cys |
| Glutamic acid | Glu |
| Glutamine | Gln |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

In some embodiments, the additive is an amino acid mixture comprising one or more amino acids or an N-acetylated amino acid (e.g., N-acetyl alanine, Ac-Ala). In some embodiments, the additive comprises an amino acid mixture selected from the group consisting of glycine (Gly), L-alanine (L-Ala), L-serine (L-Ser), L-cysteine (L-Cys), N-acetyl glycine (Ac-Gly), N-acetyl alanine (Ac-Ala), N-acetyl cysteine (Ac-Cys or NALC), and N-acetyl serine (Ac-Ser). In some embodiments, the additive comprises an amino acid mixture selected from the group consisting of Ac-Gly, Ac-Ala, and Ac-Ser. In some embodiments, the additive comprises an amino acid mixture or a peptide mixture used in personal care industries. In some embodiments, the additive comprises an amino acid mixture or peptide mixture selected from the group consisting of FISION® KeraVeg 18 (blend of vegetable amino acids), PRODEW® 500 (amino acid blend), Vegetamide 18MEA-NJ (cetearamidoethyldiethonium succinoyl hydrolyzed pea protein), Vegetamide 18MEA-MR (cetearamidoethyl diethonium hydrolyzed rice protein), KERARICE™ (rice peptides and amino acids), KERATRIX™ (carob tree hydrolyzate), Promois WK-PD (hydrolyzed keratin), and GLUADIN® Kera-P LM (low molecular weight vegetable peptides). In some embodiments, the additive is KERATRIX™.

In some embodiments, the additive comprises an acidifier, a polycarboxylic acid, or a mixture thereof. In some embodiments, the additive comprises an acidifier or a polycarboxylic acid selected from the group consisting of aldobionic acid, azelaic acid, citric acid, ethylenediaminetetra-acetic acid, ethylenediamine-N,N'-disuccinic acid, gluconolactone, glutamic acid N,N-diacetic acid, lactic acid, methylglycinediacetic acid, tartaric acid, and a mixture thereof. In some embodiments, the additive comprises an acidifier or a polycarboxylic acid selected from the group consisting of citric acid, gluconolactone, glutamic acid N,N-diacetic acid, tartaric acid, and mixtures thereof. In some embodiments, the additive comprises citric acid and gluconolactone. In some embodiments, the additive is citric acid.

In some embodiments, the concentration of the additive is about 0.1% by weight to about 15% by weight. In some embodiments, the concentration of the additive is selected from the group consisting of about 0.1%, about 0.2%, about 0.3%, about 0.4%, about 0.5%, about 0.6%, about 0.7%, about 0.8%, about 0.9%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, and about 15% by weight. In some embodiments, the concentration of the additive is about 0.1% by weight to about 10% by weight. In some embodiments, the concentration of the additive is about 0.1% by weight to about 8% by weight. In some embodiments, the concentration of the additive is about 0.1% by weight to about 5% by weight. In some embodiments, the concentration of the additive is about 2% by weight. In some embodiments, the concentration of each additive is about 2% by weight.

In some embodiments, the additive improves delivery of the one or more thiol compounds. In some embodiments, the additive improves the efficiency of delivery of the one or more thiol compounds.

In some embodiments, the additive improves the sensory properties of the keratin-containing material. In some embodiments, the sensory properties are tactile properties (e.g., manageability, smoothness, conditioned feeling) and/or visual properties (e.g., frizz, fiber alignment, and curl shape).

In some embodiments of the methods disclosed herein, the molar ratio of the catalyst to the additive is about 50:1 to about 1:100. In some embodiments, the molar ratio of the catalyst to the additive is about 30:1 to about 1:100. In some embodiments, the molar ratio of the catalyst to the additive is selected from the group consisting of about 3:0.9, about 3:0.8, about 3:0.7, about 3:0.6, about 3:0.5, about 3:0.4, about 3:0.2, about 3:0.1, about 2:0.9, about 2:0.8, about 2:0.7, about 2:0.6, about 2:0.5, about 2:0.4, about 2:0.2, about 2:0.1, about 1:0.9, about 1:0.8, about 1:0.7, about 1:0.6, about 1:0.5, about 1:0.4, about 1:0.2, about 1:0.1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2.5:1, about 2:1, about 1.5:1, about 1:1, about 1:20, about 1:21, about 1:22, about 1:23, about 1:24, about 1:25, about 1:26, about 1:27, about 1:28, about 1:29, about 1:30, about 1:31, about 1:32, about 1:33, about 1:34, about 1:35, about 1:36, about 1:37, about 1:38, about 1:39, about 1:40, about 1:41, about 1:42, about 1:43, about 1:44, about 1:45, about 1:46, about 1:47, about 1:48, about 1:49, about 1:50, about 1:51, about 1:52, about 1:53, about 1:54, about 1:55, about 1:56, about 1:57, about 1:58, about 1:59, about 1:60, about 1:61, about 1:62, about 1:63, about 1:64, about 1:65, about 1:66, about 1:67, about 1:68, about 1:69, about 1:70, about 1:71, about 1:72, about 1:73, about 1:74, about 1:75, about 1:76, about 1:77, about 1:78, about 1:79, about 1:80, about 1:81, about 1:82, about 1:83, about 1:84, about 1:85, about 1:86, about 1:87, about 1:88, about 1:89, about 1:90, about 1:91, about 1:92, about 1:93, about 1:94, about 1:95, about 1:96, about 1:97, about 1:98, about 1:99, and about 1:100. In some embodiments, the molar ratio of the catalyst to the additive is selected from the group consisting of about 3:0.9, about 3:0.8, about 3:0.7, about 3:0.6, about 3:0.5, about 3:0.4, about 3:0.2, about 3:0.1, about 2:0.9, about 2:0.8, about 2:0.7, about 2:0.6, about 2:0.5, about 2:0.4, about 2:0.2, about 2:0.1, about 1:0.9, about 1:0.8, about 1:0.7, about 1:0.6, about 1:0.5, about 1:0.4, about 1:0.2, and about 1:0.1. In some embodiments, the molar ratio of the catalyst to the additive is about 2:0.9, about 2:0.8, about 2:0.7, about 2:0.6, about 2:0.5, about 2:0.4, about 2:0.2, and about 2:0.1. In some embodiments, the molar ratio of the catalyst to the additive is about 2:0.6 to about 2:0.2. In some embodiments, the molar ratio of the catalyst to the additive is about 2:0.4.

In some embodiments of the methods disclosed herein, the monomer is selected from the group consisting of an acrylate, a methacrylate, a monomer comprising a vinyl group, and a monomer comprising a maleimide group. In some embodiments, the monomer is selected from the group consisting of an acrylate, a methacrylate, a monomer comprising a vinyl group, and a monomer comprising an alkyne group. In some embodiments, the monomer is an acrylate, a methacrylate, or a monomer comprising a vinyl group. In some embodiments, the monomer is an acrylate, a methacrylate, or a monomer comprising a maleimide group. In some embodiments, the monomer is an acrylate or a methacrylate. In some embodiments, the monomer is an alkyl acrylate or a cycloalkyl acrylate.

In some embodiments, the monomer is hydrophobic. In some embodiments, the monomer forms a coating on the keratin-containing material sample.

In some embodiments, the coating mimics the behavior of the natural lipid layer (18-methyleicosanoic acid, 18-MEA) found on naïve (or virgin) hair emerging from the follicle. 18-MEA functions as a protective barrier and leaves the hair with a smooth feeling and enhanced fiber alignment that lasts much longer compared to wash-off conditioning treatments.

In some embodiments, the coating mimics the behavior of virgin keratin-containing material. In some embodiments, the monomer is a long-chain acrylate. In some embodiments, the monomer is a branched monomer. In some embodiments, the monomer is a branched alkyl acrylate.

In some embodiments, the covalent attachment of the monomer to the keratin-containing material sample is a click chemistry reaction. Click chemistry reactions feature fast and complete conversion, and high functional group tolerance.[11,12]

Figure 5A:
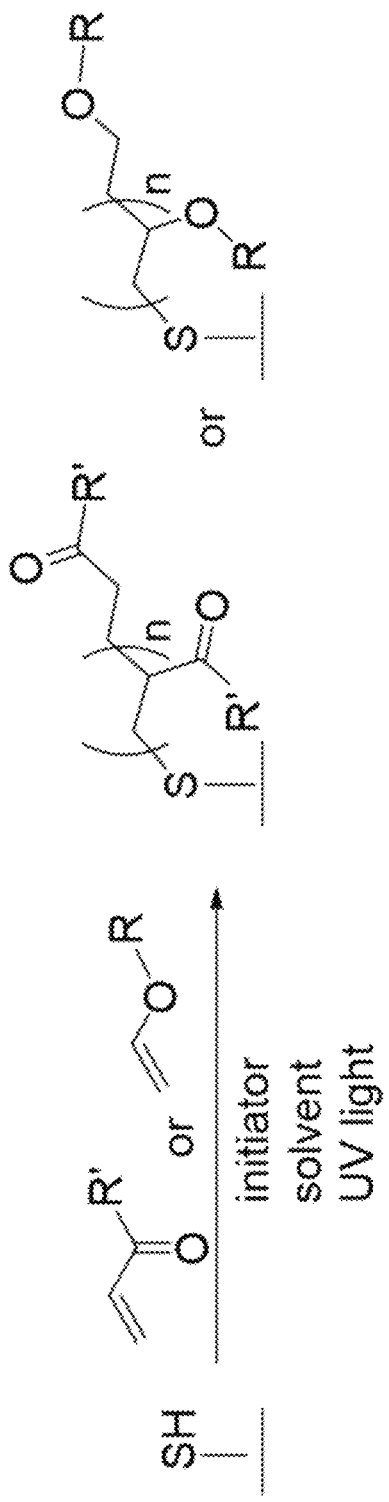
FIG. 5A is a schematic representation of free thiol functional groups initiating a polymerization with olefin-containing molecules, such as acrylates or vinyl ethers, using a radical thiol-ene reaction mediated by a photoinitiator and UV light.

In some embodiments, the covalent attachment of terminal "ene" molecules to the free thiols is via a thiol-ene radical addition (FIG. 5A). Without being bound by any theory, it is proposed that when utilizing the radical thiol-ene mechanism, the ene monomers propagate from thiols on the keratin-containing material to generate surface bound polymers and oligomers. If the ene monomers are capable of polymerizing without thiol functional groups, it is also possible to obtain free homopolymers that are not attached to the keratin-containing material.[13]

Figure 5B:
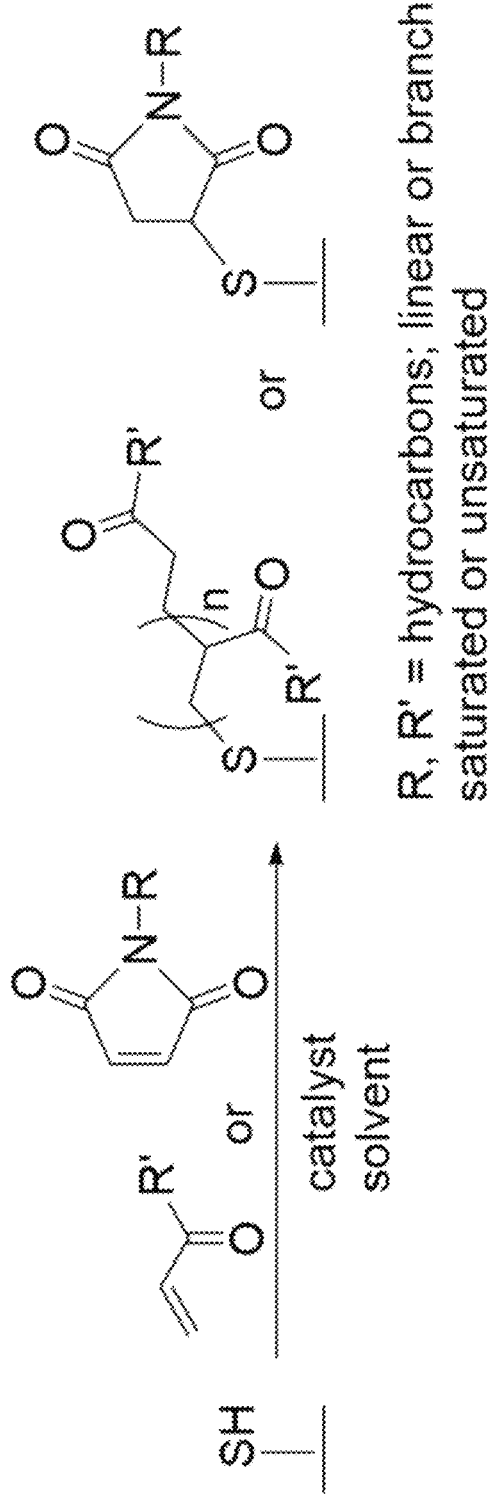
FIG. 5B is a schematic representation of free thiol functional groups acting as nucleophiles, and adding across the double bond of electrophilic olefin-containing monomers, such as acrylates or maleimides.

In some embodiments, the covalent attachment of terminal "ene" molecules to the free thiols is by thiol-Michael addition (FIG. 5B). The thiol-Michael addition allows grafting of monomers onto keratin-containing material fibers without generating unwanted homopolymer byproduct. Without being bound by any theory, it is proposed that this mechanism consists solely of the addition of a nucleophilic thiol adds across one electrophilic ene monomer.[14]

In some embodiments, the monomer is selected from the group consisting of ethyl acrylate; propyl acrylate; isobutyl acrylate; butyl acrylate; pentyl acrylate; tert-butyl acrylate; hexyl acrylate; heptyl acrylate; octyl acrylate; isooctyl acrylate; nonyl acrylate; decyl acrylate; isodecyl acrylate;

dodecyl acrylate; tridecyl acrylate; tetradecyl acrylate; hexadecyl acrylate; octadecyl acrylate; cyclopentyl acrylate; cyclohexyl acrylate; cycloheptyl acrylate; cyclooctyl acrylate; 2-(dimethylamino)ethyl acrylate; 2-(diethylamino) ethyl acrylate; 2-ethylhexyl acrylate; 3,5,5-trimethylhexyl acrylate; 8-methylnonyl acrylate; 3-isobutylnonyl acrylate; 3-(cyclohexylmethyl)nonyl acrylate; 3-butyl-7,11-dimethyldodecyl acrylate; (E)-3-butyl-7,11-dimethyldodec-2-en-1-yl acrylate; isobornyl acrylate; a poly(ethylene glycol) (PEG) acrylate; 1,6-hexanediol diacrylate; octafluoropentyl acrylate; fluorescein-o-acrylate; fluorescein-o-o-diacrylate; and a PEG-diacrylate. In some embodiments, the monomer is selected from the group consisting of isobutyl acrylate; butyl acrylate; tert-butyl acrylate; hexyl acrylate; isodecyl acrylate; dodecyl acrylate; tetradecyl acrylate; hexadecyl acrylate; octadecyl acrylate; cyclohexyl acrylate; 2-(dimethylamino)ethyl acrylate; 2-ethylhexyl acrylate; 8-methylnonyl acrylate; 3-isobutylnonyl acrylate; 3-(cyclohexylmethyl) nonyl acrylate; 3-butyl-7,11-dimethyldodecyl acrylate; (E)-3-butyl-7,11-dimethyldodec-2-en-1-yl acrylate; isobornyl acrylate; a PEG acrylate; 1,6-hexanediol diacrylate; octafluoropentyl acrylate; fluorescein-o-acrylate; fluorescein-o-o-diacrylate; and a PEG-diacrylate. In some embodiments, the monomer is selected from the group consisting of hexyl acrylate; isodecyl acrylate; dodecyl acrylate; tetradecyl acrylate; hexadecyl acrylate; octadecyl acrylate; 2-ethylhexyl acrylate; 3-isobutylnonyl acrylate; 3-(cyclohexylmethyl)nonyl acrylate; 3-butyl-7,11-dimethyldodecyl acrylate; (E)-3-butyl-7,11-dimethyldodec-2-en-1-yl acrylate; isobornyl acrylate; a PEG acrylate; and a PEG diacrylate. In some embodiments, the monomer is selected from the group consisting of hexyl acrylate; isodecyl acrylate; dodecyl acrylate; octadecyl acrylate; 2-ethylhexyl acrylate; 3-butyl-7,11-dimethyldodecyl acrylate; (E)-3-butyl-7,11-dimethyldodec-2-en-1-yl acrylate; isobornyl acrylate; a PEG acrylate; and a PEG diacrylate. In some embodiments, the monomer is hexyl acrylate or dodecyl acrylate. In some embodiments, the monomer is a PEG-diacrylate. In some embodiments, the monomer is a poly(ethylene glycol)-diacrylate or polyethylene glycol diacrylate (PEG diacrylate or PEG-DA) selected from the group consisting of PEG-DA 250, PEG-DA 575, PEG-DA 700, PEG-DA 1k, PEG-DA 1.5k, PEG-DA 2k, and PEG-DA 6k. In some embodiments, the monomer is selected from the group consisting of PEG-DA 700, PEG-DA 1k, and PEG-DA 2k. In some embodiments, the monomer is PEG-DA 700, In some embodiments, the monomer is PEG-DA 1.5k. In some embodiments, the monomer is PEG-DA 2k. The numbers refer to the number average molecular weight. That is, PEG-DA 700 refers to poly(ethylene glycol) diacrylate with a number average molecular weight of 700, and PEG-DA 1.5k refers to poly(ethylene glycol) diacrylate with a number average molecular weight of 1,500. In some embodiments, the monomer is an acrylate, which is a multi-arm PEG-acrylate (PEG-AA). In some embodiments, the monomer is a multi-arm PEG-acrylate selected from the group consisting of 4-arm PEG-AA 2k, 4-arm PEG-AA 5k, 4-arm PEG-AA 10k, 8-arm PEG-AA 5k, and 8-arm PEG-AA 20k.

In some embodiments, the monomer is a monomer comprising a vinyl group. In some embodiments, the monomer comprising a vinyl group is selected from the group consisting of a vinyl sulfone, an acrylate group, a methacrylate group, a styrene group, an acrylamide group, a methacrylamide group, a maleimide group, a maleate group, a fumarate group, and an itaconate group. In some embodiments, the monomer is selected from the group consisting of ethyl vinyl ether; propyl vinyl ether; isobutyl vinyl ether; butyl vinyl ether; pentyl vinyl ether; tert-butyl vinyl ether; hexyl vinyl ether; heptyl vinyl ether; octyl vinyl ether; isooctyl vinyl ether; nonyl vinyl ether; decyl vinyl ether; dodecyl vinyl ether; tetradecyl vinyl ether; hexadecyl vinyl ether; octadecyl vinyl ether; N,N-dimethyl-2-(vinyloxy)-ethylamine; cyclopentyl vinyl ether; cyclohexyl vinyl ether; cycloheptyl vinyl ether; cyclooctyl vinyl ether; 2-(dimethylamino)ethyl vinyl ether; 2-(diethylamino)ethyl vinyl ether; 2-ethylhexyl vinyl ether; 1-(vinyloxy)adamantane; vinyloxy-timethylsilane; and vinyloxy-triethylsilane. In some embodiments, the monomer is selected from the group consisting of isobutyl vinyl ether; butyl vinyl ether; dodecyl vinyl ether; octadecyl vinyl ether; cyclohexyl vinyl ether; and vinyloxy-triethylsilane.

In some embodiments, the monomer is a monomer comprising a maleimide group. In some embodiments, the monomer is selected from the group consisting of N-ethylmaleimide; N-cyclohexylmaleimide; N-arachidonylmaleimide; fluorescein-5-maleimide; a succinimidyl-RN-maleimidopropionamido)-diethyleneglycoll ester (an NHS-PEG$_n$-maleimide); a poly(ethylene glycol) (PEG)-maleimide; a PEG-methyl ether maleimide (an mPEG-maleimide); and a methoxy-PEG-maleimide. In some embodiments, the monomer is selected from the group consisting of N-ethylmaleimide; an NHS-PEG$_n$-maleimide; a PEG-maleimide; an mPEG-maleimide; and a methoxy-PEG-maleimide. In some embodiments, the monomer is N-ethylmaleimide or a PEG-maleimide.

In some embodiments of the methods disclosed herein, the molar ratio of the monomer to the free thiol groups is about 100:1 to about 1:500. In some embodiments, the molar ratio of the monomer to the free thiol groups is about 10:1 to about 1:500. In some embodiments, the molar ratio of the monomer to the free thiol groups is about 10:1 to about 1:100. In some embodiments, the molar ratio of the monomer to the free thiol groups is selected from the group consisting of about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2.5:1, about 2:1, about 1.5:1, about 1:1, about 9:10, about 8:10, about 7:10, about 6:10, about 5:10, about 4:10, about 3:10, about 2:10, about 1:10, about 1:11, about 9:100, about 1:12, about 2:25 (about 0.08:1), about 1:13, about 1:14, about 7:100, about 1:15, about 1:16, about 3:50, about 1:17, about 1:18, about 1:19, about 1:20, about 1:21, about 1:22, about 1:23, about 1:24, about 1:25, about 1:26, about 1:27, about 1:28, about 1:29, about 1:30, about 1:31, about 1:32, about 3:100, about 1:33, about 1:34, about 1:35, about 1:36, about 1:37, about 1:38, about 1:39, about 1:40, about 1:41, about 1:42, about 1:43, about 1:44, about 1:45, about 1:46, about 1:47, about 1:48, about 1:49, about 1:50, about 1:51, about 1:52, about 1:53, about 1:54, about 1:55, about 1:56, about 1:57, about 1:58, about 1:59, about 1:60, about 1:61, about 1:62, about 1:63, about 1:64, about 1:65, about 1:66, about 1:67, about 1:68, about 1:69, about 1:70, about 1:71, about 1:72, about 1:73, about 1:74, about 1:75, about 1:76, about 1:77, about 1:78, about 1:79, about 1:80, about 1:81, about 1:82, about 1:83, about 1:84, about 1:85, about 1:86, about 1:87, about 1:88, about 1:89, about 1:90, about 1:91, about 1:92, about 1:93, about 1:94, about 1:95, about 1:96, about 1:97, about 1:98, about 1:99, and about 1:100. In some embodiments, the molar ratio of the monomer to the free thiol groups is selected from the group consisting of about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2.5:1, about 2:1, about 1.5:1, about 1:1, about 0.9:1, about 0.8:1, about 0.7:1, about 0.6:1, about 0.5:1, about 0.4:1, about 0.3:1, about 0.2:1, about 0.1:1, about 0.09:1, about 0.08:1, about 0.07:1, about 0.06:1, about 0.05:1, about 0.04:1, about 0.03:1, about 0.02:1, and about 0.01:1. In some embodiments, the molar ratio of the monomer to the free thiol groups is about 5:1 to about 1:100. In some embodiments, the molar ratio of the monomer to the free thiol groups is about 3:1 to about 1:15. In some embodiments, the molar ratio of the monomer to the free thiol groups is about 1:1 to about 1:2. In some embodiments, the molar ratio of the monomer to the free thiol groups is about 0.05:1 to about 5:1. In some embodiments, the molar ratio of the monomer to the free thiol groups is about 0.07:1 to about 3:1. In some embodiments, the molar ratio of the monomer to the free thiol groups is about 0.5:1 to about 1:1.

In some embodiments of the methods disclosed herein, the concentration of the monomer is about 0.5% by weight to about 95% by weight. In some embodiments, the concentration of the monomer is selected from the group consisting of about 0.5%, about 0.75%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, and about 95% by weight. In some embodiments, the concentration of the monomer is about 0.5% by weight to about 70% by weight. In some embodiments, the concentration of the monomer is about 2% by weight to about 60% by weight. In some embodiments, the concentration of the monomer is about 0.5% by weight to about 40% by weight. In some embodiments, the concentration of the monomer is about 2% by weight to about 30% by weight.

In some embodiments, the methods disclosed herein further comprise applying a catalyst to the keratin-containing material sample. In some embodiments, the catalyst is selected from the group consisting of an amine, a phosphine, and a radical initiator.

In some embodiments, the catalyst is an amine. In some embodiments, the catalyst is a primary amine or a secondary amine. In some embodiments, the catalyst is a tertiary amine. In some embodiments, the amine is selected from the group consisting of N,N-diisopropylethylamine, N-ethyldiisopropylamine, di-n-propylamine, trimethylamine, triethylamine, ethanolamine, diethanolamine, and triethanolamine. In some embodiments, the amine is di-n-propylamine or triethylamine. In some embodiments, the amine is triethylamine.

In some embodiments, the catalyst is a phosphine. In some embodiments, the catalyst is a tertiary phosphine. In some embodiments, the phosphine is selected from the group consisting of dimethylphenylphosphine, diethylphenylphosphine, methyldiphenyl-phosphine, ethyldiphenylphosphine, trimethylphosphine, tripropylphosphine, triphenylphosphine, tri(o-tolyl)phosphine, tri(p-tolyl)phosphine, tris(2,4,6-trimethylphenyl)-phospine, tris(3,5-dimethylphenyl)phospine, dicyclohexyl-(2,6-diisopropylphenyl)phosphine, and tris(hydroxymethyl)phosphine. In some embodiments, the phosphine is dimethylphenylphosphine.

In some embodiments, the amount of the catalyst is about 0.1 mol % to about 100 mol % relative to the thiol compound. In some embodiments, the amount of the catalyst is about 1 mol % to about 100 mol % relative to the thiol compound. In some embodiments, the amount of the catalyst is selected from the group consisting of about 1 mol %, about 2 mol %, about 3 mol %, about 4 mol %, about 5 mol %, about 6 mol %, about 7 mol %, about 8 mol %, about 9 mol %, about 10 mol %, 11 mol %, about 12 mol %, about 13 mol %, about 14 mol %, about 15 mol %, about 16 mol %, about 17 mol %, about 18 mol %, about 19 mol %, about 20 mol %, 21 mol %, about 22 mol %, about 23 mol %, about 24 mol %, about 25 mol %, about 26 mol %, about 27 mol %, about 28 mol %, about 29 mol %, about 30 mol %, 31 mol %, about 32 mol %, about 33 mol %, about 34 mol %, about 35 mol %, about 36 mol %, about 37 mol %, about 38 mol %, about 39 mol %, about 40 mol %, 41 mol %, about 42 mol %, about 43 mol %, about 44 mol %, about 45 mol %, about 46 mol %, about 47 mol %, about 48 mol %, about 49 mol %, about 50 mol %, 51 mol %, about 52 mol %, about 53 mol %, about 54 mol %, about 55 mol %, about 56 mol %, about 57 mol %, about 58 mol %, about 59 mol %, about 60 mol %, 61 mol %, about 62 mol %, about 63 mol %, about 64 mol %, about 65 mol %, about 66 mol %, about 67 mol %, about 68 mol %, about 69 mol %, about 70 mol %, 71 mol %, about 72 mol %, about 73 mol %, about 74 mol %, about 75 mol %, about 76 mol %, about 77 mol %, about 78 mol %, about 79 mol %, about 80 mol %, 81 mol %, about 82 mol %, about 83 mol %, about 84 mol %, about 85 mol %, about 86 mol %, about 87 mol %, about 88 mol %, about 89 mol %, about 90 mol %, 91 mol %, about 92 mol %, about 93 mol %, about 94 mol %, about 95 mol %, about 96 mol %, about 97 mol %, about 98 mol %, about 99 mol %, and about 100 mol % relative to the thiol compound. In some embodiments, the amount of the catalyst is about 1 mol % to about 75 mol % relative to the thiol compound. In some embodiments, the amount of the catalyst is about 10 mol % to about 60 mol % relative to the thiol compound. In some embodiments, the amount of the catalyst is about 20 mol % to about 50 mol % relative to the thiol compound.

In some embodiments, the concentration of the catalyst is about 0.1% by weight to about 15% by weight. In some embodiments, the concentration of the catalyst is selected from the group consisting of about 0.1%, about 0.2%, about 0.3%, about 0.4%, about 0.5%, about 0.6%, about 0.7%, about 0.8%, about 0.9%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, and about 15% by weight. In some embodiments, the concentration of the catalyst is about 0.1% by weight to about 10% by weight. In some embodiments, the concentration of the catalyst is about 0.1% by weight to about 5% by weight. In some embodiments, the concentration of the catalyst is about 1% by weight to about 9% by weight.

In some embodiments of the methods disclosed herein, the catalyst is a radical initiator. In some embodiments, the radical initiator is selected from the group consisting of a peroxide, an azo compound, a photoinitiator. In some embodiments, the radical initiator is a peroxide. In some embodiments, the peroxide is selected from the group consisting of hydrogen peroxide, tert-butyl hydroperoxide, tert-butyl peracetate, cumene hydroperoxide, dicumyl peroxide, benzoyl peroxide, and tert-butyl peroxide. In some embodiments, the peroxide is hydrogen peroxide.

In some embodiments, the radical initiator is an azo compound. In some embodiments, the azo compound is selected from the group consisting of 4,4'-azobis(4-cyanovaleric acid), 4,4'-azobis(4-cyanovaleric acid), 1,1'-azobis(cyclohexanecarbonitrile), 2,2'-azobis(2-methylpropionamidine) dihydrochloride, 2,2'-azobis(2-methylpropionitrile), and 2,2'-azobis(2-methylpropionitrile).

In some embodiments, the radical initiator is a photoinitiator. In some embodiments, the photoinitiator is an aryl ketone. In some embodiments, the photoinitiator is selected from the group consisting of acetophenone; anisoin; anthraquinone; anthroquinone-2-sulfonic acid; benzil; bezoin; benzoin ethyl ether; bezoin isobutyl ether; benzoin methyl ether; benzophenone; 3,3',4,4'-benzophenonetetracarboxylic dianhydride; 4-benzoylbiphenyl; 2-benzyl-2-(dimethylamino)-4'-morpholinobutyrophenone; 4,4'-bis(diethylamino)benzophen-one; 4,4'-bis(dimethylamino)benzophenone; camphorquinone; 2-chlorothioxanthen-2-one; dibenzosuberenone; 2,2'-diethoxyacetophenone; 4,4'-dihydroxybenzophenone; 2,2'-dmethoxy-2-phenylacetophenone; 4-(dimethylamino)benzophenone; 4,4'-dimethylbenzil; 2,5-dimethylbenzophenone; 3,4-dimethylbenzophenone; 2-hydroxy-2-methylpropiophenone; 4'-ethoxyacetophenone; 2-ethylantrhaquinone; 3'-hydroxyacetophenone; 4'-hydroxyaceto-phenone; 3-hydroxyacetophenone; 4-hydroxyacetophenone; 1-hydroxycyclohexyl phenyl ketone; 2-hydroxy-2-methylpropiophenone; 2-methylbenzophenone; 3-methylbenzophenone; methylbenzoylformate; 2-methyl-4'-(methylthio)2-morpholinopropiophenone; phenantrenequinone; 4'-phenyoxyacetophenone; thioxanthen-9-one; and diphenyl(2,4,6-trimethyl-benzoyl)phosphine oxide. In some embodiments, the photoinitiator is 2,2'-diethoxyacetophenone.

In some embodiments of the methods disclosed herein, the mixture further comprises an oxidizing agent. In some embodiments, the oxidizing agent is a peroxide. In some embodiments, the peroxide is selected from the group consisting of hydrogen peroxide, tert-butyl hydroperoxide, tert-butyl peracetate, cumene hydroperoxide, dicumyl peroxide, benzoyl peroxide, and tert-butyl peroxide. In some embodiments, the peroxide is hydrogen peroxide.

In some embodiments, the concentration of the oxidizing agent is about 0.1% by weight to about 15% by weight. In some embodiments, the concentration of the catalyst is selected from the group consisting of about 0.1%, about 0.2%, about 0.3%, about 0.4%, about 0.5%, about 0.6%, about 0.7%, about 0.8%, about 0.9%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, and about 15% by weight. In some embodiments, the concentration of the oxidizing agent is about 0.1% by weight to about 11% by weight. In some embodiments, the concentration of the oxidizing agent is about 0.1% by weight to about 5% by weight. In some embodiments, the concentration of the oxidizing agent is about 0.5% by weight to about 5% by weight. In some embodiments, the concentration of the oxidizing agent is about 1% by weight to about 4% by weight. In some embodiments, the concentration of the oxidizing agent is about 2.5% by weight. In some embodiments, the concentration of the oxidizing agent is about 2.4% by weight. In some embodiments, the concentration of the oxidizing agent is about 5% by weight.

In some embodiments of the methods disclosed herein, the mixture further comprises a solvent. In some embodiments, the solvent comprises dimethyl sulfoxide, water, acetone, buffer, or a mixture thereof. In some embodiments, the solvent is benign. In some embodiments, the solvent is not an organic solvent. In some embodiments, the solvent comprises water. In some embodiments, the solvent is water.

In some embodiments, the thiol-Michael addition grafting reactions on a keratin-containing material proceed faster and with better overall conversion in water, as compared to grafting in organic solvent. This behavior is consistent with a type of biphasic reaction known as "on-water." Certain organic reactions perform optimally on water, even when the organic reactants are insoluble in the aqueous phase.

Figure 6:
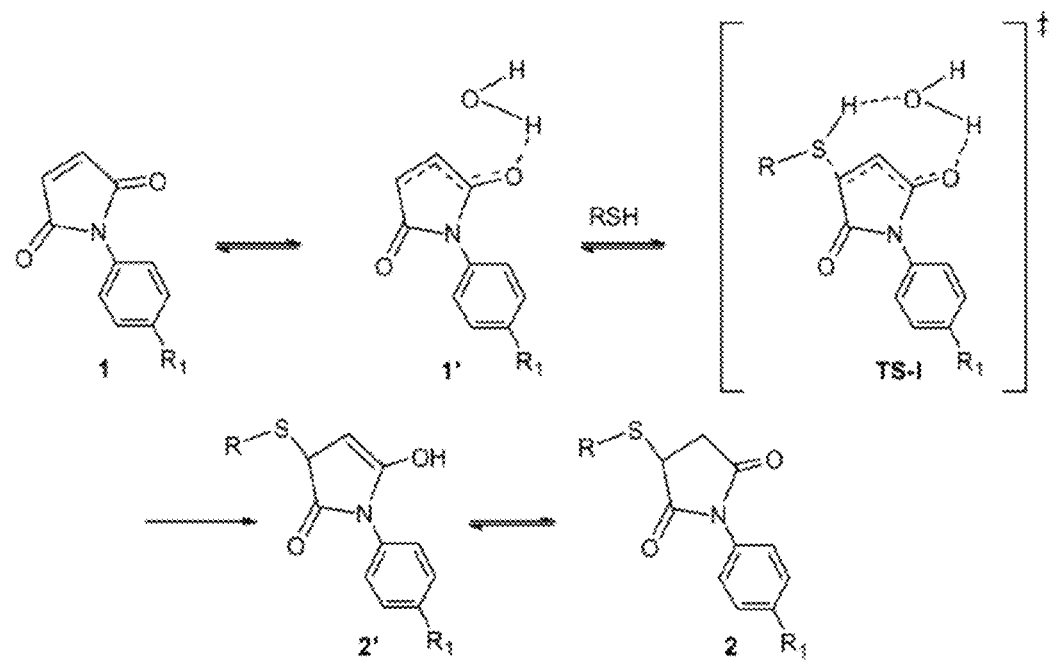
FIG. 6 is a schematic representation of the proposed mechanism for on-water activation in the thiol-Michael system.

Without being bound by any theory, this phenomenon may arise from water's ability to activate both the electrophile and nucleophile through hydrogen bonding. In some embodiments, the proposed mechanism for on-water activation in the thiol-Michael system is shown in FIG. 6.

In some embodiments, the mixture is an emulsion. In some embodiments, the mixture further comprises a surfactant.

Exemplary Properties of a Keratin-Containing Material

In some embodiments, a keratin-containing material is damaged in response to one or more stresses. In some embodiments, the one or more stresses are selected from the group consisting of washing, drying, brushing, combing, rubbing, styling, bleaching, dyeing, sun exposure, heat treatment, and chemical services. For example, hair chemical services include permanent waving (perming), straightening, relaxing, and smoothing.

In some embodiments of the methods disclosed herein, the thiol compound is selected from the group consisting of a monothiol compound, a protected thiol compound, a dithiol compound, a trithiol compound, a tetrathiol compound, and a thiomer. In some embodiments of the methods disclosed herein, the thiol compound comprises at least one free thiol group and at least one additional functional group. In some embodiments, the thiol compound comprises a thioether group and a thiol protecting group to form a protected thiol compound. In some embodiments, under the conditions of the methods, the protected thiol group is unmasked to form a thiol compound comprising a free thiol group.

In another aspect, the disclosure provides a method for treating a keratin-containing material, wherein a denaturation temperature of a keratin-containing material is improved, comprising:
  i) providing a keratin-containing material sample comprising a plurality of disulfide bonds; and
  ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds;
thereby improving the denaturation temperature of the keratin-containing material.

In another aspect, the disclosure provides a method for treating a keratin-containing material, wherein a denaturation temperature of the keratin-containing material is improved, comprising:
  i) providing a keratin-containing material sample comprising a plurality of disulfide bonds; and
  ii) applying to the keratin-containing material sample for a period of time a mixture, comprising one or more thiol compounds, wherein each thiol compound comprises at least one free thiol group and at least one additional functional group; and an oxidizing agent, thereby producing a cross-linked keratin-containing material sample, wherein the cross-linked keratin-containing material sample comprises a plurality of disulfide bonds between the keratin-containing material sample and the thiol compounds;
thereby improving the denaturation temperature of the keratin-containing material.

In another aspect, the disclosure provides a method for treating a keratin-containing material, wherein a denaturation temperature of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
  iii) applying an oxidizing agent, thereby producing a cross-linked keratin-containing material sample, wherein the cross-linked keratin-containing material sample comprises a plurality of disulfide bonds between the keratin-containing material sample and the thiol compounds;
thereby improving the denaturation temperature of the keratin-containing material.

In another aspect, the disclosure provides a method for treating a keratin-containing material, wherein a denaturation temperature of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least one free thiol group and at least one additional functional group, thereby producing a functionalized keratin-containing material sample, wherein the functionalized keratin-containing material sample comprises a plurality of free functional groups; and
  iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;
thereby improving the denaturation temperature of the keratin-containing material.

In another aspect, the disclosure provides a method for treating a keratin-containing material, wherein a denaturation temperature of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
  iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;
thereby improving the denaturation temperature of the keratin-containing material.

In another aspect, the disclosure provides a method for treating a keratin-containing material, wherein a denaturation temperature of the keratin-containing material is improved, comprising:
  i) providing a keratin-containing material sample comprising a plurality of disulfide bonds; and
  ii) applying to the keratin-containing material sample for a period of time a mixture, comprising one or more thiol compounds, wherein each thiol compound comprises at least two free thiol groups; and an oxidizing agent, thereby producing a cross-linked keratin-containing material sample, wherein the cross-linked keratin-containing material sample comprises a plurality of disulfide bonds between the keratin-containing material sample and the thiol compounds;
thereby improving the denaturation temperature of the keratin-containing material.

In another aspect, the disclosure provides a method for treating a keratin-containing material, wherein a denaturation temperature of the keratin-containing material is improved, comprising:
- i) providing a keratin-containing material sample comprising a plurality of disulfide bonds;
- ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
- iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the denaturation temperature of the keratin-containing material.

In another aspect, the disclosure provides a method for treating a keratin-containing material, wherein a denaturation temperature of the keratin-containing material is improved, comprising:
- i) providing a keratin-containing material sample comprising a plurality of disulfide bonds;
- ii) applying to the keratin-containing material sample for a period of time a mixture, comprising one or more thiol compounds, wherein each thiol compound comprises at least two free thiol groups, thereby producing a thiol keratin-containing material sample, wherein the thiol keratin-containing material sample comprises a plurality of free thiol groups; and
- iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the denaturation temperature of the keratin-containing material.

In another aspect, the disclosure provides a method for treating keratin-containing material, wherein a denaturation temperature of the keratin-containing material is improved, comprising:
- i) providing a keratin-containing material sample comprising a plurality of disulfide bonds;
- ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
- iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the denaturation temperature of the keratin-containing material.

In another aspect, the disclosure provides a method for treating keratin-containing material, wherein a denaturation temperature of the keratin-containing material is improved, comprising:
- i) providing a keratin-containing material sample comprising a plurality of disulfide bonds;
- ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds; and
- iii) applying to the keratin-containing material sample for a period of time an additive;

thereby improving the denaturation temperature of the keratin-containing material.

In another aspect, the disclosure provides a method for treating keratin-containing material, wherein a denaturation temperature of the keratin-containing material is improved, comprising:
- i) providing a keratin-containing material sample comprising a plurality of disulfide bonds;
- ii) applying to the keratin-containing material sample for a period of time a first mixture, comprising a first thiol compound;
- iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds; and
- iv) applying to the keratin-containing material sample for a period of time an additive;

thereby improving the denaturation temperature of the keratin-containing material.

In another aspect, the disclosure provides a method for treating keratin-containing material, wherein a denaturation temperature of the keratin-containing material is improved, comprising:
- i) providing a keratin-containing material sample comprising a plurality of disulfide bonds;
- ii) applying to the keratin-containing material sample for a period of time a mixture, comprising one or more thiol compounds, thereby producing a covalently bonded keratin-containing material sample, wherein the covalently bonded keratin-containing material sample comprises a plurality of disulfide bonds between the keratin-containing material sample and the thiol compounds;
- iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
- iv) applying to the keratin-containing material sample for a period of time an additive;

thereby improving the denaturation temperature of the keratin-containing material.

In another aspect, the disclosure provides a method for treating keratin-containing material, wherein a denaturation temperature of the keratin-containing material is improved, comprising:
i) providing a keratin-containing material sample comprising a plurality of disulfide bonds;
ii) applying to the keratin-containing material sample for a period of time a first mixture, comprising a first thiol compound;
iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds;
iv) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
v) applying to the keratin-containing material sample for a period of time an additive;

thereby improving the denaturation temperature of the keratin-containing material.

In some embodiments, the denaturation temperature of the keratin-containing material is used to evaluate the strength and the structural integrity of the material. For example, after chemical treatments such as bleaching, perming, or straightening, keratin-containing materials become damaged. Damaged materials are correlated with decreased denaturation temperatures.

In another aspect, the disclosure provides a method for treating a keratin-containing material, wherein a protein loss value of a keratin-containing material is improved, comprising:
i) providing a keratin-containing material sample comprising a plurality of disulfide bonds; and
ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds;

thereby improving the protein loss value of the keratin-containing material.

In another aspect, the disclosure provides a method for treating a keratin-containing material, wherein a protein loss value of the keratin-containing material is improved, comprising:
i) providing a keratin-containing material sample comprising a plurality of disulfide bonds; and
ii) applying to the keratin-containing material sample for a period of time a mixture, comprising one or more thiol compounds, wherein each thiol compound comprises at least one free thiol group and at least one additional functional group; and an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the protein loss value of the keratin-containing material.

In another aspect, the disclosure provides a method for treating a keratin-containing material, wherein a protein loss value of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the protein loss value of the keratin-containing material.

In another aspect, the disclosure provides a method for treating a keratin-containing material, wherein a protein loss value of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least one free thiol group and at least one additional functional group, thereby producing a functionalized keratin-containing material sample, wherein the functionalized keratin-containing material sample comprises a plurality of free functional groups; and
iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;

thereby improving the protein loss value of the keratin-containing material.

In another aspect, the disclosure provides a method for treating a keratin-containing material, wherein a protein loss value of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;

thereby improving the protein loss value of the keratin-containing material.

In another aspect, the disclosure provides a method for treating a keratin-containing material, wherein a protein loss value of the keratin-containing material is improved, comprising:
  i) providing a keratin-containing material sample comprising a plurality of disulfide bonds; and
  ii) applying to the keratin-containing material sample for a period of time a mixture, comprising one or more thiol compounds, wherein each thiol compound comprises at least two free thiol groups; and an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the protein loss value of the keratin-containing material.

In another aspect, the disclosure provides a method for treating a keratin-containing material, wherein a protein loss value of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
  iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the protein loss value of the keratin-containing material.

In another aspect, the disclosure provides a method for treating a keratin-containing material, wherein a protein loss value of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least two free thiol groups, thereby producing a thiol keratin-containing material sample, wherein the thiol keratin-containing material sample comprises a plurality of free thiol groups; and
  iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the protein loss value of the keratin-containing material.

In another aspect, the disclosure provides a method for treating a keratin-containing material, wherein a protein loss value of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
  iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the protein loss value of the keratin-containing material.

In another aspect, the disclosure provides a method for treating keratin-containing material, wherein a protein loss value of the keratin-containing material is improved, comprising:
  i) providing a keratin-containing material sample comprising a plurality of disulfide bonds;
  ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds; and
  iii) applying to the keratin-containing material sample for a period of time an additive;

thereby improving the protein loss value of the keratin-containing material.

In another aspect, the disclosure provides a method for treating keratin-containing material, wherein a protein loss value of the keratin-containing material is improved, comprising:
  i) providing a keratin-containing material sample comprising a plurality of disulfide bonds;
  ii) applying to the keratin-containing material sample for a period of time a first mixture, comprising a first thiol compound;
  iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds; and
  iv) applying to the keratin-containing material sample for a period of time an additive;

thereby improving the protein loss value of the keratin-containing material.

In another aspect, the disclosure provides a method for treating keratin-containing material, wherein a protein loss value of the keratin-containing material is improved, comprising:

i) providing a keratin-containing material sample comprising a plurality of disulfide bonds;
ii) applying to the keratin-containing material sample for a period of time a mixture, comprising one or more thiol compounds, thereby producing a covalently bonded keratin-containing material sample, wherein the covalently bonded keratin-containing material sample comprises a plurality of disulfide bonds between the keratin-containing material sample and the thiol compounds;
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
iv) applying to the keratin-containing material sample for a period of time an additive;
thereby improving the protein loss value of the keratin-containing material.

In another aspect, the disclosure provides a method for treating keratin-containing material, wherein a protein loss value of the keratin-containing material is improved, comprising:
i) providing a keratin-containing material sample comprising a plurality of disulfide bonds;
ii) applying to the keratin-containing material sample for a period of time a first mixture, comprising a first thiol compound;
iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds;
iv) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
v) applying to the keratin-containing material sample for a period of time an additive;
thereby improving the protein loss value of the keratin-containing material.

In some embodiments, the protein loss value of the keratin-containing material is used to evaluate the strength and the structural integrity of the material. For example, after chemical treatments such as bleaching, perming, or straightening, keratin-containing materials become damaged, which results in higher protein loss. A higher protein loss value is correlated with more damage and less structural integrity.

In another aspect, the disclosure provides a method for treating a keratin-containing material, wherein an elongation at break of the keratin-containing material is improved, comprising:
i) providing a keratin-containing material sample comprising a plurality of disulfide bonds; and
ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds;
thereby improving the elongation at break of the keratin-containing material.

In another aspect, the disclosure provides a method for treating a keratin-containing material, wherein an elongation at break of the keratin-containing material is improved, comprising:
i) providing a keratin-containing material sample comprising a plurality of disulfide bonds; and
ii) applying to the keratin-containing material sample for a period of time a mixture, comprising one or more thiol compounds, wherein each thiol compound comprises at least one free thiol group and at least one additional functional group; and an oxidizing agent, thereby producing a cross-linked keratin-containing material sample, wherein the cross-linked keratin-containing material sample comprises a plurality of disulfide bonds between the keratin-containing material sample and the thiol compounds;
thereby improving the elongation at break of the keratin-containing material.

In another aspect, the disclosure provides a method for treating a keratin-containing material, wherein an elongation at break of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
iii) applying an oxidizing agent, thereby producing a cross-linked keratin-containing material sample, wherein the cross-linked keratin-containing material sample comprises a plurality of disulfide bonds between the keratin-containing material sample and the thiol compounds;
thereby improving the elongation at break of the keratin-containing material.

In another aspect, the disclosure provides a method for treating a keratin-containing material, wherein an elongation at break of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least one free thiol group and at least one additional functional group, thereby producing a functionalized keratin-containing material sample, wherein the functionalized keratin-containing material sample comprises a plurality of free functional groups; and
iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;

thereby improving the elongation at break of the keratin-containing material.

In another aspect, the disclosure provides a method for treating a keratin-containing material, wherein an elongation at break of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;

thereby improving the elongation at break of the keratin-containing material.

In another aspect, the disclosure provides a method for treating a keratin-containing material, wherein an elongation at break of the keratin-containing material is improved, comprising:
i) providing a keratin-containing material sample comprising a plurality of disulfide bonds; and
ii) applying to the keratin-containing material sample for a period of time a mixture, comprising one or more thiol compounds, wherein each thiol compound comprises at least two free thiol groups; and an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the elongation at break of the keratin-containing material.

In another aspect, the disclosure provides a method for treating a keratin-containing material, wherein an elongation at break of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the elongation at break of the keratin-containing material.

In another aspect, the disclosure provides a method for treating a keratin-containing material, wherein an elongation at break of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups, thereby producing a thiol keratin-containing material sample, wherein the thiol keratin-containing material sample comprises a plurality of free thiol groups; and
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the elongation at break of the keratin-containing material.

In another aspect, the disclosure provides a method for treating keratin-containing material, wherein elongation at break of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the elongation at break of the keratin-containing material.

In another aspect, the disclosure provides a method for treating keratin-containing material, wherein an elongation at break of the keratin-containing material is improved, comprising:
i) providing a keratin-containing material sample comprising a plurality of disulfide bonds;
ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds; and
iii) applying to the keratin-containing material sample for a period of time an additive;

thereby improving the elongation at break of the keratin-containing material.

In another aspect, the disclosure provides a method for treating keratin-containing material, wherein an elongation at break of the keratin-containing material is improved, comprising:
- i) providing a keratin-containing material sample comprising a plurality of disulfide bonds;
- ii) applying to the keratin-containing material sample for a period of time a first mixture, comprising a first thiol compound;
- iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds; and
- iv) applying to the keratin-containing material sample for a period of time an additive;

thereby improving the elongation at break of the keratin-containing material.

In another aspect, the disclosure provides a method for treating keratin-containing material, wherein an elongation at break of the keratin-containing material is improved, comprising:
- i) providing a keratin-containing material sample comprising a plurality of disulfide bonds;
- ii) applying to the keratin-containing material sample for a period of time a mixture, comprising one or more thiol compounds, thereby producing a covalently bonded keratin-containing material sample, wherein the covalently bonded keratin-containing material sample comprises a plurality of disulfide bonds between the keratin-containing material sample and the thiol compounds;
- iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
- iv) applying to the keratin-containing material sample for a period of time an additive;

thereby improving the elongation at break of the keratin-containing material.

In another aspect, the disclosure provides a method for treating keratin-containing material, wherein an elongation at break of the keratin-containing material is improved, comprising:
- i) providing a keratin-containing material sample comprising a plurality of disulfide bonds;
- ii) applying to the keratin-containing material sample for a period of time a first mixture, comprising a first thiol compound;
- iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds;
- iv) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
- v) applying to the keratin-containing material sample for a period of time an additive;

thereby improving the elongation at break of the keratin-containing material.

In some embodiments, the elongation at break of the keratin-containing material is used to evaluate the strength of the material. Stronger materials can withstand more stress and strain. Stronger materials can be elongated further before breaking.

In another aspect, the disclosure provides a method for treating a keratin-containing material, wherein a Young's modulus of the keratin-containing material is improved, comprising:
- i) providing a keratin-containing material sample comprising a plurality of disulfide bonds; and
- ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds;

thereby improving the Young's modulus of the keratin-containing material.

In another aspect, the disclosure provides a method for treating a keratin-containing material, wherein a Young's modulus of the keratin-containing material is improved, comprising:
- i) providing a keratin-containing material sample comprising a plurality of disulfide bonds; and
- ii) applying to the keratin-containing material sample for a period of time a mixture, comprising one or more thiol compounds, wherein each thiol compound comprises at least one free thiol group and at least one additional functional group; and an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the Young's modulus of the keratin-containing material.

In another aspect, the disclosure provides a method for treating a keratin-containing material, wherein a Young's modulus of the keratin-containing material is improved, comprising:
- i) providing a keratin-containing material sample comprising a plurality of disulfide bonds;
- ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
- iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the Young's modulus of the keratin-containing material.

In another aspect, the disclosure provides a method for treating a keratin-containing material, wherein a Young's modulus of the keratin-containing material is improved, comprising:
 i) providing a keratin-containing material sample comprising a plurality of disulfide bonds;
 ii) applying to the keratin-containing material sample for a period of time a mixture, comprising one or more thiol compounds, wherein each thiol compound comprises at least one free thiol group and at least one additional functional group, thereby producing a functionalized keratin-containing material sample, wherein the functionalized keratin-containing material sample comprises a plurality of free functional groups; and
 iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;
thereby improving the Young's modulus of the keratin-containing material.

In another aspect, the disclosure provides a method for treating a keratin-containing material, wherein a Young's modulus of the keratin-containing material is improved, comprising:
 i) providing a keratin-containing material sample comprising a plurality of disulfide bonds;
 ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
 iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;
thereby improving the Young's modulus of the keratin-containing material.

In another aspect, the disclosure provides a method for treating a keratin-containing material, wherein a Young's modulus of the keratin-containing material is improved, comprising:
 i) providing a keratin-containing material sample comprising a plurality of disulfide bonds; and
 ii) applying to the keratin-containing material sample for a period of time a mixture, comprising one or more thiol compounds, wherein each thiol compound comprises at least two free thiol groups; and an oxidizing agent, thereby producing a cross-linked keratin-containing material sample, wherein the cross-linked keratin-containing material sample comprises a plurality of disulfide bonds between the keratin-containing material sample and the thiol compounds;
thereby improving the Young's modulus of the keratin-containing material.

In another aspect, the disclosure provides a method for treating a keratin-containing material, wherein a Young's modulus of the keratin-containing material is improved, comprising:
 i) providing a keratin-containing material sample comprising a plurality of disulfide bonds;
 ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
 iii) applying an oxidizing agent, thereby producing a cross-linked keratin-containing material sample, wherein the cross-linked keratin-containing material sample comprises a plurality of disulfide bonds between the keratin-containing material sample and the thiol compounds;
thereby improving the Young's modulus of the keratin-containing material.

In another aspect, the disclosure provides a method for treating a keratin-containing material, wherein a Young's modulus of the keratin-containing material is improved, comprising:
 i) providing a keratin-containing material sample comprising a plurality of disulfide bonds;
 ii) applying to the keratin-containing material sample for a period of time a mixture, comprising one or more thiol compounds, wherein each thiol compound comprises at least two free thiol groups, thereby producing a thiol keratin-containing material sample, wherein the thiol keratin-containing material sample comprises a plurality of free thiol groups; and
 iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;
thereby improving the Young's modulus of the keratin-containing material.

In another aspect, the disclosure provides a method for treating a keratin-containing material, wherein a Young's modulus of the keratin-containing material is improved, comprising:
 i) providing a keratin-containing material sample comprising a plurality of disulfide bonds;
 ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
 iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the Young's modulus of the keratin-containing material.

In another aspect, the disclosure provides a method for treating keratin-containing material, wherein a Young's modulus of the keratin-containing material is improved, comprising:
  i) providing a keratin-containing material sample comprising a plurality of disulfide bonds;
  ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds; and
  iii) applying to the keratin-containing material sample for a period of time an additive;
thereby improving the Young's modulus of the keratin-containing material.

In another aspect, the disclosure provides a method for treating keratin-containing material, wherein a Young's modulus of the keratin-containing material is improved, comprising:
  i) providing a keratin-containing material sample comprising a plurality of disulfide bonds;
  ii) applying to the keratin-containing material sample for a period of time a first mixture, comprising a first thiol compound;
  iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds; and
  iv) applying to the keratin-containing material sample for a period of time an additive;
thereby improving the Young's modulus of the keratin-containing material.

In another aspect, the disclosure provides a method for treating keratin-containing material, wherein a Young's modulus of the keratin-containing material is improved, comprising:
  i) providing a keratin-containing material sample comprising a plurality of disulfide bonds;
  ii) applying to the keratin-containing material sample for a period of time a mixture, comprising one or more thiol compounds, thereby producing a covalently bonded keratin-containing material sample, wherein the covalently bonded keratin-containing material sample comprises a plurality of disulfide bonds between the keratin-containing material sample and the thiol compounds;
  iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
  iv) applying to the keratin-containing material sample for a period of time an additive;
thereby improving the Young's modulus of the keratin-containing material.

In another aspect, the disclosure provides a method for treating keratin-containing material, wherein a Young's modulus of the keratin-containing material is improved, comprising:
  i) providing a keratin-containing material sample comprising a plurality of disulfide bonds;
  ii) applying to the keratin-containing material sample for a period of time a first mixture, comprising a first thiol compound;
  iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds;
  iv) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
  v) applying to the keratin-containing material sample for a period of time an additive;
thereby improving the Young's modulus of the keratin-containing material.

In another aspect, the disclosure provides a method for treating a keratin-containing material, wherein an ultimate tensile strength of the keratin-containing material is improved, comprising:
  i) providing a keratin-containing material sample comprising a plurality of disulfide bonds; and
  ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds;
thereby improving the ultimate tensile strength of the keratin-containing material.

In another aspect, the disclosure provides a method for treating a keratin-containing material, wherein an ultimate tensile strength of the keratin-containing material is improved, comprising:
  i) providing a keratin-containing material sample comprising a plurality of disulfide bonds; and
  ii) applying to the keratin-containing material sample for a period of time a mixture, comprising one or more thiol compounds, wherein each thiol compound comprises at least one free thiol group and at least one additional functional group; and an oxidizing agent, thereby producing a cross-linked keratin-containing material sample, wherein the cross-linked keratin-containing material sample comprises a plurality of disulfide bonds between the keratin-containing material sample and the thiol compounds;
thereby improving the ultimate tensile strength of the keratin-containing material.

In another aspect, the disclosure provides a method for treating a keratin-containing material, wherein an ultimate tensile strength of the keratin-containing material is improved, comprising:

i) providing a keratin-containing material sample comprising a plurality of disulfide bonds;
ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the ultimate tensile strength of the keratin-containing material.

In another aspect, the disclosure provides a method for treating a keratin-containing material, wherein an ultimate tensile strength of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least one free thiol group and at least one additional functional group, thereby producing a functionalized keratin-containing material sample, wherein the functionalized keratin-containing material sample comprises a plurality of free functional groups; and
iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;

thereby improving the ultimate tensile strength of the keratin-containing material.

In another aspect, the disclosure provides a method for treating a keratin-containing material, wherein an ultimate tensile strength of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;

thereby improving the ultimate tensile strength of the keratin-containing material.

In another aspect, the disclosure provides a method for treating a keratin-containing material, wherein an ultimate tensile strength of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups; and an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the ultimate tensile strength of the keratin-containing material.

In another aspect, the disclosure provides a method for treating a keratin-containing material, wherein an ultimate tensile strength of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the ultimate tensile strength of the keratin-containing material.

In another aspect, the disclosure provides a method for treating a keratin-containing material, wherein an ultimate tensile strength of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups, thereby producing a thiol keratin-containing material sample, wherein the thiol keratin-containing material sample comprises a plurality of free thiol groups; and
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the ultimate tensile strength of the keratin-containing material.

In another aspect, the disclosure provides a method for treating a keratin-containing material, wherein an ultimate tensile strength of the keratin-containing material is improved, comprising:

i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the ultimate tensile strength of the keratin-containing material.

In another aspect, the disclosure provides a method for treating keratin-containing material, wherein an ultimate tensile strength of the keratin-containing material is improved, comprising:
i) providing a keratin-containing material sample comprising a plurality of disulfide bonds;
ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds; and
iii) applying to the keratin-containing material sample for a period of time an additive;

thereby improving the ultimate tensile strength of the keratin-containing material.

In another aspect, the disclosure provides a method for treating keratin-containing material, wherein an ultimate tensile strength of the keratin-containing material is improved, comprising:
i) providing a keratin-containing material sample comprising a plurality of disulfide bonds;
ii) applying to the keratin-containing material sample for a period of time a first mixture, comprising a first thiol compound;
iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds; and
iv) applying to the keratin-containing material sample for a period of time an additive;

thereby improving the ultimate tensile strength of the keratin-containing material.

In another aspect, the disclosure provides a method for treating keratin-containing material, wherein an ultimate tensile strength of the keratin-containing material is improved, comprising:
i) providing a keratin-containing material sample comprising a plurality of disulfide bonds;
ii) applying to the keratin-containing material sample for a period of time a mixture, comprising one or more thiol compounds, thereby producing a covalently bonded keratin-containing material sample, wherein the covalently bonded keratin-containing material sample comprises a plurality of disulfide bonds between the keratin-containing material sample and the thiol compounds;
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
iv) applying to the keratin-containing material sample for a period of time an additive;

thereby improving the ultimate tensile strength of the keratin-containing material.

In another aspect, the disclosure provides a method for treating keratin-containing material, wherein an ultimate tensile strength of the keratin-containing material is improved, comprising:
i) providing a keratin-containing material sample comprising a plurality of disulfide bonds;
ii) applying to the keratin-containing material sample for a period of time a first mixture, comprising a first thiol compound;
iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds;
iv) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
v) applying to the keratin-containing material sample for a period of time an additive;

thereby improving the ultimate tensile strength of the keratin-containing material.

In some embodiments, the ultimate tensile strength of the keratin-containing material is used to evaluate the structural integrity of the material. Ultimate tensile strength is the capacity of a material to withstand loads tending to elongate the material.

In another aspect, the disclosure provides a method for treating a keratin-containing material, wherein hydrophobicity of a keratin-containing material is improved, comprising:
i) providing a keratin-containing material sample comprising a plurality of disulfide bonds; and
ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds;

thereby improving the hydrophobicity of the keratin-containing material.

In another aspect, the disclosure provides a method for treating a keratin-containing material, wherein hydrophobicity of the keratin-containing material is improved, comprising:
- i) providing a keratin-containing material sample comprising a plurality of disulfide bonds; and
- ii) applying to the keratin-containing material sample for a period of time a mixture, comprising one or more thiol compounds, wherein each thiol compound comprises at least one free thiol group and at least one additional functional group; and an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the hydrophobicity of the keratin-containing material.

In another aspect, the disclosure provides a method for treating a keratin-containing material, wherein hydrophobicity of the keratin-containing material is improved, comprising:
- i) providing a keratin-containing material sample comprising a plurality of disulfide bonds;
- ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
- iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the hydrophobicity of the keratin-containing material.

In another aspect, the disclosure provides a method for treating a keratin-containing material, wherein hydrophobicity of the keratin-containing material is improved, comprising:
- i) providing a keratin-containing material sample comprising a plurality of disulfide bonds;
- ii) applying to the keratin-containing material sample for a period of time a mixture, comprising one or more thiol compounds, wherein each thiol compound comprises at least one free thiol group and at least one additional functional group, thereby producing a functionalized keratin-containing material sample, wherein the functionalized keratin-containing material sample comprises a plurality of free functional groups; and
- iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;

thereby improving the hydrophobicity of the keratin-containing material.

In another aspect, the disclosure provides a method for treating a keratin-containing material, wherein hydrophobicity of the keratin-containing material is improved, comprising:
- i) providing a keratin-containing material sample comprising a plurality of disulfide bonds;
- ii) applying to the keratin-containing material sample for a period of time a mixture, comprising one or more thiol compounds, wherein each thiol compound comprises at least one free thiol group and at least one additional functional group; and a catalyst, thereby producing a functionalized keratin-containing material sample, wherein the functionalized keratin-containing material sample comprises a plurality of free functional groups; and
- iii) applying a monomer to the functionalized keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free functional groups and the monomers;

thereby improving the hydrophobicity of the keratin-containing material.

In another aspect, the disclosure provides a method for treating a keratin-containing material, wherein hydrophobicity of a keratin-containing material is improved, comprising:
- i) providing a keratin-containing material sample comprising a plurality of disulfide bonds; and
- ii) applying to the keratin-containing material sample for a period of time a mixture, comprising one or more thiol compounds, wherein each thiol compound comprises at least two free thiol groups; and an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the hydrophobicity of the keratin-containing material.

In another aspect, the disclosure provides a method for treating a keratin-containing material, wherein hydrophobicity of a keratin-containing material is improved, comprising:
- i) providing a keratin-containing material sample comprising a plurality of disulfide bonds;
- ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
- iii) applying an oxidizing agent, thereby producing a cross-linked keratin-containing material sample, wherein the cross-linked keratin-containing material sample comprises a plurality of disulfide bonds between the keratin-containing material sample and the thiol compounds;

thereby improving the hydrophobicity of the keratin-containing material.

In another aspect, the disclosure provides a method for treating a keratin-containing material, wherein hydrophobicity of the keratin-containing material is improved, comprising:

i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups, thereby producing a thiol keratin-containing material sample, wherein the thiol keratin-containing material sample comprises a plurality of free thiol groups; and
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the hydrophobicity of the keratin-containing material.

In another aspect, the disclosure provides a method for treating a keratin-containing material, wherein hydrophobicity of the keratin-containing material is improved, comprising:
i) providing a keratin-containing material sample comprising a plurality of disulfide bonds;
ii) applying to the keratin-containing material sample for a period of time a mixture, comprising one or more thiol compounds, wherein each thiol compound comprises at least two free thiol groups; and a catalyst, thereby producing a thiol keratin-containing material sample, wherein the thiol keratin-containing material sample comprises a plurality of free thiol groups; and
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the hydrophobicity of the keratin-containing material.

In another aspect, the disclosure provides a method for treating keratin-containing material, wherein hydrophobicity of the keratin-containing material is improved, comprising:
i) providing a keratin-containing material sample comprising a plurality of disulfide bonds;
ii) applying to the keratin-containing material sample for a period of time a mixture, comprising one or more thiol compounds; and a catalyst, thereby producing a covalently bonded keratin-containing material sample, wherein the covalently bonded keratin-containing material sample comprises a plurality of disulfide bonds between the keratin-containing material sample and the thiol compounds; and
iii) applying to the keratin-containing material sample for a period of time an additive;

thereby improving the hydrophobicity of the keratin-containing material.

In another aspect, the disclosure provides a method for treating keratin-containing material, wherein hydrophobicity of the keratin-containing material is improved, comprising:
i) providing a keratin-containing material sample comprising a plurality of disulfide bonds;
ii) applying to the keratin-containing material sample for a period of time a first mixture, comprising a first thiol compound;
iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds; and
iv) applying to the keratin-containing material sample for a period of time an additive;

thereby improving the hydrophobicity of the keratin-containing material.

In another aspect, the disclosure provides a method for treating keratin-containing material, wherein hydrophobicity of the keratin-containing material is improved, comprising:
i) providing a keratin-containing material sample comprising a plurality of disulfide bonds;
ii) applying to the keratin-containing material sample for a period of time a mixture, comprising one or more thiol compounds, thereby producing a covalently bonded keratin-containing material sample, wherein the covalently bonded keratin-containing material sample comprises a plurality of disulfide bonds between the keratin-containing material sample and the thiol compounds;
iii) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
iv) applying to the keratin-containing material sample for a period of time an additive;

thereby improving the hydrophobicity of the keratin-containing material.

In another aspect, the disclosure provides a method for treating keratin-containing material, wherein hydrophobicity of the keratin-containing material is improved, comprising:
i) providing a keratin-containing material sample comprising a plurality of disulfide bonds;
ii) applying to the keratin-containing material sample for a period of time a first mixture, comprising a first thiol compound;
iii) applying to the keratin-containing material sample for a period of time a second mixture, comprising a second thiol compound; thereby producing a cross-linked keratin-containing material sample, wherein the cross-linked keratin-containing material sample comprises a plurality of covalent bonds between the keratin-containing material sample and the thiol compounds;
iv) applying a monomer to the thiol keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers; and
v) applying to the keratin-containing material sample for a period of time an additive;

thereby improving the hydrophobicity of the keratin-containing material.

In some embodiments of the methods disclosed herein, the method for treating a keratin-containing material improves one or more properties selected from the group consisting of a denaturation temperature, a protein loss value, an elongation at break, a Young's modulus, an ultimate tensile strength, and hydrophobicity of the keratin-containing material.

In some embodiments, the advancing water contact angle is greater than about 70°. In some embodiments, the advancing water contact angle is greater than about 80°. In some embodiments, the advancing water contact angle is greater than about 90°. In some embodiments, the advancing water contact angle is greater than about 100°.

In some embodiments, the advancing water contact angle is selected from the group consisting of about 70°, about 71°, about 72°, about 73°, about 74°, about 75°, about 76°, about 77°, about 78°, about 79°, about 80°, about 81°, about 82°, about 83°, about 84°, about 85°, about 86°, about 87°, about 88°, about 89°, about 90°, about 91°, about 92°, about 93°, about 94°, about 95°, about 96°, about 97°, about 98°, about 99°, about 100°, about 101°, about 102°, about 103°, about 104°, about 105°, about 106°, about 107°, about 108°, about 109°, and about 110°. In some embodiments, the advancing water contact angle is about 100°.

In some embodiments of the methods disclosed herein, the treated keratin-containing material is evaluated by "sensory evaluation". As used herein, "sensory evaluation" refers to comparative sensory evaluations of keratin-containing material samples by people. These people have been trained in sensory evaluations to evaluate tactile (e g, manageability, smoothness, conditioned feeling) and visual properties (e.g., frizz, fiber alignment, and curl shape) of the samples. The evaluation is often side-by-side, that is, comparison of a treated keratin-containing material sample with an untreated or control keratin-containing material sample. In some embodiments, the sensory evaluation is blinded. That is, the evaluator does not know the treatment status of the samples before the evaluation. In some embodiments, the results of the sensory evaluation are categorized as nothing, moderately conditioned, or very product-y. In some embodiments, substantial grafting efficiency correlates to very product-y sensory evaluation results.

In some embodiments, the results of the sensory evaluation are presented as "sensory scores". Typically, treated keratin-containing material samples as well as an untreated or control keratin-containing material sample are prepared in duplicate, blinded randomly, and evaluated for visual, tactile and overall sensory attributes on a scale of −2 to 2 by trained sensory analysts under blinded conditions. Sensory analysts are licensed hair stylists and cosmetic scientists with significant long-term experience evaluating sensory attributes of hair. Sensory analysts assign a score of −2 to tresses deemed entirely undesirable, a score of +2 to entirely soft, natural feeling and appearing hair, and intermediate scores between these two extremes. In some embodiments, the treated keratin-containing material mimics virgin keratin-containing material. In some embodiments, the treated keratin-containing material has similar characteristics to virgin keratin-containing material.

In some embodiments, the keratin-containing material treatment provides a wash-resistant functional (i.e. hydrophobic) layer.

In some embodiments, the treated keratin-containing material is treated hair. In some embodiments, the treated hair mimics the 18-MEA conditioning layer of virgin hair. In some embodiments, the monomer on the treated hair reinstalls a hydrophobic "healthy hair" layer.

In some embodiments, the hair treatment provides a wash-resistant functional (i.e. hydrophobic) layer. In some embodiments, the treated hair has improved alignment. In some embodiments, the treated hair has long-lasting smoothness. In some embodiments, the treated hair has improved shine. For example, hair health can be assessed based on one or more of an elongation at break, a Young's modulus, an ultimate tensile strength, a protein loss value, and a denaturation temperature.

In some embodiments, the treated keratin-containing material is treated nails. In some embodiments, the nails are fingernails or toenails. In some embodiments, the treated nails mimic virgin or new nails. In some embodiments, the treated nails improve flexibility. In some embodiments, the treated nails are less brittle. For example, brittleness can be assessed based on one or more of an elongation at break, a Young's modulus, an ultimate tensile strength, a protein loss value, and a denaturation temperature.

Exemplary Kits

One aspect of the disclosure provides a kit comprising a mixture comprising one or more thiol compounds and a catalyst; and instructions for use.

One aspect of the disclosure provides a kit comprising a mixture comprising one or more thiol compounds and an oxidizing agent; and instructions for use.

One aspect of the disclosure provides a kit comprising a mixture comprising one or more thiol compounds, a catalyst, and an oxidizing agent; and instructions for use. In some embodiments, the oxidizing agent is separate from the other components.

One aspect of the disclosure provides a kit comprising a thiol composition comprising one or more thiol compounds; a monomer composition comprising a monomer; and instructions for use.

One aspect of the disclosure provides a kit comprising a thiol composition comprising one or more thiol compounds; an oxidizing agent composition comprising an oxidizing agent; and instructions for use.

In some embodiments, the thiol composition comprises one or more thiol compounds; and a solvent. In some embodiments, the thiol composition further comprises a catalyst.

In some embodiments, the monomer composition comprises a monomer; and a solvent.

In some embodiments, the oxidizing agent composition comprises an oxidizing agent; and a solvent.

In some embodiments, the solvent comprises dimethyl sulfoxide, water, acetone, buffer, or a mixture thereof. In some embodiments, the solvent comprises water. In some embodiments, the solvent is water.

Another aspect of the disclosure provides a kit comprising a mixture comprising one or more thiol compounds and a catalyst; a monomer composition comprising a monomer; and instructions for use.

In some embodiments of the kits disclosed herein, the thiol compound is in a concentration of about 0.1% by weight to about 15% by weight. In some embodiments, the thiol compound comprises at least two free thiol groups.

In some embodiments of the kits disclosed herein, the monomer is selected from the group consisting of an acrylate, a methacrylate, a monomer comprising a vinyl group, a monomer comprising an alkyne group, and a monomer comprising a maleimide group.

EXEMPLIFICATION

The invention now being generally described, it will be more readily understood by reference to the following, which is included merely for purposes of illustration of certain aspects and embodiments of the present invention, and is not intended to limit the invention.

Example 1—Thiol Delivery

N-Ethylmaleimide Assay

Figure 7:
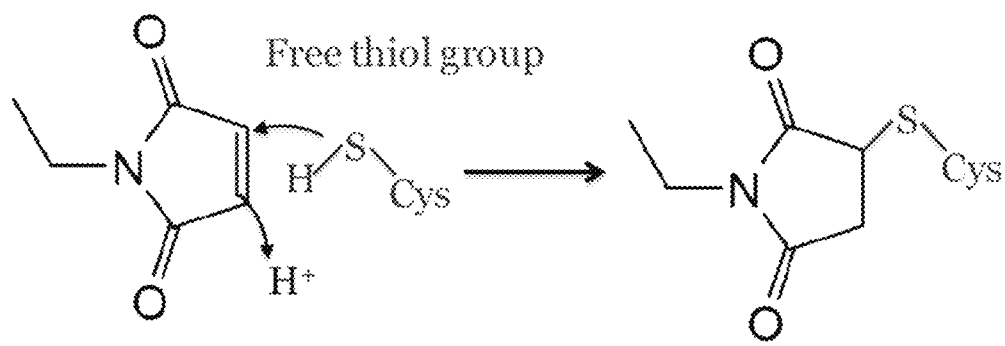
FIG. 7 is a schematic representation of reaction of NEM with free thiol groups to form a stable thioether.

N-ethylmaleimide (NEM) is a reagent that reacts specifically with thiol groups at pH 6.5-7.5 to form stable thioether groups (FIG. 7). Since NEM has a characteristic absorbance peak at 300 nm in its UV-vis spectrum, the reaction was monitored by the decrease in absorbance at 300 nm. NEM is a small molecule and thus able to penetrate through the cuticle into the cortex region. It was expected that NEM assay would provide bulk measurement of thiol content in hair samples. In a typical experiment, a known concentration of NEM was mixed with hair fibers in a phosphate buffered saline (PBS) solution containing 0.1 M phosphate, 0.15 M sodium chloride, at pH 7.2. The level of decrease in NEM concentration was used to quantify free thiol content on hair.

When an experiment was conducted at a pH of 9.5 with 5% by weight of ATG for at a liquor ratio of 5:1, the thiol content was determined to be in the range of 600-800 μmol/g of hair by the NEM assay. This result was very similar to the results obtained using amino acid analysis.[9]

This method also allows for the μmol/mg quantification of free thiol present on other a keratin-containing material.

Exemplary Thiol Delivery Parameters

Certain parameters were varied to achieve exemplary thiol delivery conditions, including liquor ratio, catalyst concentration, thiol compound (e.g., multi-thiol) concentration, reaction time, and pH. Table 1 shows exemplary parameters for the thiol delivery processes using pentaerythritol tetrakis(3-mercaptopropionate) as a model multi-thiol molecule and triethylamine (TEA) as a catalyst. Water was used as the only solvent system for all thiol delivery experiments.

TABLE 1

Exemplary parameters for the thiol delivery process.

| Parameter | Range Investigated | Exemplary Level |
| --- | --- | --- |
| Liquor Ratio | 2:1 to 10:1 | 5:1 |
| Monomer-to-hair thiol Ratio | 1:1 to 2:25 (0.08:1) | 1:1 to 1:2 (0.5:1) |
| Catalyst Concentrations (wrt thiol compound) | 0 mol % to 50 mol % | 20 mol % to 50 mol % |
| Reaction Time | 15-60 minutes | 30 minutes |
| pH | 9.6-11.3 | 10-11 |
| Catalyst-to-Citric Acid Ratio | 0.3:0 to 3:0.6 | 2:0.4 |

Liquor Ratio

The weight ratio of the thiol compound solution to the hair fiber, known in the textile industry as the "liquor ratio," has proven to be an important parameter. A liquor ratio of 5:1 was used for all thiol delivery experiments.

Catalyst Concentration

Figure 8A:
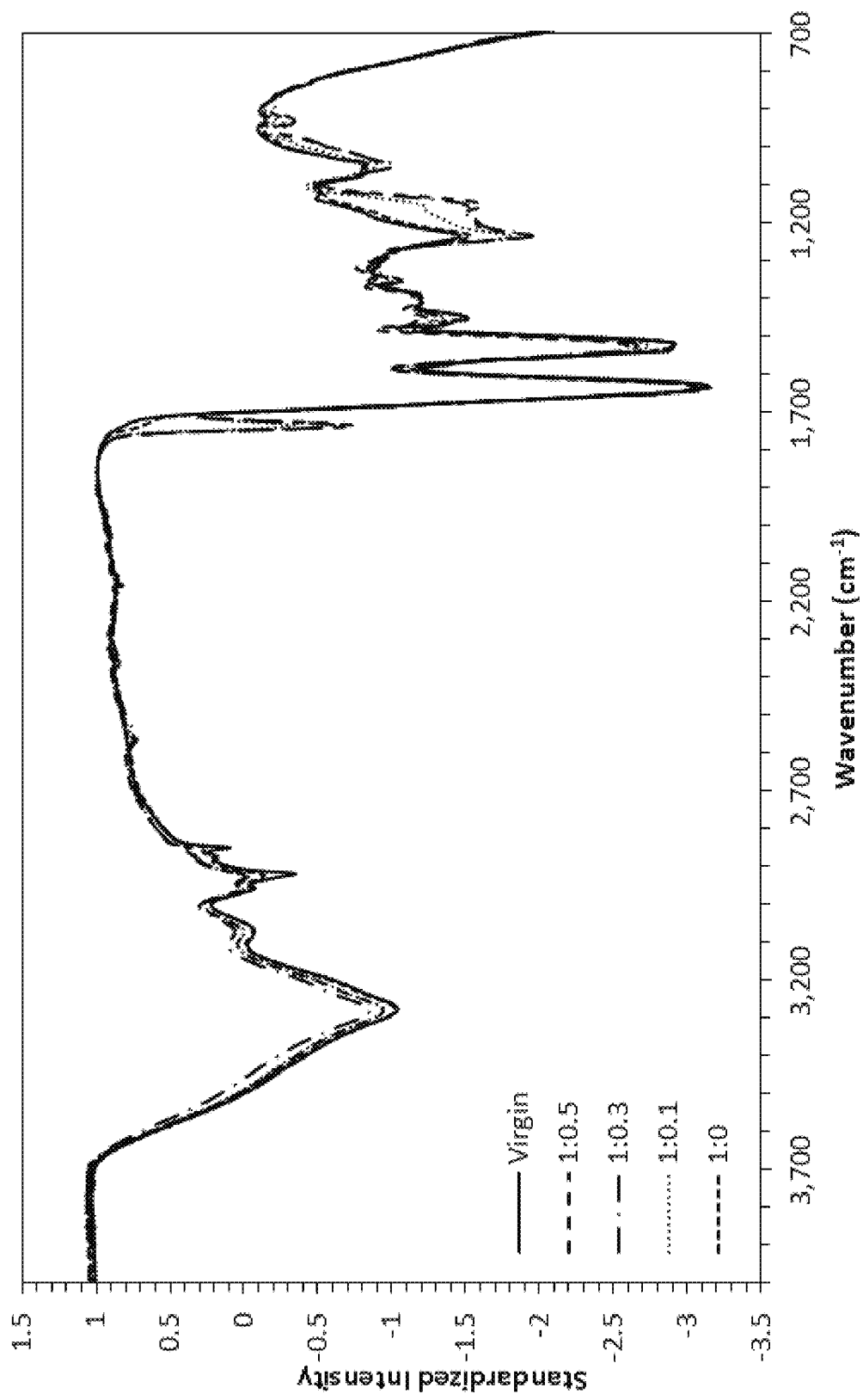
FIG. 8A depicts FTIR spectra of hair after thiol delivery of an exemplary thiol compound at various tertiary amine catalyst ratios.
Figure 8B:
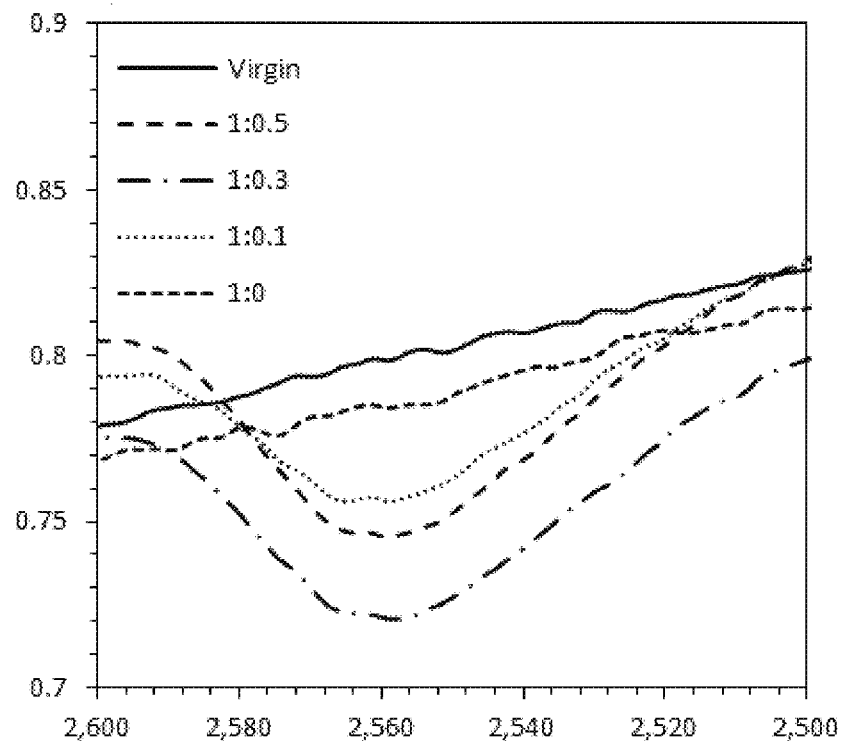
FIG. 8B depicts thiol peak region of FTIR spectra of hair after thiol delivery of an exemplary thiol compound at various tertiary amine catalyst ratios.
Figure 8C:
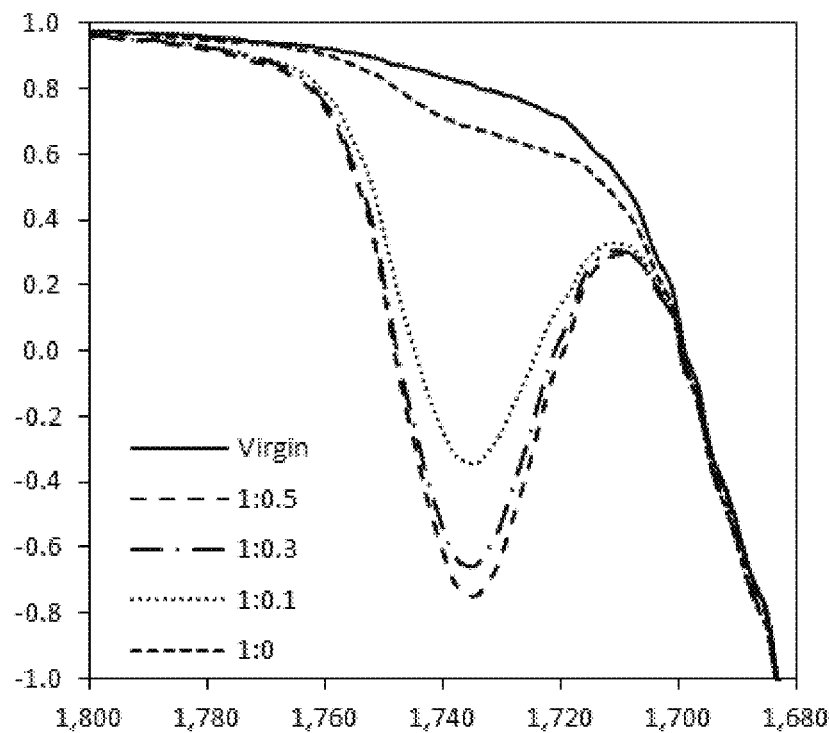
FIG. 8C depicts carbonyl peak region of FTIR spectra of hair after thiol delivery of an exemplary thiol compound at various tertiary amine catalyst ratios.

A tertiary amine, TEA, was used as a catalyst. To study the effect of TEA concentration on thiol delivery efficiency, a range of catalyst concentrations were investigated. The definition of tetrathiol-to-TEA ratios was adapted from experiments, in which all monomer-to-catalyst-to-hair thiol ratios were calculated based on the estimation of ~800 μmol-SH/g thiol content generated by reducing agents like ammonium thioglycolate (ATG). For consistency, the same nomenclature was used in this study. For example, a tetrathiol-to-TEA ratio of 1:0.03 refers to a tetrathiol-to-TEA-to-hair thiol ratio of 1:0.03:1. FIGS. 8A-8C show the FTIR spectra of hair samples treated at various tetrathiol-to-TEA ratios. All experiments were carried out with a constant tetrathiol concentration, only the TEA catalyst concentration was varied from 0, 10, 30, to 50 mol % with respect to the tetrathiol concentration, i.e., tetrathiol-to-TEA ratio from 1:0. 1:0.1, 1:0.3, to 1:0.5. All experiments in the presence of TEA resulted in strong signals in both the thiol (ca. 2560 cm$^{-1}$, FIG. 8B) and the carbonyl (ca. 1735 cm$^{-1}$, FIG. 8C) regions. In contrast, no detectable thiol peak and a very weak carbonyl peak were observed when no TEA was used. An exemplary tetrathiol-to-TEA ratio was 1:0.3, which corresponds to a 30 mol % TEA concentration with respect to tetrathiol. Further increase in the TEA concentration to 50 mol % did not lead to significant change in thiol or carbonyl peak intensity.

Figure 9:
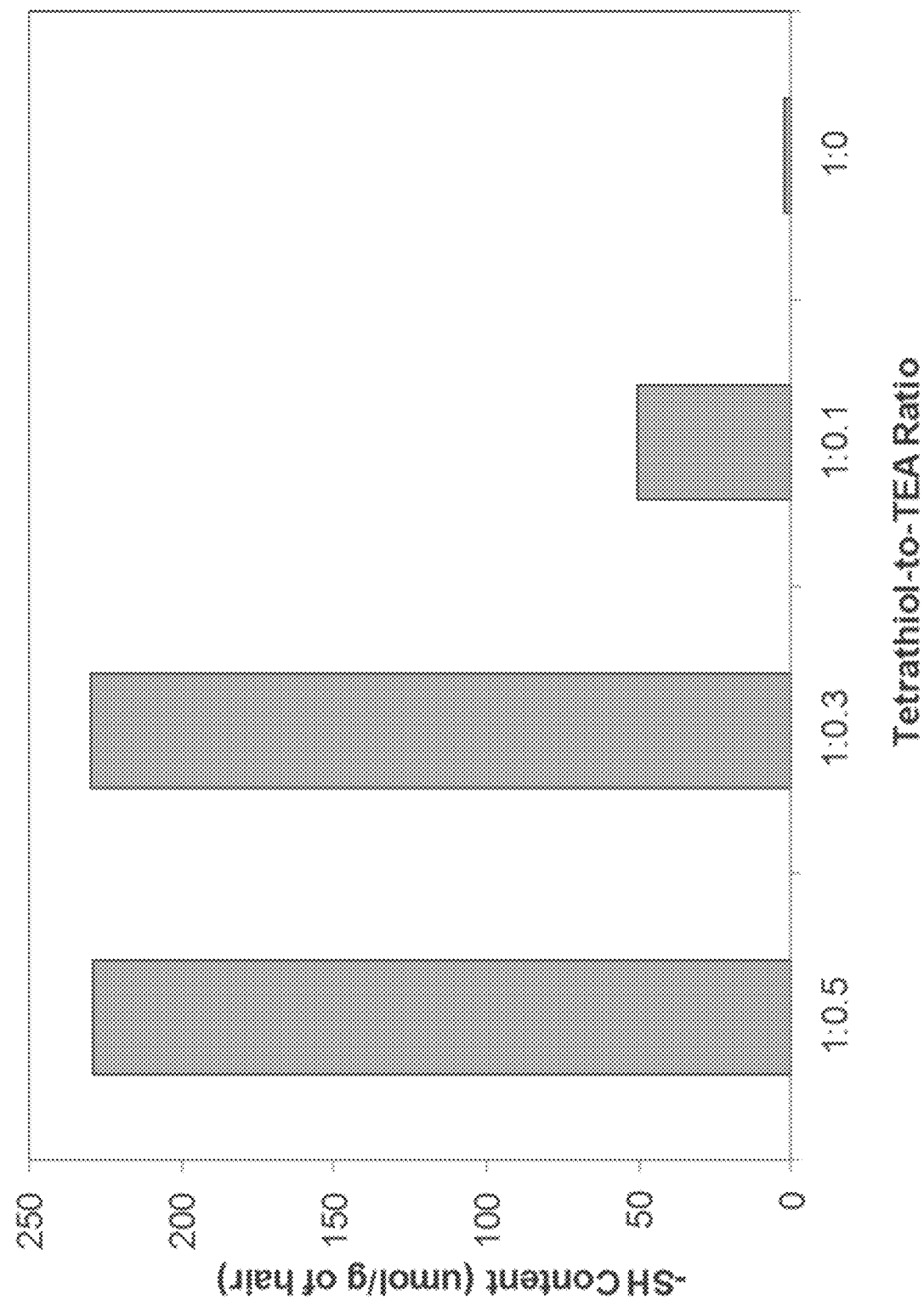
FIG. 9 depicts the free thiol content in hair samples treated at different tetrathiol-to-TEA ratios for 1 h with a constant tetrathiol concentration.

To further quantify the thiol delivery efficiency, an N-ethylmaleimide (NEM) assay was performed to determine free thiol concentrations in hair. FIG. 9 shows free thiol content generated at different tetrathiol-to-TEA ratios. Very similar to the FTIR data, the free thiol content increased with increasing TEA concentration from 10 mol % to 30 mol %, but remained similar at the 50 mol % TEA concentration. When no TEA was used, negligible thiol groups were detected. Both FTIR analysis and the NEM assay, suggested an exemplary tetrathiol-to-TEA ratio of 1:0.3 for good thiol delivery.

Thiol Compound Concentration

Figure 10A:
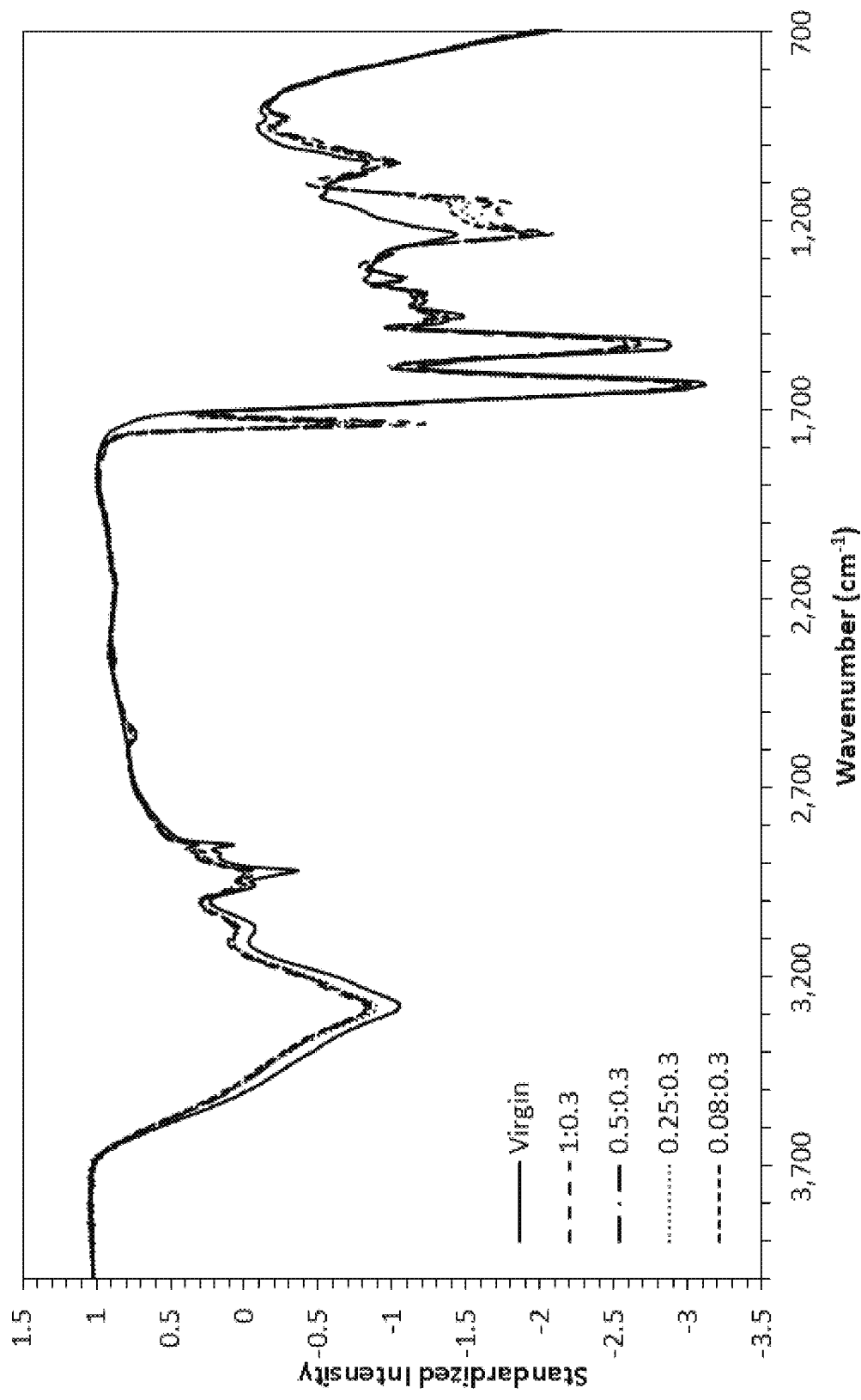
FIG. 10A depicts FTIR spectra of hair after thiol delivery of an exemplary thiol compound at various tetrathiol-to-tertiary amine catalyst ratios for 1 h.
Figure 10B:
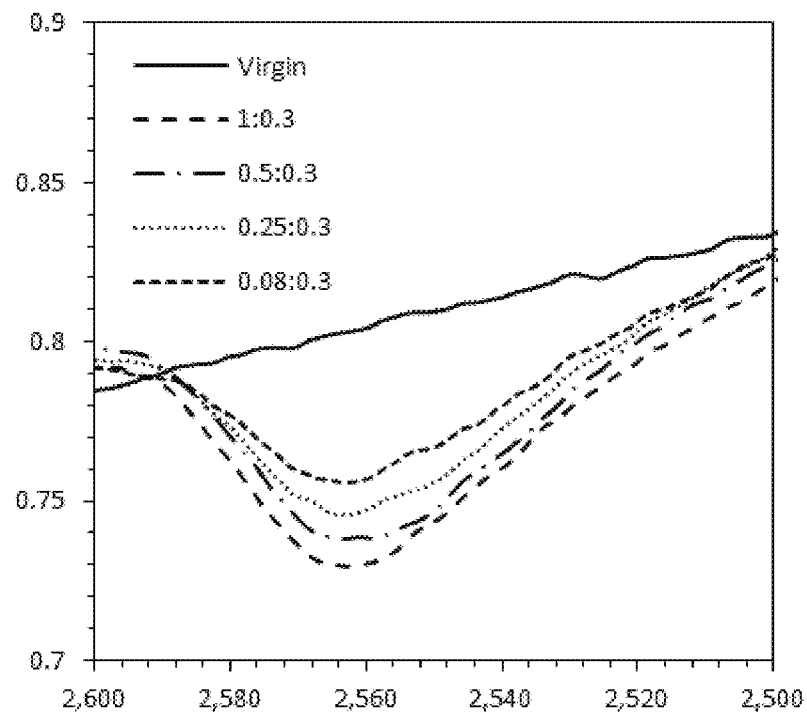
FIG. 10B depicts the thiol peak region of FTIR spectra of hair after thiol delivery of an exemplary thiol compound at various tetrathiol-to-tertiary amine catalyst ratios for 1 h.
Figure 10C:
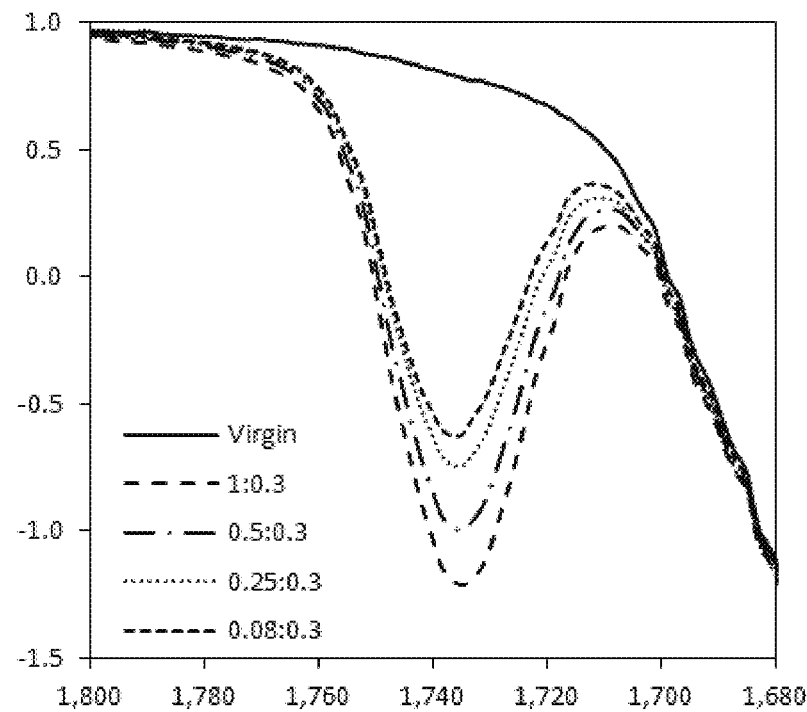
FIG. 10C depicts the carbonyl peak region of FTIR spectra of hair after thiol delivery of an exemplary thiol compound at various tetrathiol-to-tertiary amine catalyst ratios for 1 h.
Figure 11:
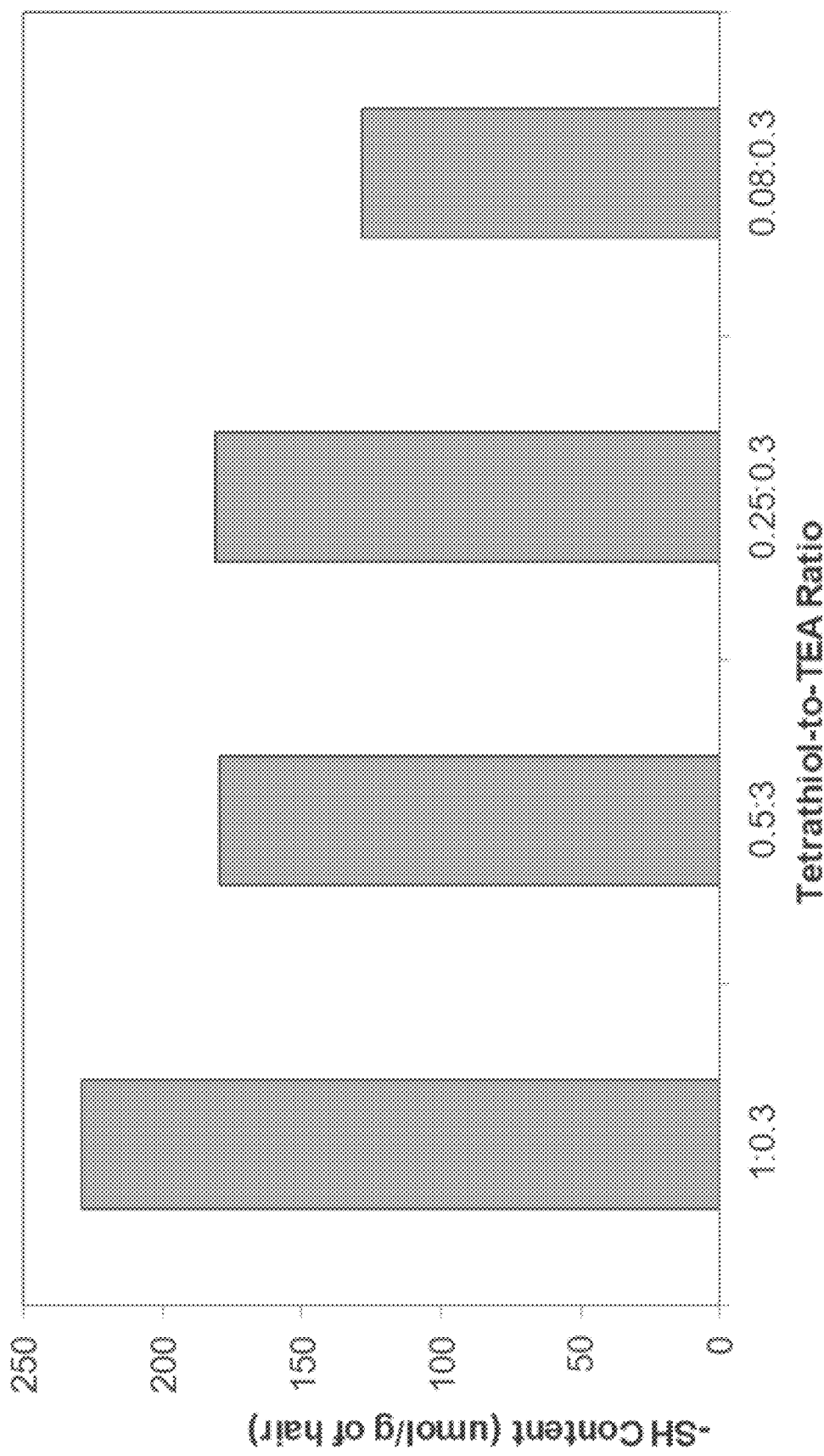
FIG. 11 depicts the free thiol content in hair samples treated at different tetrathiol-to-tertiary amine catalyst ratios for 1 h with a constant tertiary amine catalyst concentration.

Due to commercialization considerations, it was of interest to minimize the thiol compound, here, tetrathiol, concentration. Lower tetrathiol concentrations were used while keeping the TEA concentration constant for all experiments to study the pure effect of tetrathiol concentration on thiol delivery efficiency. FIGS. 10A-10C show the FTIR spectra of hair samples treated at tetrathiol-to-TEA ratios of 1:0.3, 0.5:0.3, 0.25:0.3, and 0.08:0.3. Although a positive dose response relationship was observed, the lowest tetrathiol concentration, i.e., the tetrathiol-to-TEA ratio of 0.08:0.3, still resulted in strong thiol (ca. 2560 cm$^{-1}$, FIG. 10B) and carbonyl (ca. 1735 cm$^{-1}$, FIG. 10C) peaks, suggesting efficient thiol delivery at this low tetrathiol concentration. FIG. 11 shows the NEM assay of hair samples treated at different tetrathiol concentrations. Similar to the FTIR results, the NEM assay showed a positive dose response relationship. However, even at the lowest tetrathiol-to-TEA ratio of 0.08:0.3, a significant amount (~130 μmol/g of hair) of free thiol groups was generated. Experimental results showed that the thiol delivery efficiency remained similar for catalyst concentrations in the range of 20-50 mol %.

Reaction Time

Figure 12A:
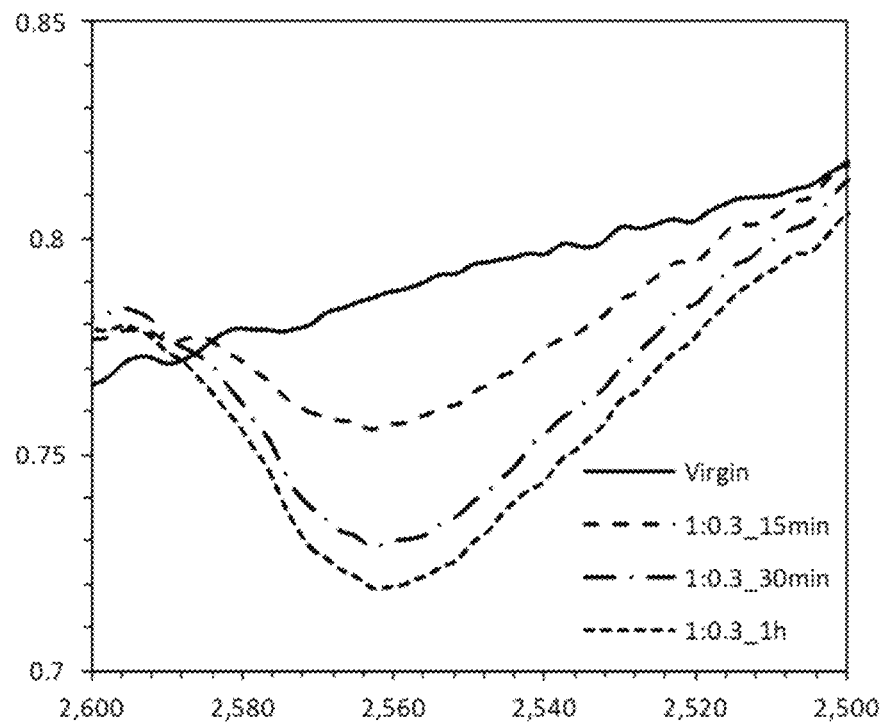
FIG. 12A depicts the thiol peak region of FTIR spectra of hair after thiol delivery of an exemplary thiol compound at a tetrathiol-to-tertiary amine catalyst ratio of 1:0.3 for various reaction times.
Figure 12B:
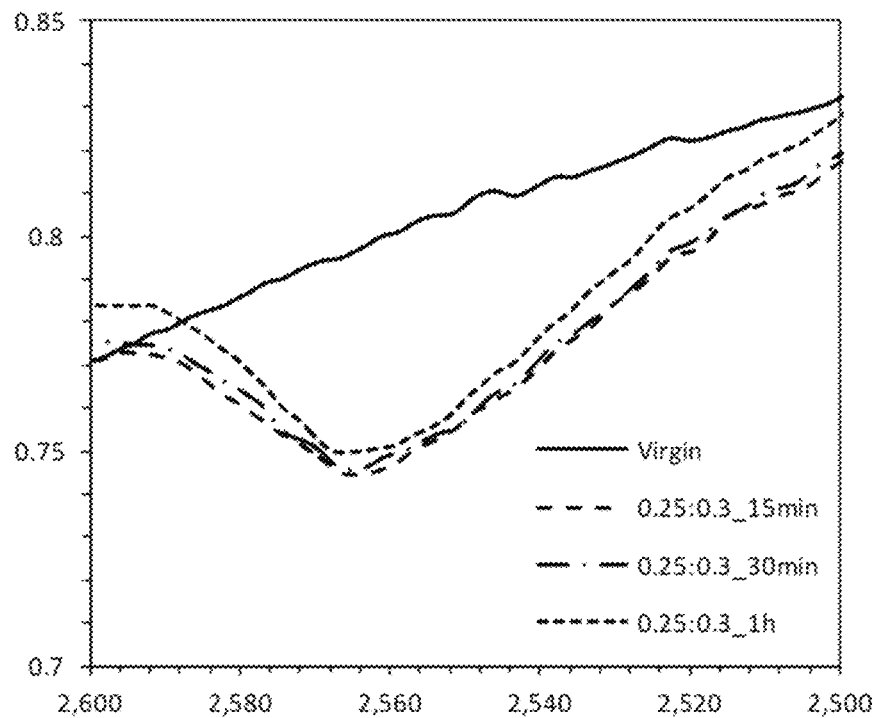
FIG. 12B depicts the thiol peak region of FTIR spectra of hair after thiol delivery of an exemplary thiol compound at a tetrathiol-to-tertiary amine catalyst ratio of 0.25:0.3 for various reaction times.
Figure 12C:
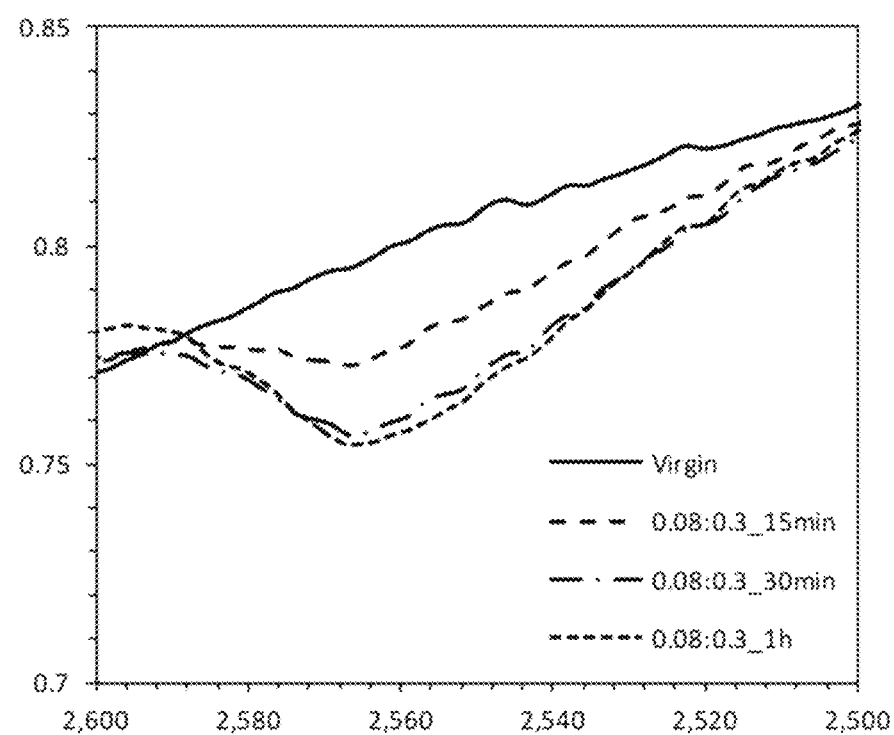
FIG. 12C depicts the thiol peak region of FTIR spectra of hair after thiol delivery of an exemplary thiol compound at a tetrathiol-to-tertiary amine catalyst ratio of 0.08:0.3 for various reaction times.

Different reaction times were also investigated to determine exemplary treatment times. FIGS. 12A-12C show the FTIR spectra in the thiol peak region (2500-2600 cm$^{-1}$) for hair samples treated for 15 min, 30 min, and 1 h at different tetrathiol-to-TEA ratios. The samples of FIG. 12A used a tetrathiol-to-TEA ratio of 1:0.3. The samples of FIG. 12B used a tetrathiol-to-TEA ratio of 0.25:0.3. The samples of FIG. 12C used a tetrathiol-to-TEA ratio of 0.08:0.3. It appeared that at all ratios the thiol peak had reached maximum peak intensity after about 30 min of reaction time. An extension of the reaction time to 1 h did not seem to improve the thiol delivery efficiency. Therefore, an exemplary reaction time for the thiol delivery process was 30 min.

pH of Reaction Mixtures

Figure 13A:
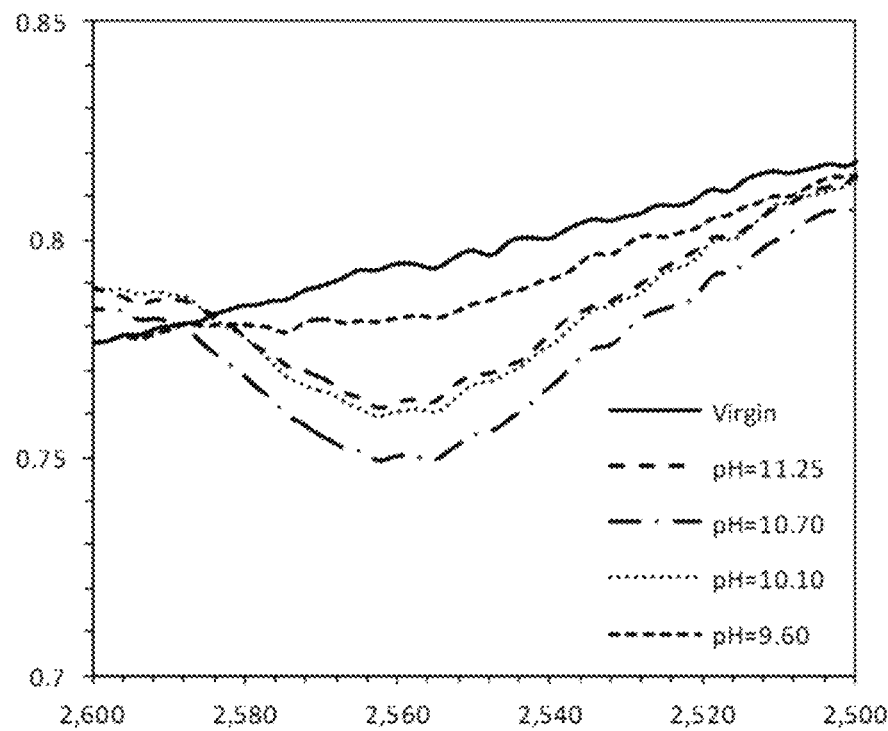
FIG. 13A depicts the thiol peak region of FTIR spectra of hair after thiol delivery of an exemplary thiol compound at various pH values for 1 h.
Figure 13B:
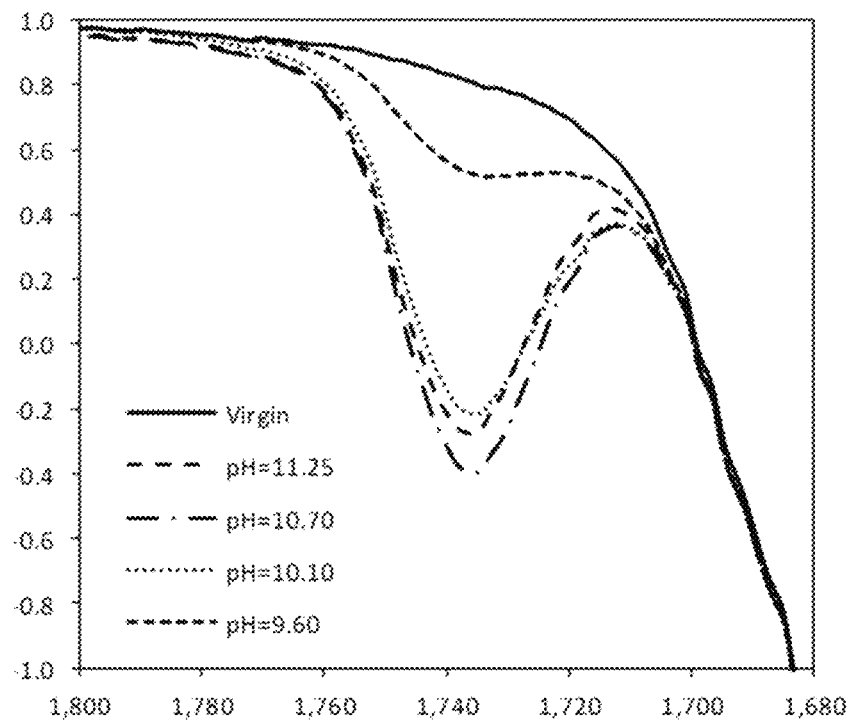
FIG. 13B depicts the carbonyl peak region of FTIR spectra of hair after thiol delivery of an exemplary thiol compound at various pH values for 1 h.

At the lowest tetrathiol-to-TEA ratio of 0.08:0.3, the natural pH for the thiol delivery system is ~11.25. Thiol delivery at lower pH values was explored. FIGS. 13A and 13B show the FTIR spectra of hair samples treated at pH of 11.25, 10.70, 10.10, and 9.60, all adjusted with a 0.5 M citric acid aqueous solution. Interestingly all experiments performed at pH of 10.10 or above showed similar peak intensities in both thiol (FIG. 13A) and carbonyl (FIG. 13B) peak regions. In contrast, only minimum thiol and carbonyl peaks were detected when pH was lowered to 9.60. The results suggested that an exemplary pH for thiol delivery was 10-11.

Citric Acid Concentration

Figure 14A:
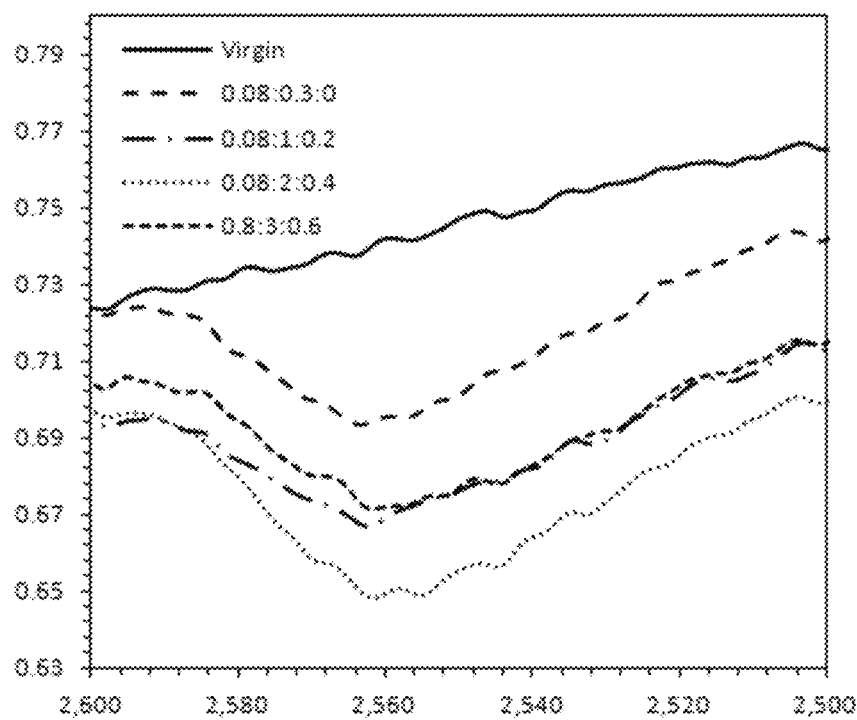
FIG. 14A depicts the thiol peak region of FTIR spectra of hair after thiol delivery of an exemplary thiol compound at various tertathiol-to-tertiary amine catalyst-to-acid ratios for 1 h.
Figure 14B:
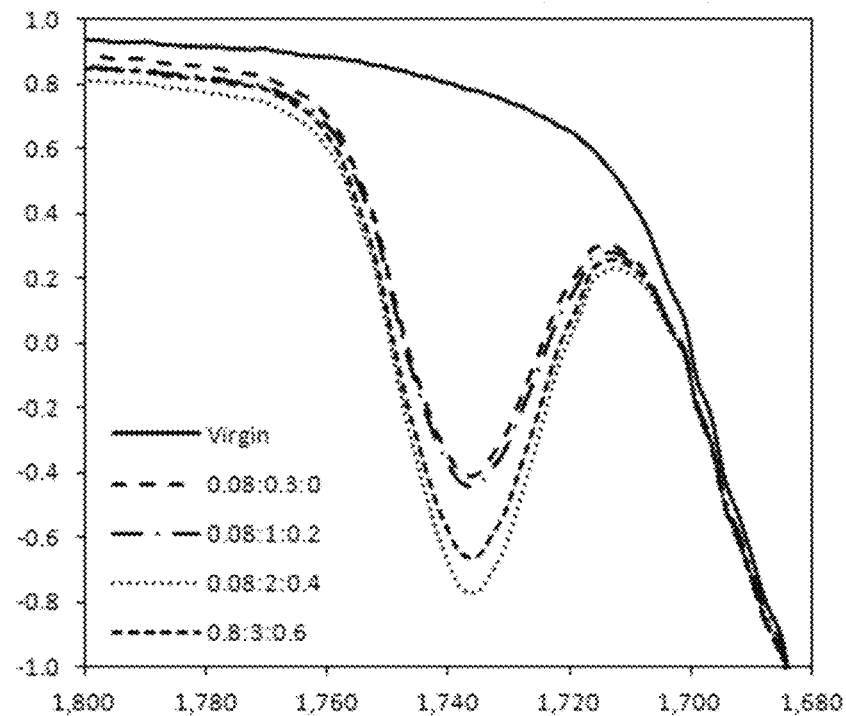
FIG. 14B depicts the carbonyl peak region of FTIR spectra of hair after thiol delivery of an exemplary thiol compound at various tertathiol-to-tertiary amine catalyst-to-acid ratios for 1 h.
Figure 15:
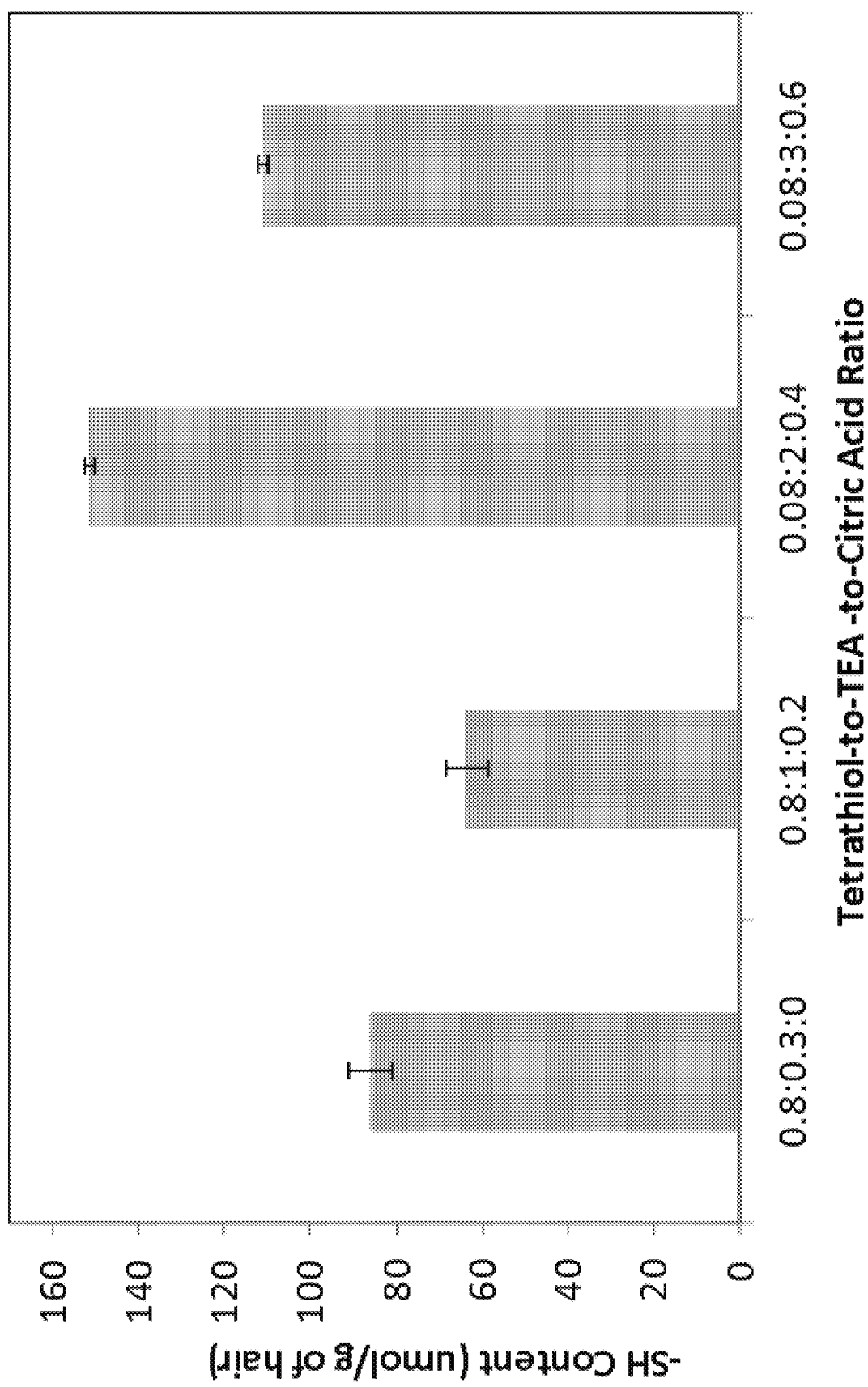
FIG. 15 depicts the free thiol content in hair samples treated at different tertathiol-to-tertiary amine catalyst-to-acid ratios for 1 h.

Preliminary sensory evaluation suggested that presence of citric acid in the reaction mixtures improved the tactile properties of hair treated using the disclosed methods. Thiol delivery at higher citric acid concentrations was explored. To keep pH of the reaction mixtures relatively constant at ~10.1, TEA concentrations were also increased proportionally. FIGS. 14A and 14B show FTIR spectra of hair samples treated at different tetrathiol-to-TEA-to-citric acid ratios for 1 h. It was clear that a tetrathiol-to-TEA-to-citric acid of 0.08:2:0.4 resulted in the strongest thiol and carbonyl peaks, further increase in tetrathiol and TEA concentrations did not lead to higher thiol delivery efficiency. Similar to the FTIR data, data for an NEM assay showed the highest free thiol content in the hair sample treated at a tetrathiol-to-TEA-to-citric acid of 0.08:2:0.4 (FIG. 15). Both FTIR and NEM results suggested that an exemplary tetrathiol-to-TEA-to-citric acid ratio was 0.08:2:0.4 to achieve high thiol delivery efficiency.

Exemplary Thiol Delivery Parameters for Thiomers

Thiomer Concentration

Figure 16:
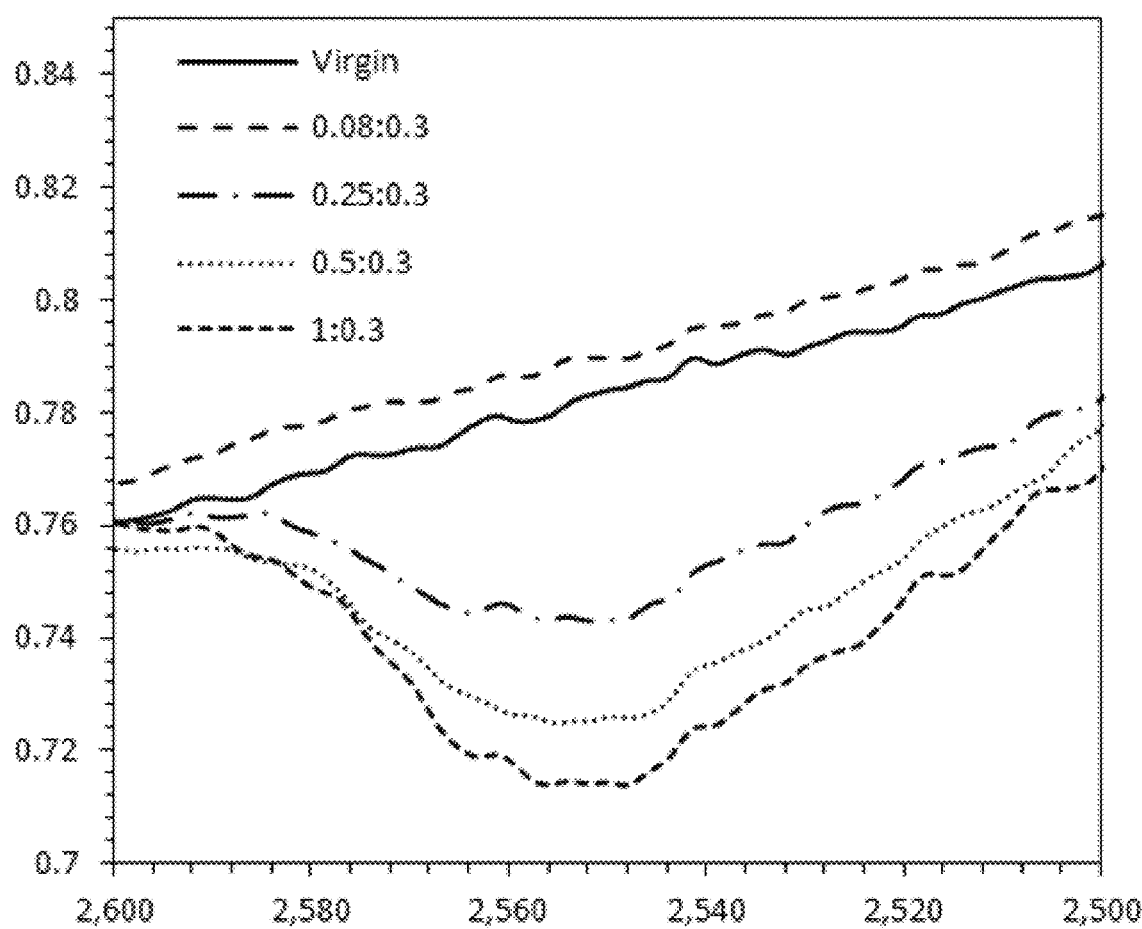
FIG. 16 depicts the thiol peak region of FTIR spectra of hair after thiol delivery of an exemplary thiomer at various thiomer-to-tertiary amine catalyst ratios with a constant tertiary amine catalyst concentration for 1 h.
Figure 17:
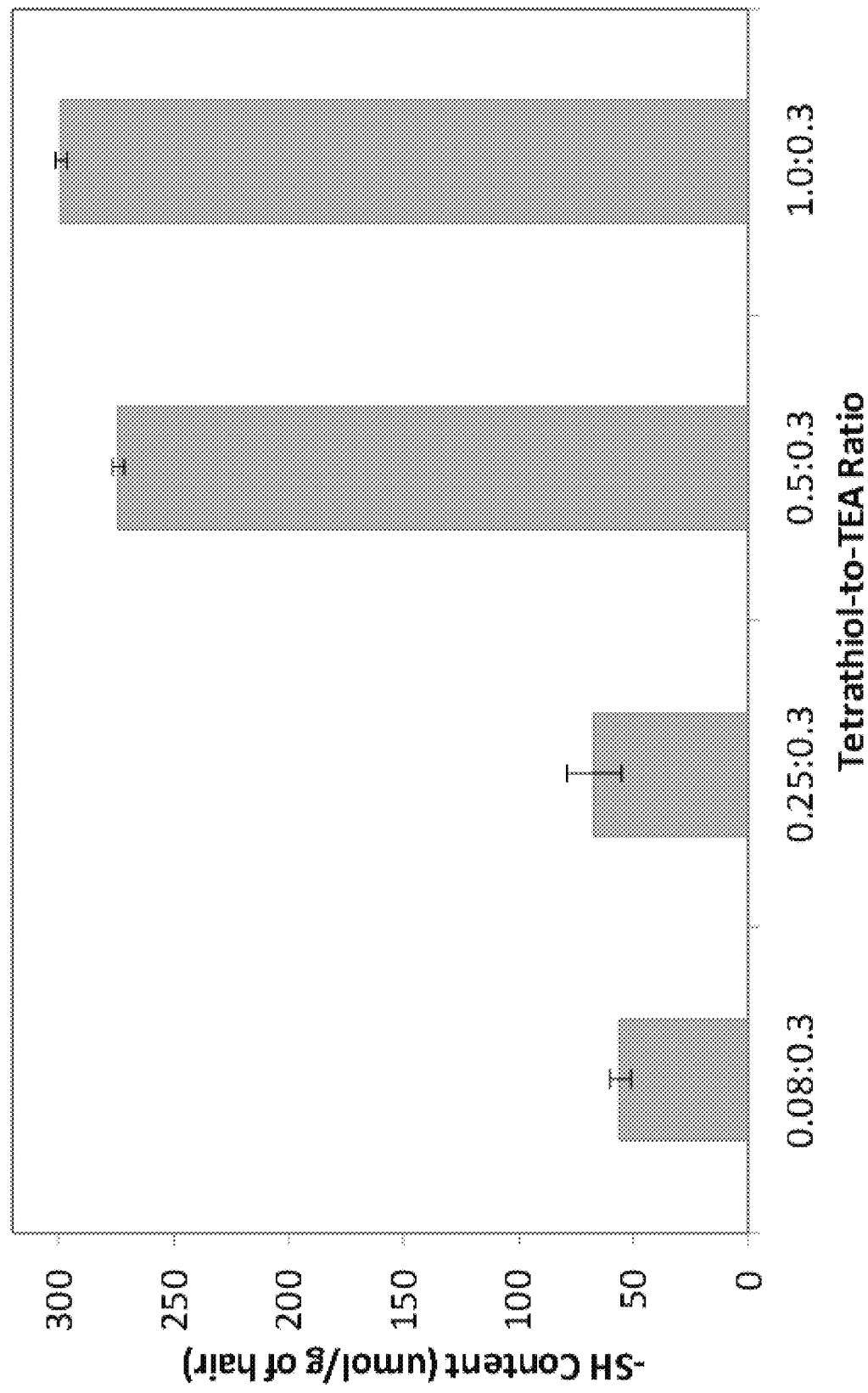
FIG. 17 depicts the free thiol content in hair samples treated at different thiomer-to-tertiary amine catalyst ratios with a constant tertiary amine catalyst concentration for 1 h.

The thiol delivery process using a 4-arm poly(ethylene glycol) thiol with a molecular weight of 2000 Da (4-arm PEG2K-SH) as a model thiomer and triethylamine (TEA) as a catalyst. Water was used as the only solvent system for all thiol delivery experiments. FIG. 16 shows the FTIR spectra thiol region of hair samples treated with 4-arm PEG2K-SH at different thiomer-to-TEA ratios for 1 h. The thiol peak became much stronger as the thiomer-to-TEA ratio was increased from 0.08:0.3 and 0.25:0.3 to 0.5:0.3. However the peak intensity only slightly increased as the thiomer-to-TEA ratio was further increased to 1:0.3. Very similar trends were observed in the NEM analysis, where both the 0.5:0.3 and 1:0.3 thiomer-to-TEA ratios showed similar free thiol contents (FIG. 17). Both FTIR and NEM results suggested that the exemplary thiomer-to-TEA ratio was 0.5:0.3 to achieve high thiol delivery efficiency.

Catalyst Concentration

Figure 18:
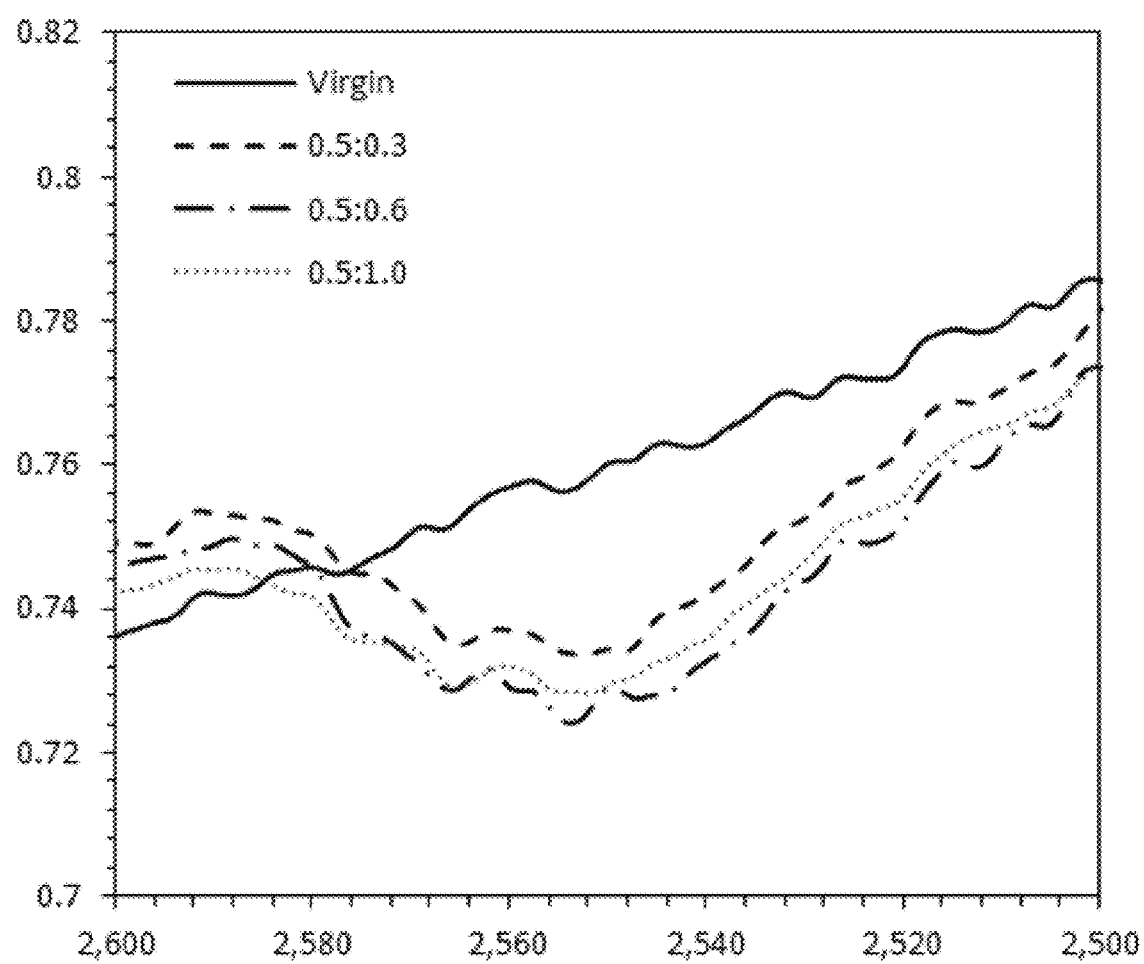
FIG. 18 depicts the thiol peak region of FTIR spectra of hair after thiol delivery of an exemplary thiomer at various thiomer-to-tertiary amine catalyst ratios with a constant thiomer concentration for 1 h.

To study the effect of TEA concentration on 4-arm PEG2K-SH thiomer delivery efficiency, a range of catalyst concentrations were also investigated while keeping a constant thiomer concentration. FIG. 18 shows the FTIR spectra thiol region of hair samples treated at different thiomer-to-TEA ratios of 0.5:0.3, 0.5:0.6, and 0.5:1.0. A slight increase in thiol peak intensity was observed for the two higher TEA concentration samples. The results suggested that the exemplary thiomer-to-TEA ratio was 0.5:0.6 to achieve the high thiol delivery efficiency.

Exemplary Thiol Delivery Parameters on Damaged Hair

In addition to the work performed on virgin hair, the potential of delivering free thiol groups to damaged hair was investigated. The hair damage could occur due to various treatments, such as repetitive heat treatments, bleaching, and coloring. For example, as a result of chemical bleaching disulfide bonds of cystine residues in hair undergo oxidation to form cysteic acid groups. Since disulfide bonds provide mechanical linkages within proteins hair is composed of, degradation of disulfide bonds could lead to degradation of hair proteins and hair damage. In addition, during bleaching process the thioester bonds binding 18-methyl eicosanoic acid to hair may be attacked by the alkaline bleaching reagents resulting in partial removal of this hydrophobic layer rendering hair hydrophilic.[1]

Thiol Delivery on Hair Damaged by Bleaching

Figure 19A:
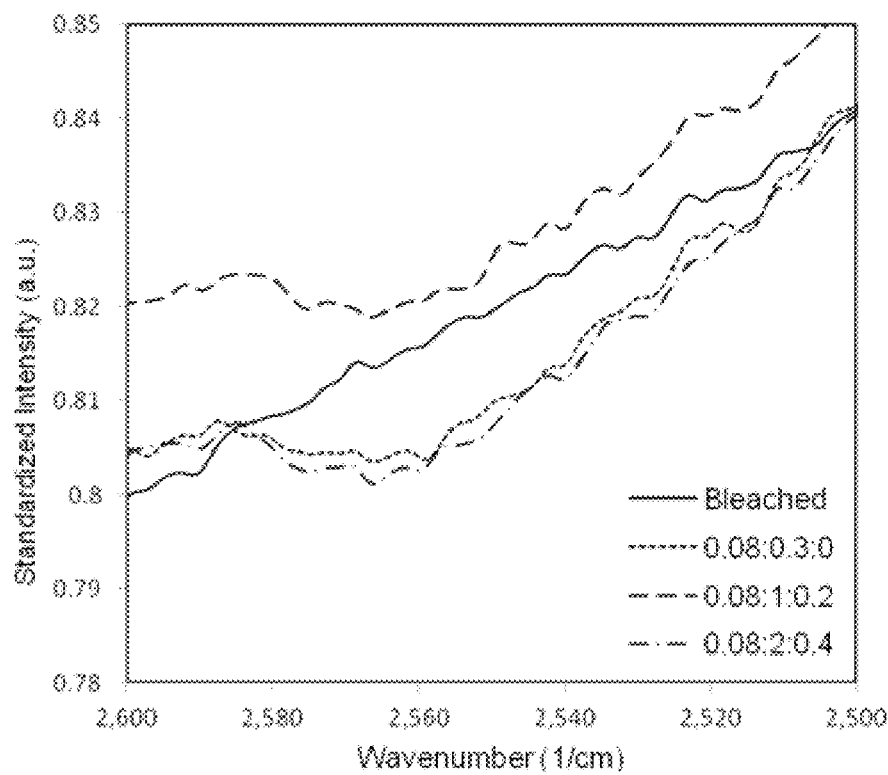
FIG. 19A depicts the thiol peak region of FTIR spectra of hair after thiol delivery on bleached hair of an exemplary thiol compound at various tertathiol-to-tertiary amine catalyst-to-acid ratios.
Figure 19B:
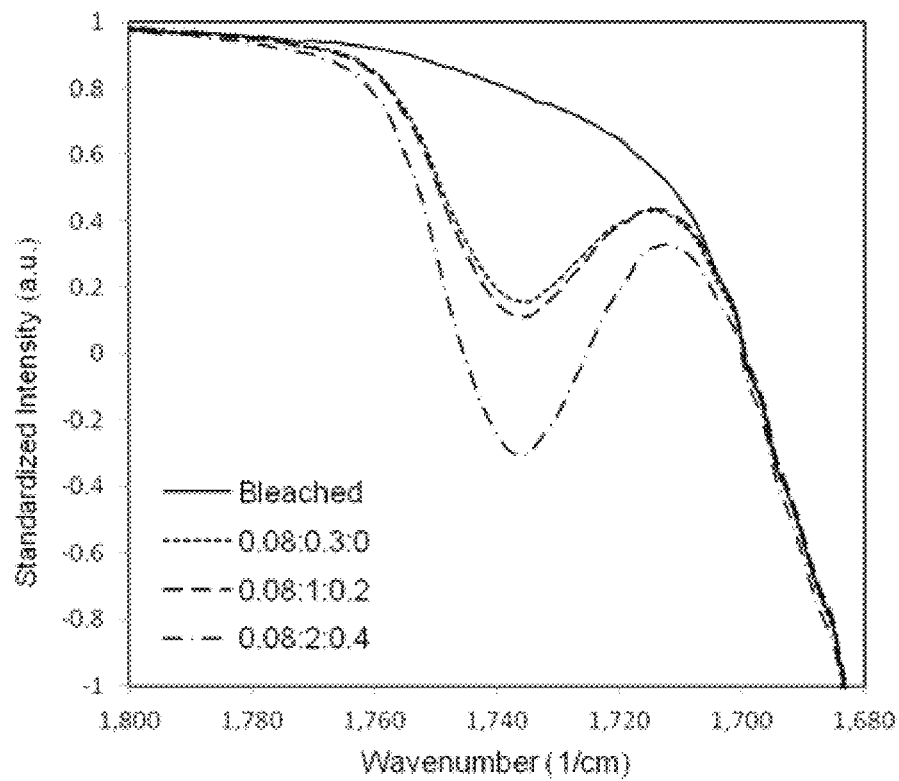
FIG. 19B depicts the carbonyl peak region of FTIR spectra of hair after thiol delivery on bleached hair of an exemplary thiol compound at various tertathiol-to-tertiary amine catalyst-to-acid ratios.

Based on the encouraging results of thiol delivery to virgin (non-damaged) hair using a tetrathiol, pentaerythritol tetrakis(3-mercaptopropionate), in the presence of citric acid, similar conditions were used on bleached hair. FIGS. 19A and 19B show FTIR spectra of bleached hair samples treated at the same tetrathiol molar ratio but with varying catalyst (TEA) and citric acid concentrations. The thiol peak was observed for all three conditions (FIG. 19A) while the signal of the carbonyl peak varied for the different conditions (FIG. 19B). As can be seen, tetrathiol delivery at the highest catalyst to citric acid molar ratio (0.08:2:0.4) resulted in the strongest carbonyl peaks suggesting better delivery efficiency. Overall, the carbonyl peaks signals (FIG. 19B), specifically for the tetratthiol-to-TEA-to-citric acid ratios of 0.08:0.3:0 and 0.08:1:0.2 were found to be lower as compared to the carbonyl peak signals under the same tetrathiol delivery ratios on virgin hair (FIG. 14B). Without being bound by any theory, it is proposed that the lower amount of disulfide bonds present in bleached hair due to the oxidative conditions hair were exposed to during bleaching led to lower tetrathiol delivery. Nevertheless, delivery of pentaerythritol tetrakis(3-mercaptopropionate) is possible with the exemplary tetrathiol-to-TEA-to-citric acid molar ratio of 0.08:2:0.4.

Thiol Delivery on Hair Damaged by Bleaching and Coloring

Figure 20A:
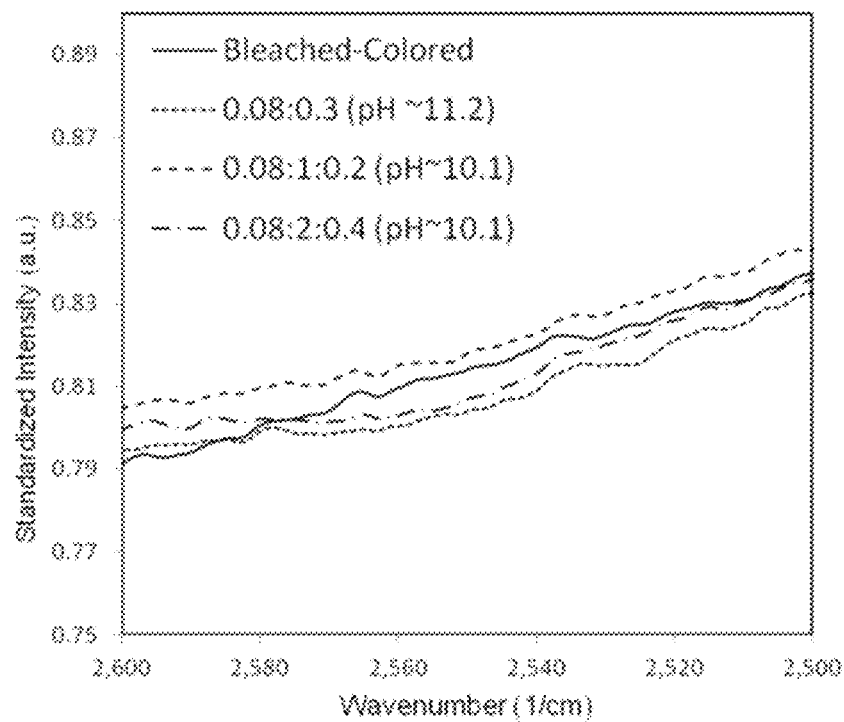
FIG. 20A depicts the thiol peak region of FTIR spectra of hair after thiol delivery on bleached-colored hair of an exemplary thiol compound at various tertathiol-to-tertiary amine catalyst-to-acid ratios.
Figure 20B:
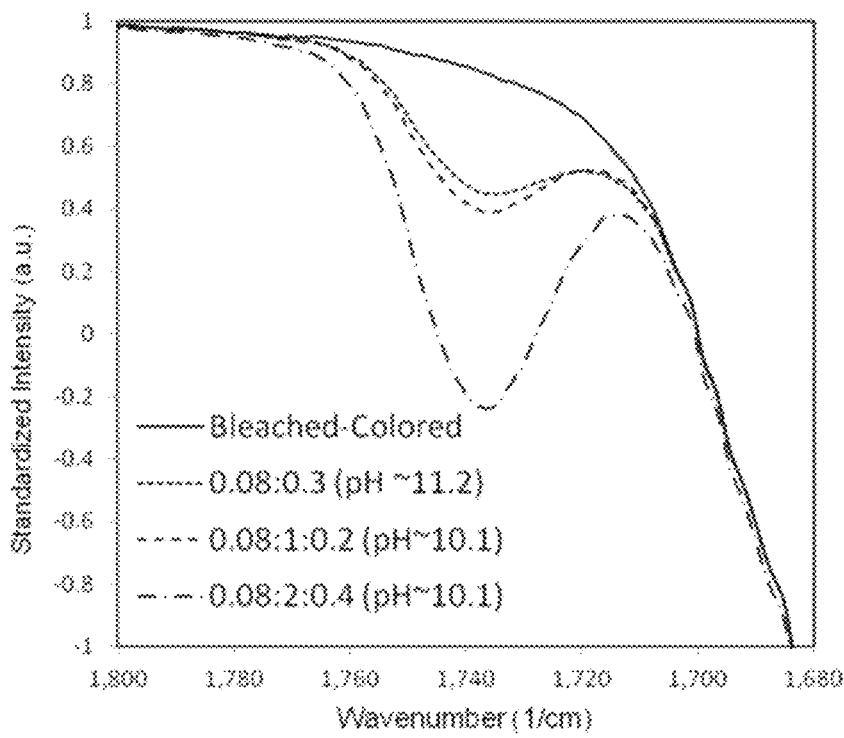
FIG. 20B depicts the carbonyl peak region of FTIR spectra of hair after thiol delivery on bleached-colored hair of an exemplary thiol compound at various tertathiol-to-tertiary amine catalyst-to-acid ratios.

To mimic even more severe hair damage after bleaching, hair samples were further colored. The bleached-colored hair were then treated with tetrathiol solutions at the same tetrathiol-to-TEA ratios used on bleached only hair. As shown in FIGS. 20A and 20B, the same trend was found for bleached-colored hair where tetrathiol delivery was achieved at with an exemplary tetrathiol-to-TEA-to-citric acid ratio of 0.08:2:0.4. In addition, no dramatic color loss from the bleached-colored hair was observed after thiol delivery.

Thiomer Delivery on Hair Damaged by Bleaching

Figure 21:
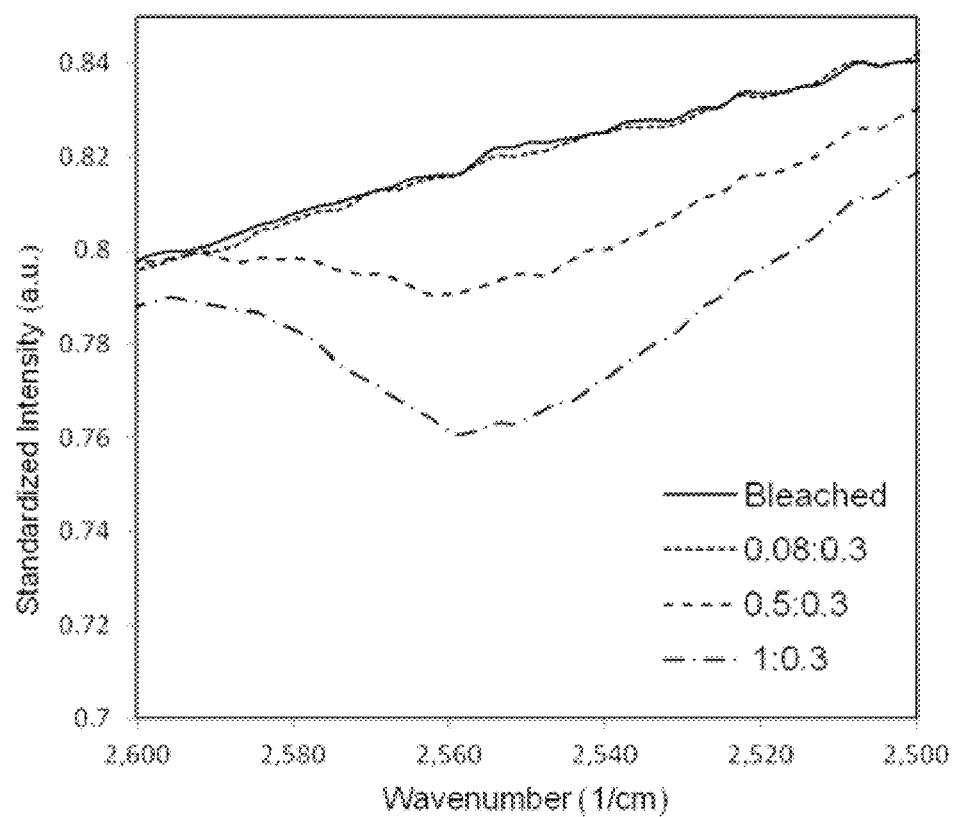
FIG. 21 depicts the thiol peak region of FTIR spectra of hair after thiol delivery on bleached hair of an exemplary thiomer compound at various thiomer-to-tertiary amine catalyst-to-acid ratios.
Figure 22:
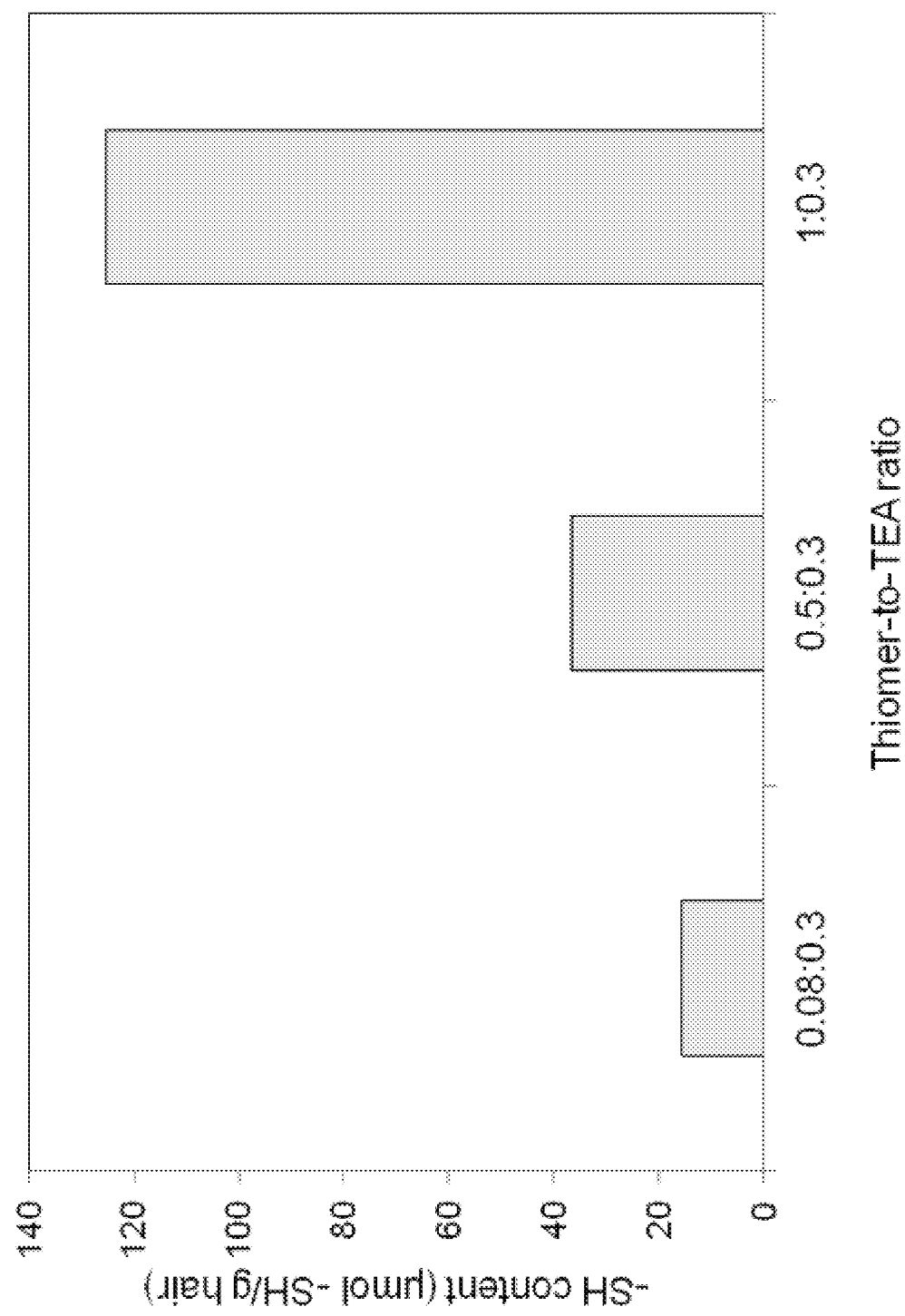
FIG. 22 depicts free thiol content in bleached hair samples treated at different thiomer-to-tertiary amine catalyst ratios with a constant tertiary amine catalyst concentration for 1 h.

Delivery of a large thiomer 4-arm PEG2K-SH was also evaluated on bleached hair. Three different thiomer-to-TEA ratios were screened. The FTIR results suggested that an exemplary thiomer-to-TEA ratio was 1:0.3 (FIG. 21). In addition to FTIR, NEM analysis also was performed to quantify amount of delivered free thiol groups (FIG. 22). Similar to the FTIR results, the NEM results suggested that an exemplary thiomer-to-TEA ratio was 1:0.3.

Exemplary Thiol Delivery Parameters for Monothiols

In this study, delivery of an exemplary monothiol N-acetyl-L-cysteine (also referred to herein as Ac-Cys or NALC) under acidic conditions in a wide pH range of 2.0-7.0 was explored. Previously identified optimal liquor ratio of 1.1:1 was used for all thiol delivery experiments. The effect of N-acetyl-L-cysteine concentration on the delivery efficiency was also evaluated.

Effect of pH

Figure 23:
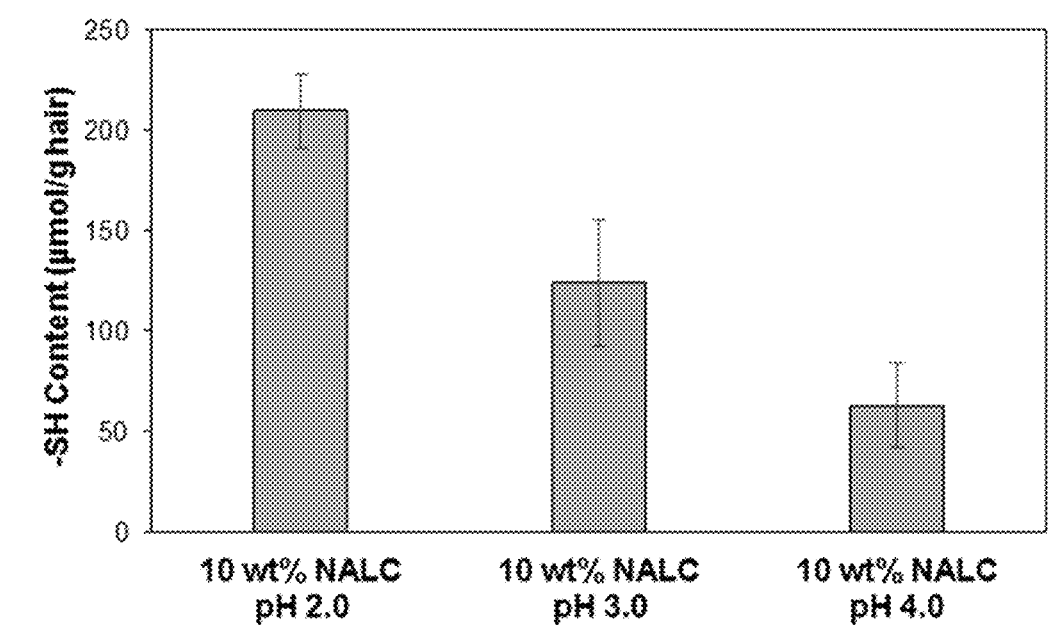
FIG. 23 depicts the free thiol content of hair after thiol delivery of an exemplary monothiol, N-acetyl L-cysteine (Ac-Cys or NALC), at low acidic pHs in the range of 4.0 to 2.0.

Without being bound by any theory, it was expected that higher penetration of a molecule could be achieved if it was delivered in its neutral form (i.e., carries no net charge) since it will have minimal electrostatic interaction with hair. NALC has two pK values, 3.31 and 9.87 and is present in its neutral form below pH of 3.31. Additionally, in this low pH range, delivery NALC is not expected to introduce any disulfide breakage (i.e., hair reduction) and thus not cause any hair damage. The initial delivery screening was carried out with the pH of the NALC solutions varying from 2.0 to 7.0. The results showed that effective delivery was achieved with pH lower than 4.0 and that the efficiency increased with decreasing pH. FIG. 23 shows the amount of delivered free thiol, as determined by the NEM assay, in black wavy hair samples after delivery of 10 wt % NALC at pH 2.0, 3.0, and 4.0. The amount of free thiols delivered increased as the pH of NALC solution decreased. The results suggested that an exemplary pH for thiol delivery was about pH 2.

Effect of N-Acetyl-L-Cys Concentration

Figure 24:
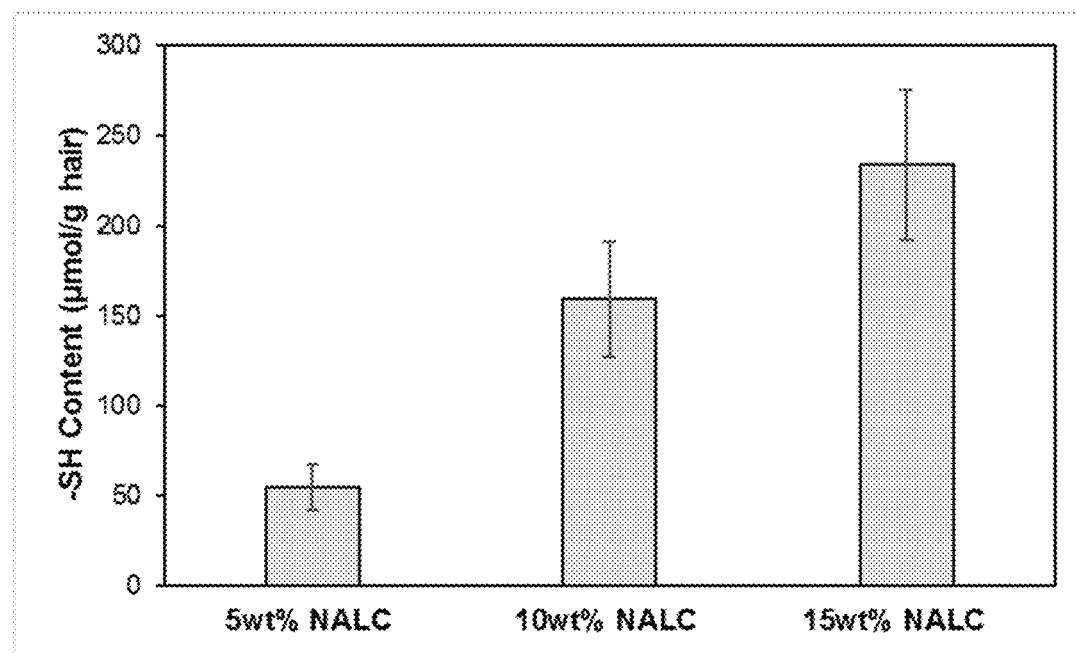
FIG. 24 depicts the free thiol content in hair after thiol delivery of an exemplary monothiol NALC at different concentrations at pH 2.0.
Figure 25:
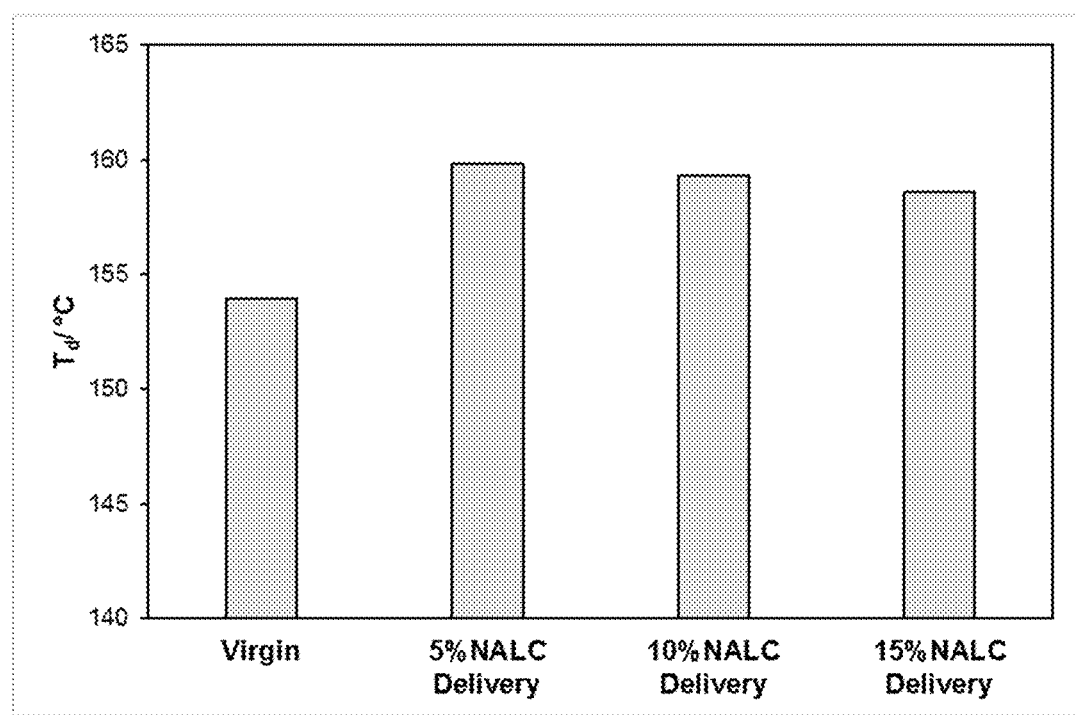
FIG. 25 depicts the denaturation temperatures of hair after thiol delivery of an exemplary monothiol NALC at different concentrations at pH 2.0.

Higher NALC concentrations up to 15 wt % were also used. FIG. 24 shows the free thiol content in black wavy hair samples after 30 min treatment at pH 2.0 in a 15 wt % of NALC aqueous solution was compared to 5 and 10 wt %. The free thiol content increased with increasing NALC concentration. Differential scanning calorimetry (DSC) was also performed on tresses to determine the effect of NALC concentrations on hair denaturation temperatures (Td). FIG. 25 shows Td for black wavy hair samples treated with NALC at three different concentrations, which all led to significant increases in Td, ~6° C., suggesting improvements in hair strength under all tested conditions. Together with the pH screening studies, the results suggested that effective NALC delivery was achieved, for example, at pH 2 with a NALC concentration in the range of 5-15 wt %. Effective NALC delivery was also achieved in bleached black wavy hair, for example, at pH 2 and a 10 wt % concentration, and resulted in ~5° C. increase in Td.

Example 2—Thiol-Michael Grafting of Monomers to Hair

Synthetic Procedure

The thiol-Michael addition of small molecule enes (olefin-containing small molecules) has been used as a grafting pathway for covalent attachment of small molecules to hair. Without being bound by any theory, it is proposed that based on the initiating agent (catalyst), the reaction could proceed via either one of the two pathways: nucleophilic initiation and base catalysis, or both.[15] Both reaction pathways were investigated using different initiating agents: amine-based catalysts which could undergo both base-catalyzed and nucleophile initiated pathways and tertiary phosphine-based catalyst which are primarily responsible for nucleophilic initiation.[15]

Figure 26:
FIG. 26 is a schematic representation of thiol-Michael addition reaction via a base-initiated pathway.
Figure 26:
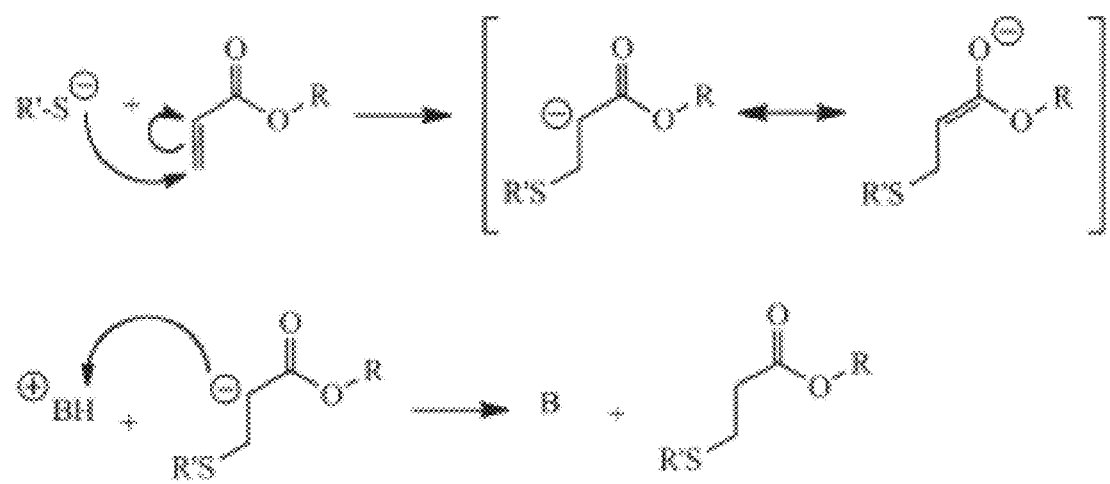

Triethylamine (TEA) was selected as a benign and effective catalyst. Without being bound by any theory, it is proposed that primary and secondary amines are generally assumed to proceed through both mechanisms, while tertiary amines serve as base catalysts only.[15] Without being bound by any theory, FIG. 26 shows the proposed mechanism for the base-mediated pathway, which begins with the deprotonation of the thiol by the base in order to form a thiolate anion.[15] Propagation occurs by β-addition of the thiolate anion to an activated carbonyl, and subsequent proton transfer from the protonated base to yield thiol-Michael adduct.

Figure 27A:
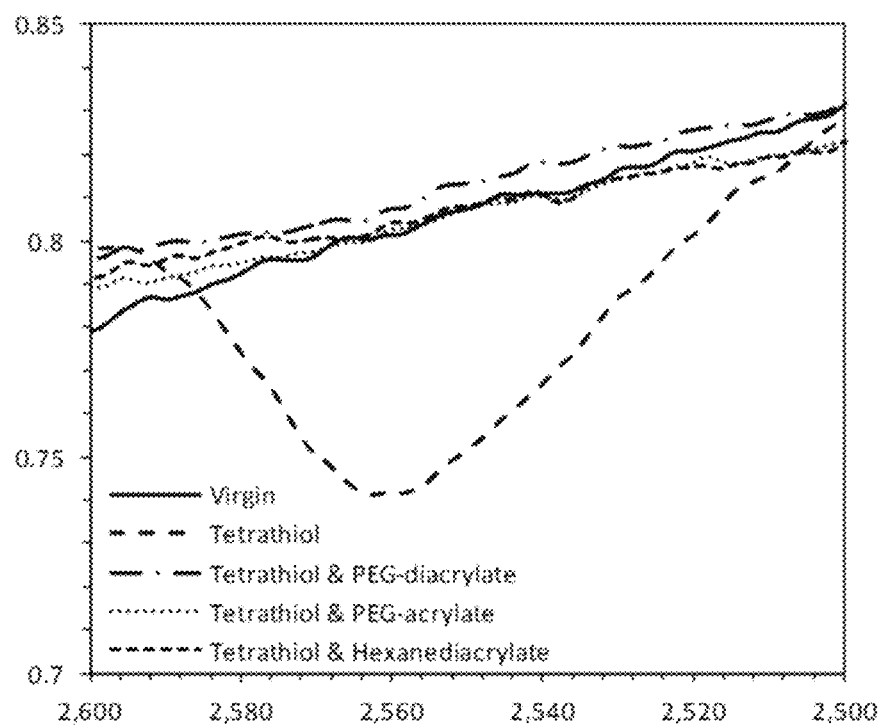
FIG. 27A depicts thiol peak region of FTIR spectra of hair after thiol delivery and grafting with various exemplary acrylate monomers.
Figure 27B:
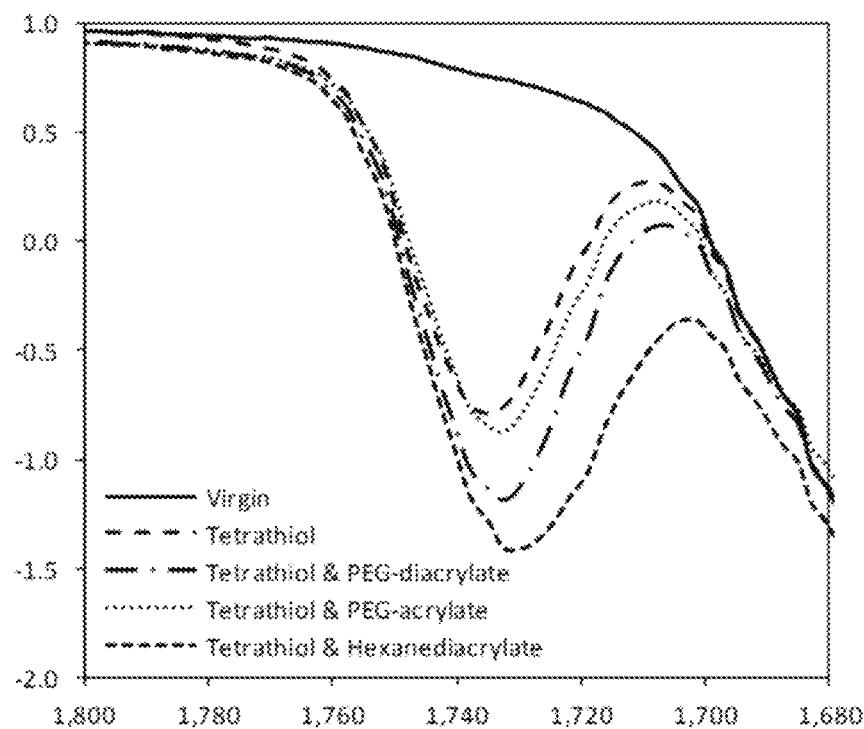
FIG. 27B depicts carbonyl peak region of FTIR spectra of hair after thiol delivery and grafting with various exemplary acrylate monomers.
Figure 27C:
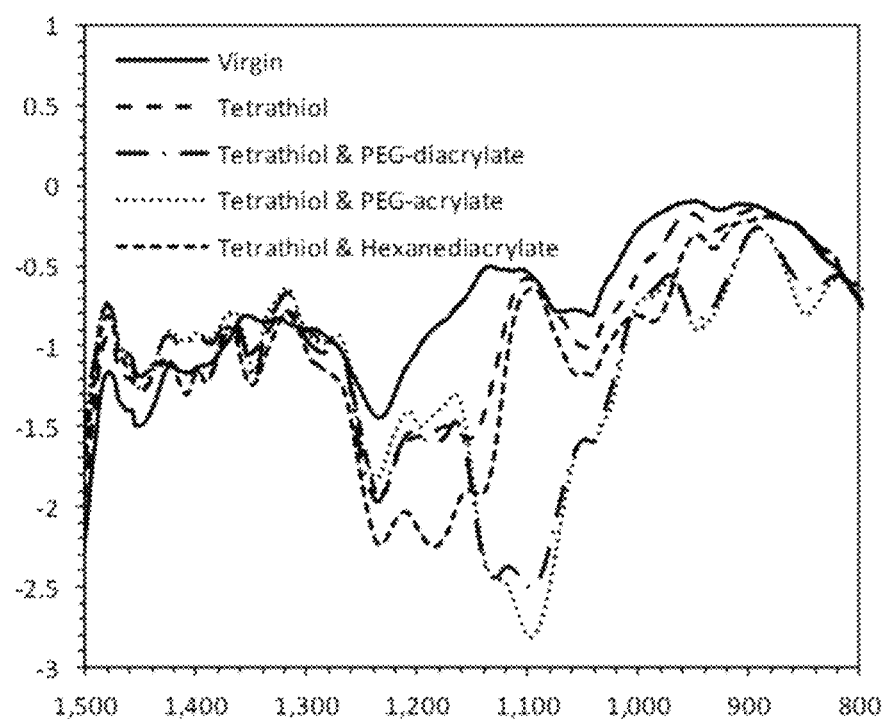
FIG. 27C depicts alkyl peak region of FTIR spectra of hair after thiol delivery and grafting with various exemplary acrylate monomers.
Figure 28:
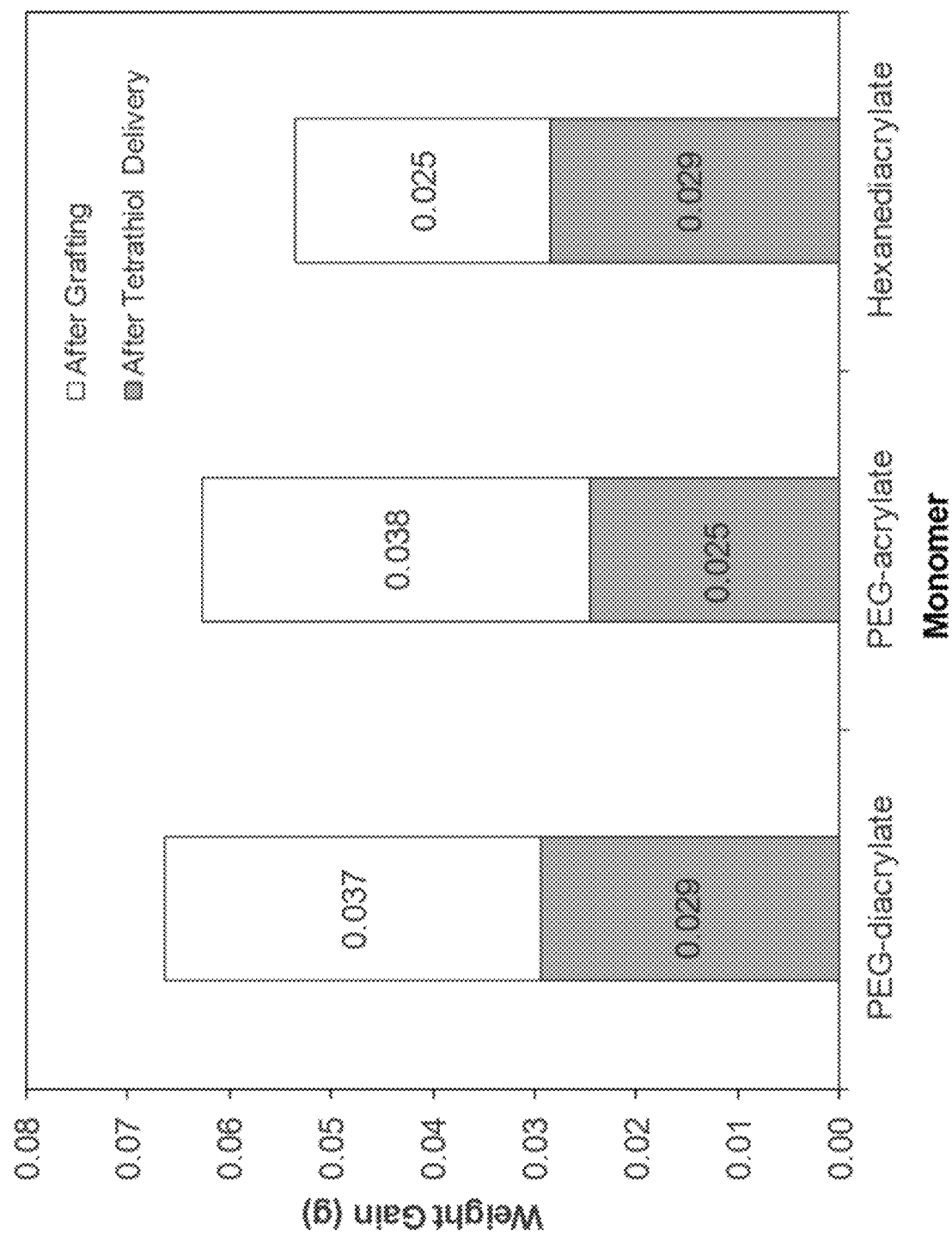
FIG. 28 depicts gravimetric analysis showing absolute weight gains of hair samples after thiol delivery and grafting with exemplary acrylate monomers.

Monomers, including hexyl acrylate, PEG-diacrylate, PEG-acrylate, hexanediacrylate, were selected, and the grafting efficiencies for attaching these monomers to the thiol-delivered (i.e., tetrathiol treated) hair were evaluated using FTIR spectroscopy and gravimetric analysis. FIGS. 27A-27C show the FTIR spectra of hair samples treated with tetrathiol at a 1:0.3 tetrathiol-to-TEA ratio followed by thiol-Michael grafting of PEG-diacrylate, PEG-acrylate, and hexanediacrylate at a monomer-to-TEA-to hair thiol ratio of 1:0.3:1. The successful grafting of all monomers was confirmed by the disappearance of thiol peaks (ca. 2560 cm$^{-1}$, FIG. 27A) as well as the appearance of strong PEG and diacrylate signature peaks in the carbonyl (1680-1800 cm$^{-1}$, FIG. 27B) and alkyl (800-1500 cm$^{-1}$, FIG. 27C) regions. To further confirm and quantify the thiol delivery as well as grafting efficiency, gravimetric analysis was performed. FIG. 28 shows the absolute weight gains of hair samples after the thiol delivery process at a 1:0.3 tetrathiol-to-TEA ratio and after thiol-Michael grafting of PEG-diacrylate, PEG-acrylate, and hexanediacrylate. Significant weight gains were observed for all tetrathiol-treated as well as grafted samples. The slightly lower weight gain for hexanediacrylate can be explained by its lower molecular weight (226 g/mol) as compared to PEG-diacrylate and PEG-acrylate.

Figure 29A:
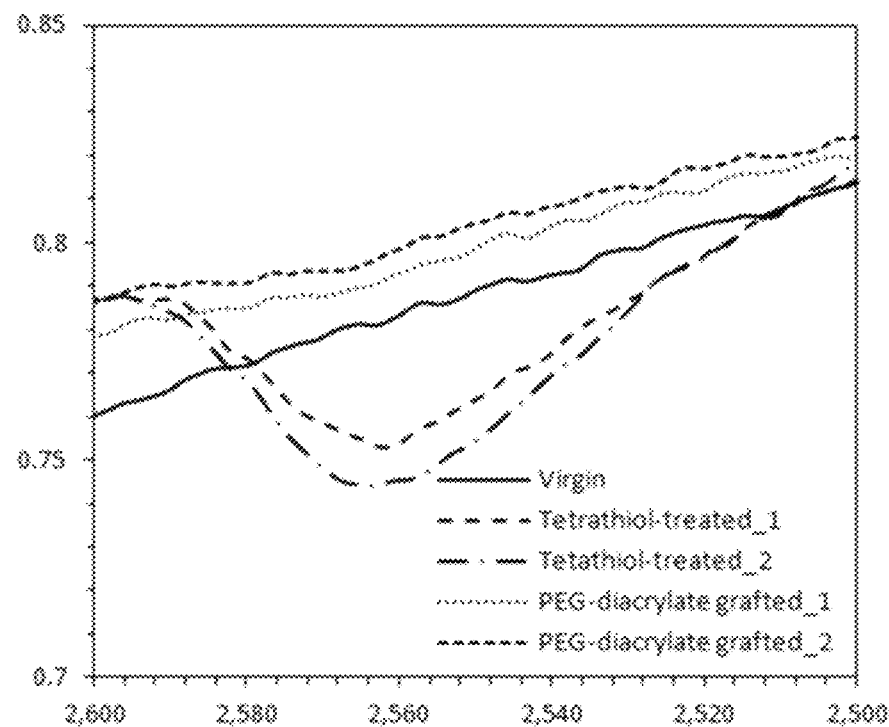
FIG. 29A depicts thiol peak region of FTIR spectra of hair after thiol delivery and grafting with an exemplary PEG-diacrylate monomer.
Figure 29B:
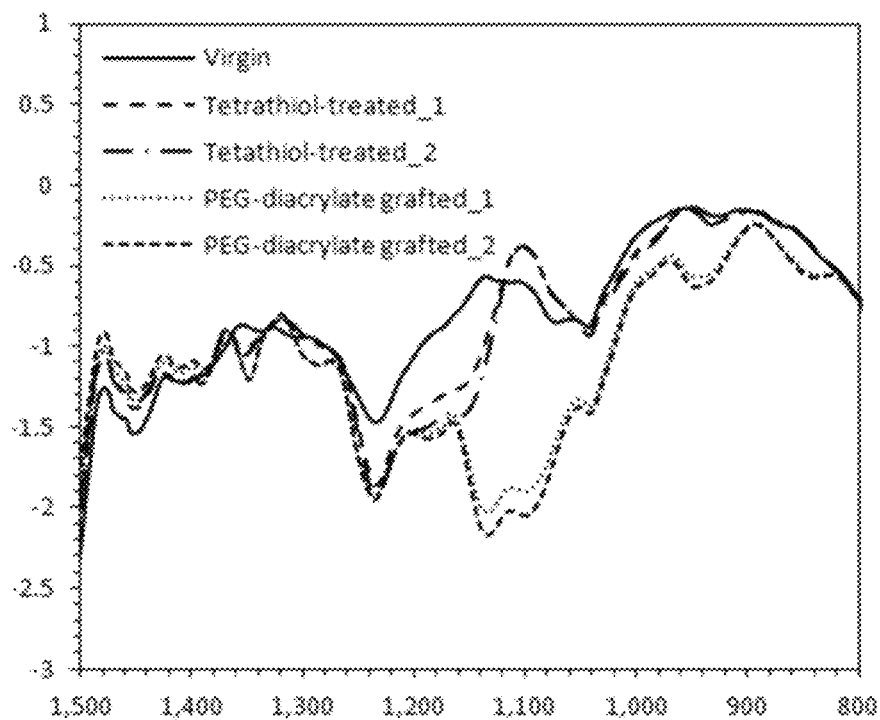
FIG. 29B depicts alkyl peak region of FTIR spectra of hair after thiol delivery and grafting with an exemplary PEG-diacrylate monomer.

To further confirm the effectiveness of the thiol delivery process, PEG-diacrylate grafting on the hair treated with the lowest tetrathiol concentration at a tetrathiol-to-TEA ratio of 0.08:0.3 was also performed. In this case, a relatively low PEG-diacrylate-to-TEA ratio of 0.5:0.3 was also used. Similar to the results obtained at higher tetrathiol and PEG-diacrylate concentrations (FIGS. 27A-274C), a disappearance of thiol peaks (FIG. 29A) as well as an appearance of strong signature peaks in the alkyl region (FIG. 29B) were observed, confirming the successful grafting of PEG-diacrylate. These results demonstrate the effectiveness of thiol delivery even at a very low concentration of a tetrathiol compound.

Synthetic Procedure with Thiomer-Delivered Hair

Figure 30A:
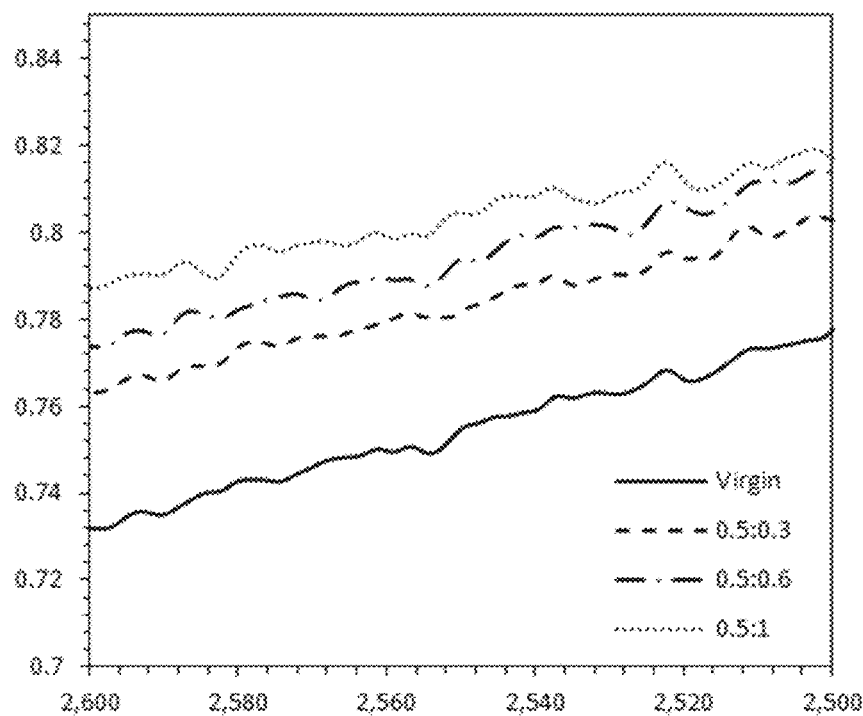
FIG. 30A depicts thiol peak region of FTIR spectra of hair after exemplary thiomer delivery and grafting with an exemplary PEG-diacrylate monomer.
Figure 30B:
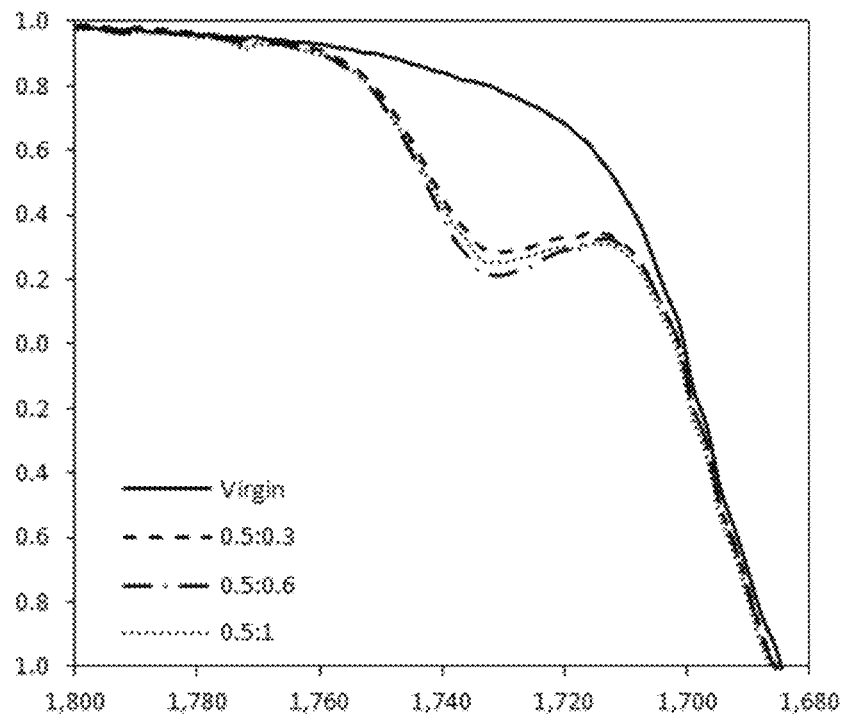
FIG. 30B depicts carbonyl peak region of FTIR spectra of hair after exemplary thiomer delivery and grafting with an exemplary PEG-diacrylate monomer.
Figure 30C:
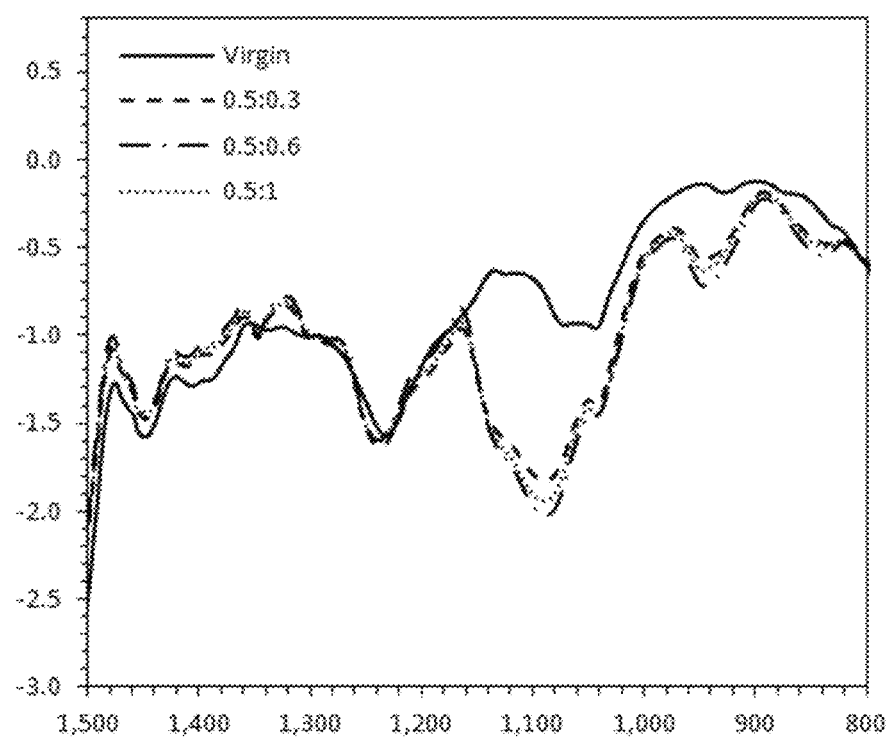
FIG. 30C depicts alkyl peak region of FTIR spectra of hair after exemplary thiomer delivery and grafting with an exemplary PEG-diacrylate monomer.
Figure 31:
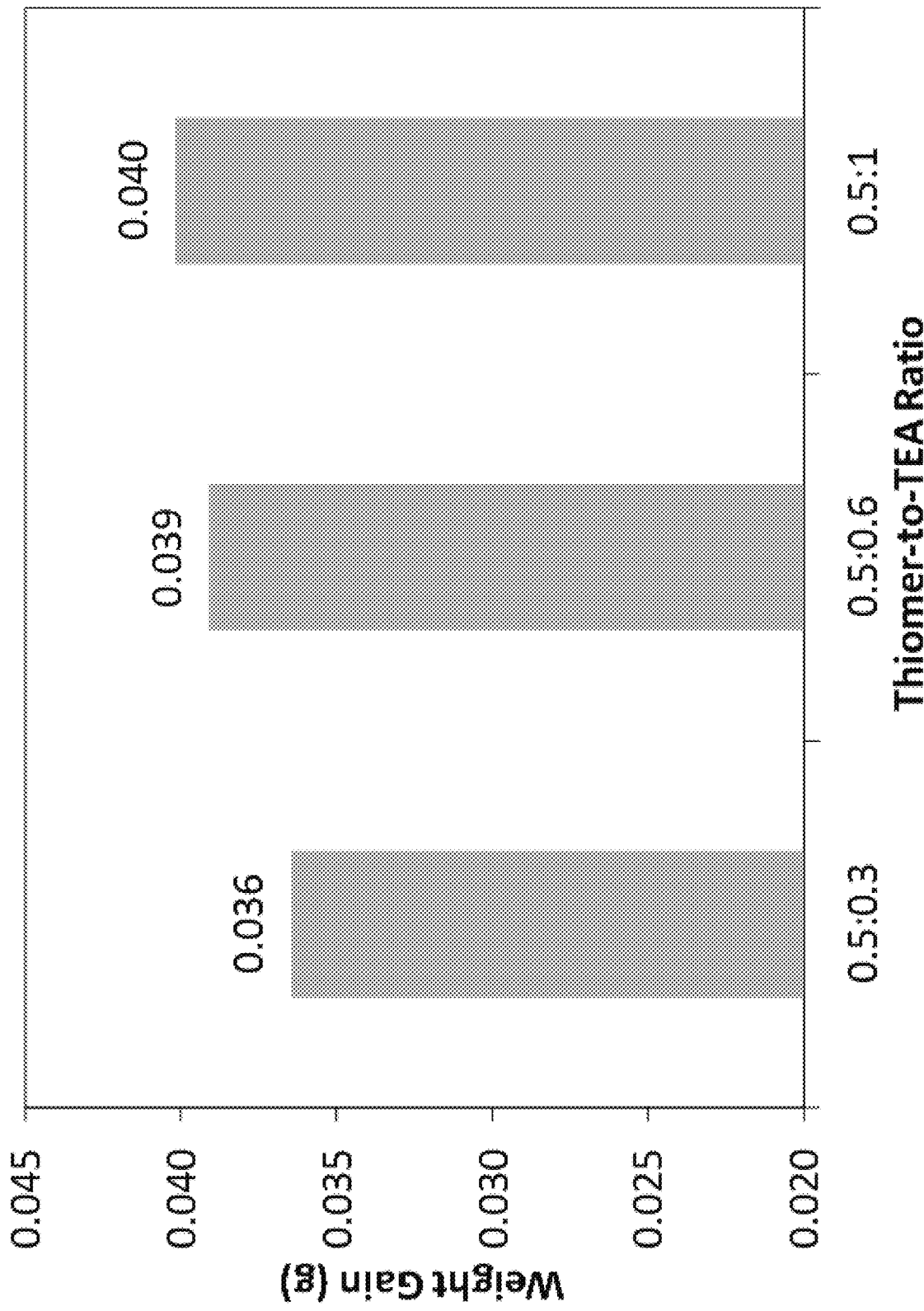
FIG. 31 depicts gravimetric analysis showing absolute weight gains of hair samples after exemplary thiomer delivery and grafting with an exemplary PEG-diacrylate monomers.
Figure 32:
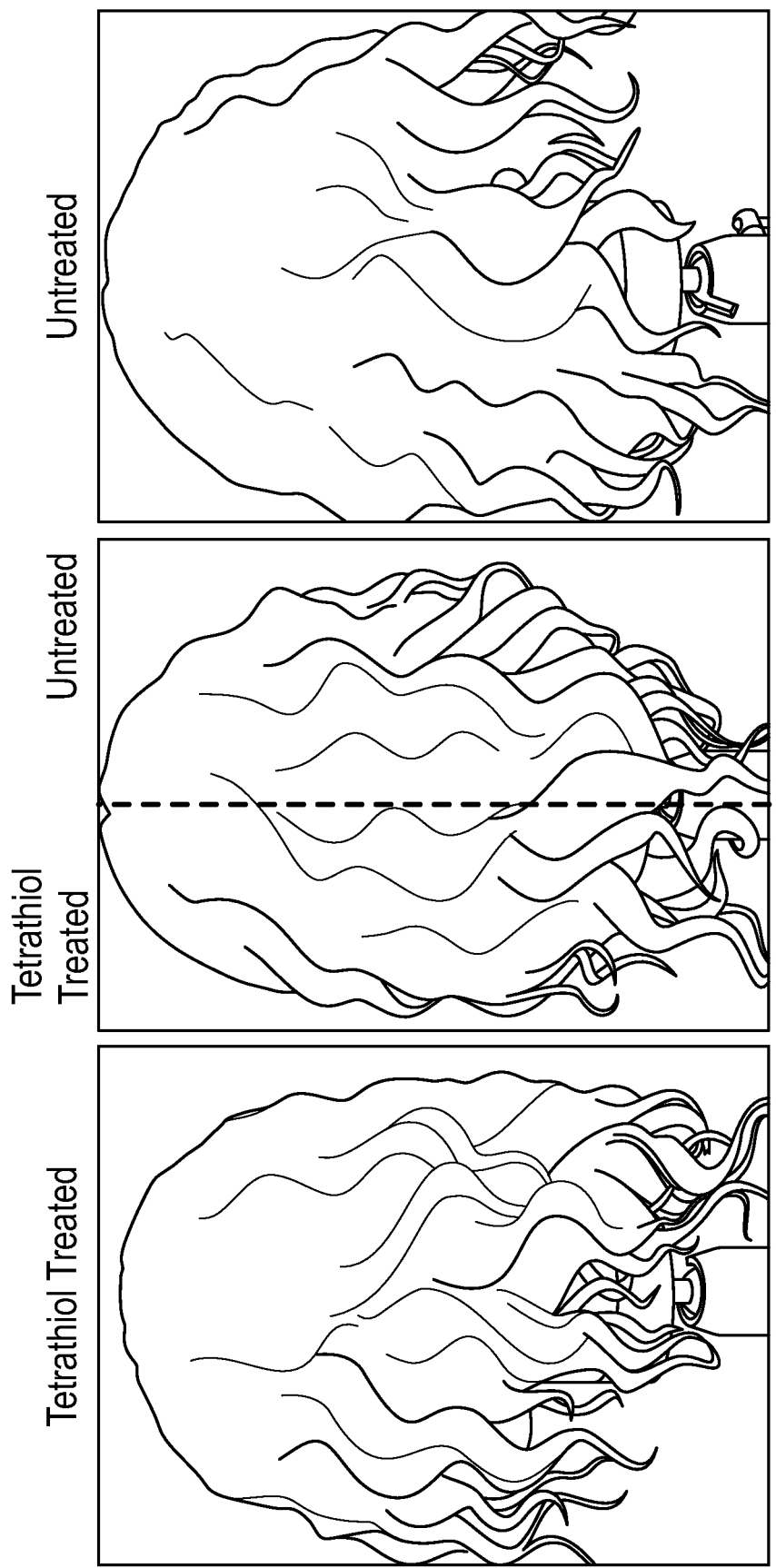
FIG. 32 depicts a mannequin with frizzy hair with one side after exemplary tetrathiol delivery (left) and one side untreated (right).
Figure 33:
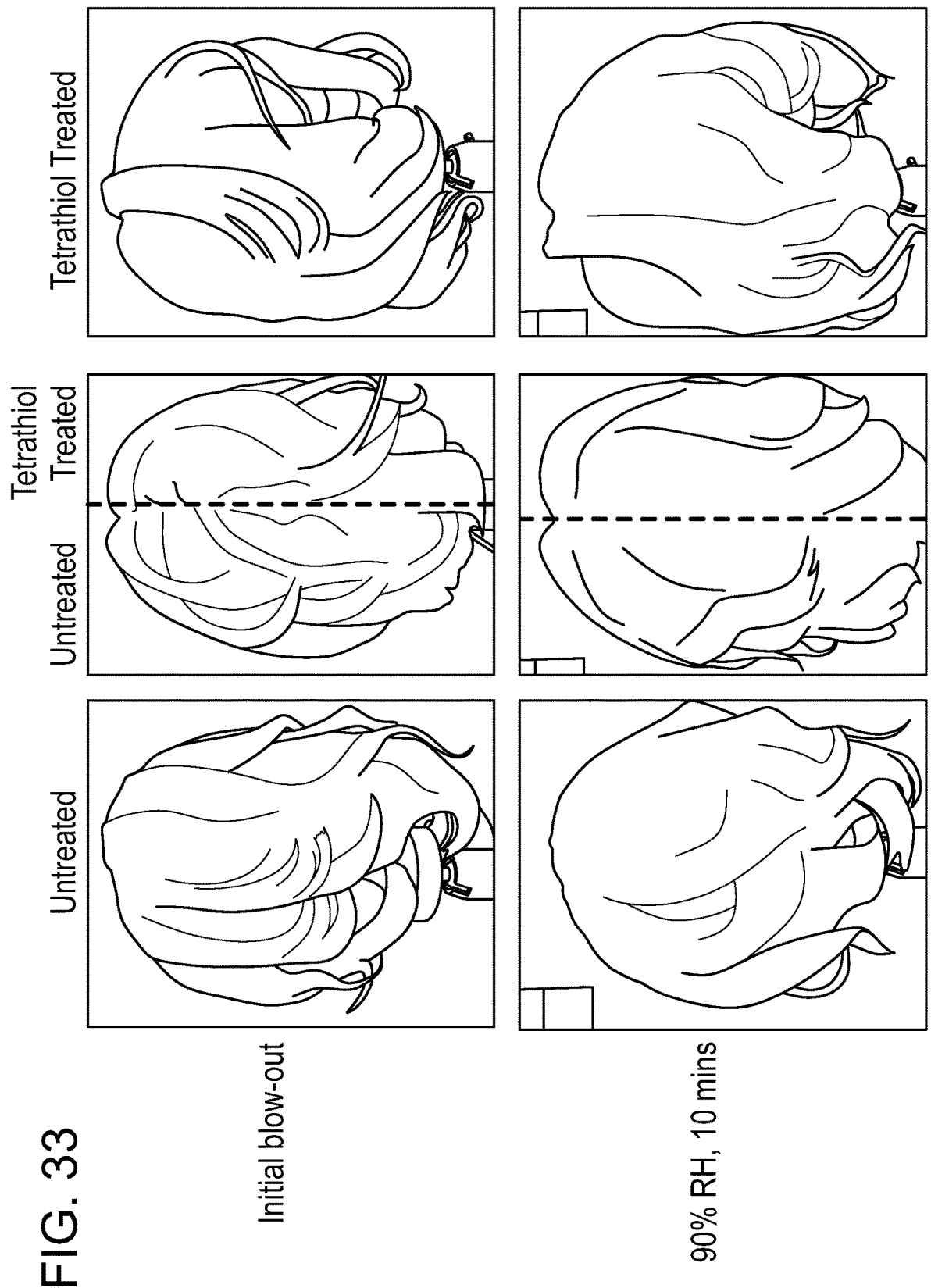
FIG. 33 depicts a mannequin with frizzy hair with one side after exemplary tetrathiol delivery (left) and one side untreated (right) after styling the hair (top panels) and humidity exposure (bottom panels).

To confirm the successful thiomer delivery and free thiol group generation, thiol-Michael grafting of PEG-diacrylate 700 was carried out on the thiomer-delivered hair samples. The grafting efficiencies for attaching an exemplary monomer to the thiomer-delivered hair samples were evaluated using FTIR spectroscopy and gravimetric analysis. FIGS. 30A-30C show the FTIR spectra of hair samples treated with 4-arm PEG2K-SH at thiomer-to-TEA ratios of 0.5:0.3, 0.5:0.6, and 0.5:1.0 followed by thiol-Michael grafting of PEG-diacrylate 700 at a monomer-to-TEA-to hair thiol ratio of 0.5:0.3:1. The successful grafting of PEG-diacrylate on all three hair samples was confirmed by the disappearance of thiol peaks (ca. 2560 cm$^{-1}$, FIG. 30A) as well as the appearance of strong PEG-diacrylate signature peaks in the carbonyl (1680-1800 cm$^{-1}$, FIG. 30B) and alkyl (800-1500 cm$^{-1}$, FIG. 30C) regions. To further confirm and quantify the thiomer delivery as well as grafting efficiency, gravimetric analysis was performed. FIG. 31 shows the significant weight gains of hair samples after thiol-Michael grafting of PEG-diacrylate for all three hair samples. Consistent with the thiomer delivery results shown in FIG. 18, slightly higher weight gains were observed for the two higher TEA concentration samples.

Example 3—Covalent Bonding Analysis

Fourier Transform Infrared (FTIR) Spectroscopy

The presence of tetrathiol delivery was confirmed with FTIR spectroscopy, via the presence of the thiol S—H stretch at about 2560 cm$^{-1}$ and the carboxylate stretch at about 1735 cm$^{-1}$. The presence of grafted vinyl acrylate polymers was confirmed by the disappearance of thiol peaks (ca. 2560 cm$^{-1}$) as well as the appearance of strong PEG and diacrylate signature peaks in the carbonyl (1680-1800 cm$^{-1}$) and alkyl (800-1500 cm$^{-1}$) regions.

Gravimetric Analysis

To further confirm and quantify thiol delivery and grafting efficiencies, gravimetric analysis was performed. The absolute weight gain of tresses after tetrathiol delivery and after grafting were determined for each acrylate monomer (FIG. 28). As a control, a virgin hair tress was used and treated with similar washing and drying steps as grafted samples. Significant increase in weight gain was found for all thiol delivery as well as grafted samples as compared to a control, which further supports tetrathiol delivery and grafting had occurred.

Example 4—Characterization of a Keratin-Containing Material

Methods of treating a keratin-containing material to graft monomeric and polymeric materials to a keratin-containing material were disclosed herein.

Sensory Testing

Blinded sensory testing was used to evaluate visual and tactile properties of tresses and mannequins after tetrathiol delivery. Overall, thiol delivery provided hair with a manageable, smooth, and conditioned feeling for tactile properties. Visual evaluation showed minimization of frizz, good fiber alignment, and that the natural curl shape was preserved.

Shine Band Testing

The shine characteristics of tresses grafted with exemplary acrylates are compared with a tress that was reduced only (not grafted). A blinded sensory evaluator determines the sample that exhibits the best shine.

Mechanical Testing

Treatment of hair with tetrathiol, TEA, and citric acid at the ratio of 0.08:2:0.4 was shown to have minimal impact on the mechanical properties of single hair fibers when tested via INSTRON® 3342 mechanical testing. Table 2 shows that the average modulus and elongation at break were nearly identical before and after treatment. Unlike traditional reduction methods, the methods of treating a keratin-containing material described herein generated significant thiol content without weakening hair fibers.

TABLE 2

Exemplary mechanical properties of single hair fibers[a].

| Treatment | Young's Modulus (GPa) | Elongation at Break (%) |
|---|---|---|
| Virgin hair | 3.6 ± 0.2 | 50.3 ± 0.2 |
| Tetrathiol:TEA:Citric Acid Ratio of 0.08:2:0.4 for 1 h | 3.8 ± 0.2 | 49.8 ± 0.2 |

[a]Sample size of N = 50. Values reported as mean ± RSD. All hair fibers were harvested from one individual.

Mechanical characterization of keratin-containing material samples was carried out on the INSTRON® 3342 (Instron, Norwood Mass.) equipped with 100 N load-cell (Instron #2519-103). Keratin-containing material samples were mounted onto the instrument via modified Instron 2710-101 grips, which prevented the sample from slipping from the grips during testing. For example, single-fiber hair samples were evaluated using an INSTRON®.

The extension pull test was preprogrammed into Bluehill Lite Software used to operate the instrument. The extension pull test was used to determine the stiffness, stretchiness, and strength of a keratin-containing material by measuring the Young's Modulus, elongation at break, and ultimate tensile strength. The Young's Modulus is utilized as a measure of material stiffness, while the elongation at break is used as a measure of material flexibility. The sample was mounted onto the instrument such that the hair sample was fixed within the instrument grips. The instrument grip distance was adjusted such that the sample was at neutral extension as indicated by the instrument force being close to zero (+0.01N). Subsequently, extension until sample failure was performed at 20 mm/min. The stress strain data recorded by instrument during the extension was exported to Excel where the reported mechanical properties were calculated.

An Excel template was used to automatically extract a number of parameters from the instrument generated data. The Young's modulus (YM) was calculated as the straight line slope of the stress-strain curve between 0.1% and 0.4%. The R squared value of the linear fit was above 0.98 or else the data point was discarded. The elongation at break was determined as the strain at which the sample, for example, a hair fiber, breaks. Ultimate stress was calculated as the maximum stress recorded during the experiment. Ultimate tensile strength was the capacity of a material to withstand loads tending to elongate. Ultimate tensile strength was the maximum stress that a material or sample could withstand while being pulled before breaking.

Water Uptake Testing

A hair sample is first dried in a desiccator for 16 hours. The sample is weighed and is placed into a humidity chamber at 90% RH for 15 minutes. The sample is then removed and weighed again.

Water Contact Angle

Water contact angles (CA) are measured using a goniometer equipped with an automated dispenser (Model 500, Rame-Hart). Advancing and receding angles are measured with the sessile drop method by depositing a droplet of 1 μL on the surface, then increasing the volume to 4 μL, finally decreasing it. Advancing angles are considered as the maximum angles observed during the droplet growth. Receding contact angles are measured in correspondence of the drop profile just before the contact surface reduction. Each CA value is averaged from measurements of four drops with an estimated maximum error of 4°. The CA is measured using distilled water.

Differential Scanning Calorimetry

Differential Scanning calorimetry (DSC) analysis is performed on both wet and dry hair. For wet method DSC, about 5-10 mg of hair is weighed into stainless steel pressure resistant sample pan and 50 μL of water is added. The pan is then sealed and samples are equilibrated overnight before DSC analysis. Samples are then heated from 30 to 250° C. at 5° C./min heating rate. For dry method DSC, about 5-10 mg of hair is weighed into aluminium sample pan and sealed with a lid. The lid is later pierced to allow moisture to escape during analysis. The samples are also heated from 30 to 250° C. at 5° C./min heating rate.

Scanning Electron Microscopy (SEM)

To study morphological changes of the damaged hair surface before and after grafting, scanning electron microscopy (SEM) analysis is employed. Hair is evaluated after bleaching, after reduction of bleached hair with ATG, after thiol delivery, and after thiol delivery followed by grafting of bleached hair with an exemplary acrylate. Hair cuticles are expected to appear dramatically lifted after bleaching as compared to virgin hair. Cuticle morphology is observed after various treatments. Hair cuticle appearance, especially lift of the cuticles and smoothness of the cuticle surface, are to be evaluated and compared to virgin hair.

Lowry Assay for Protein Loss

To study changes of the hair surface before and after thiol delivery, a protein quantification assay was employed. After various chemical treatments such as bleaching, perming, or straightening treatments were applied, hair cuticles become damaged which resulted in higher protein loss. To quantify this loss before and after grafting, a Modified Lowry Protein Assay was employed. Hair fibers were first cut into ¼ inch pieces and about 250 mg of hair was submerged into 4 mLml of water in the scintiallation vial. Vials were then placed on the automatic vortex machine for 4 hours. The supernatant was then collected and diluted with 0.2N NaOH solution at 1:1 ratio for each hair sample and left to sit for 30 minutes for solubilization. About 200 µL of solubilized protein solution was then added into a 2 mL Eppendorf tube and mixed with 1 mL of Modified Lowry Reagent at 20-seconds intervals. Each sample was run in triplicate. After about 10 minutes, 100 µL of Folin-Ciocalteu Reagent was added into each sample and vortexed. The solutions were then left to develop for another 30 minutes. After 30 minutes, solutions were transferred into cuvettes and their absorbance at about 750 nm was measured using UV-Vis spectrophotometer. As expected, after bleaching, proteins were more easily leached out of the hair fibers as indicated by a dramatic increase in protein loss for virgin hair compared to bleached hair. In addition, chemical treatments with commercial products led to a further increase in protein loss.

Example 5—Thiol Delivery with Grafting or Additives

N-Acetyl-L-Cys Delivery+Grafting
Effect of Grafting Monomer pH

Figure 34:
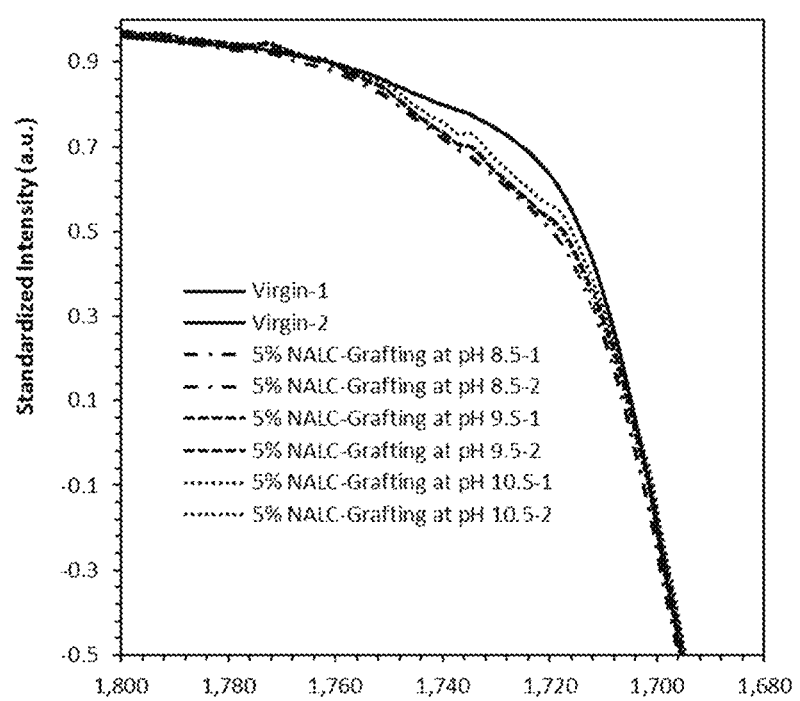
FIG. 34 depicts the carbonyl peak region of FTIR spectra of hair after thiol delivery of an exemplary monothiol NALC and grafting at different alkaline pHs.
Figure 35:
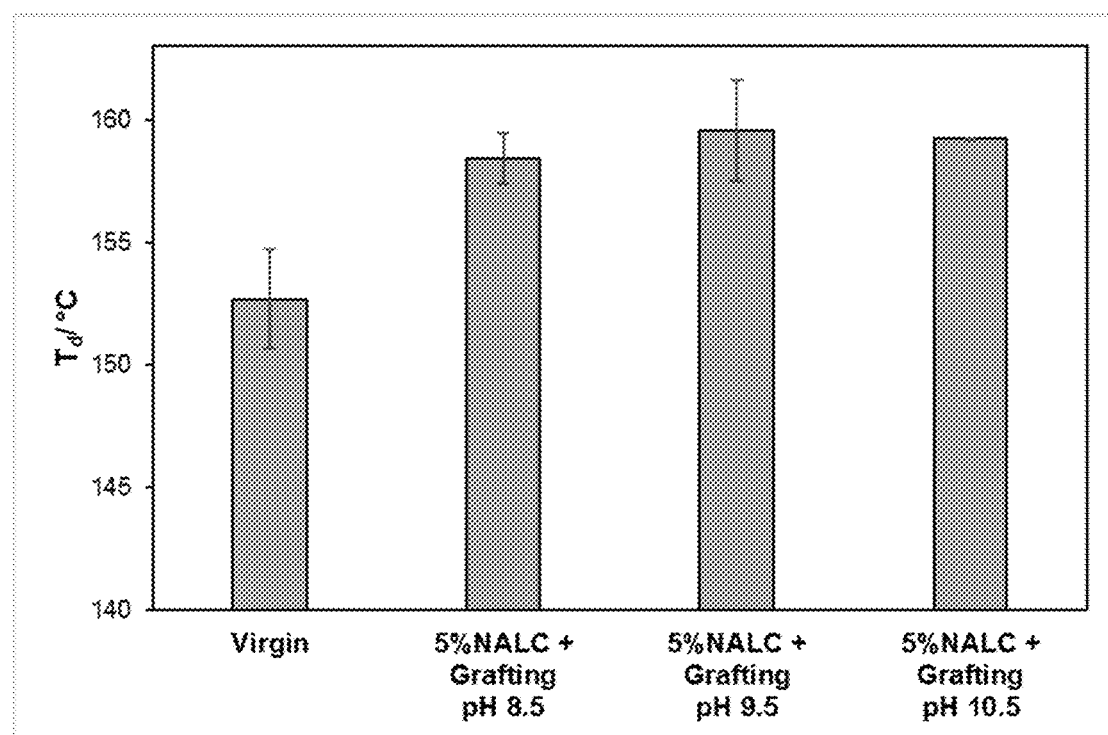
FIG. 35 depicts the denaturation temperature of hair after thiol delivery of an exemplary monothiol NALC followed by grafting at different alkaline pHs.
Figure 36:
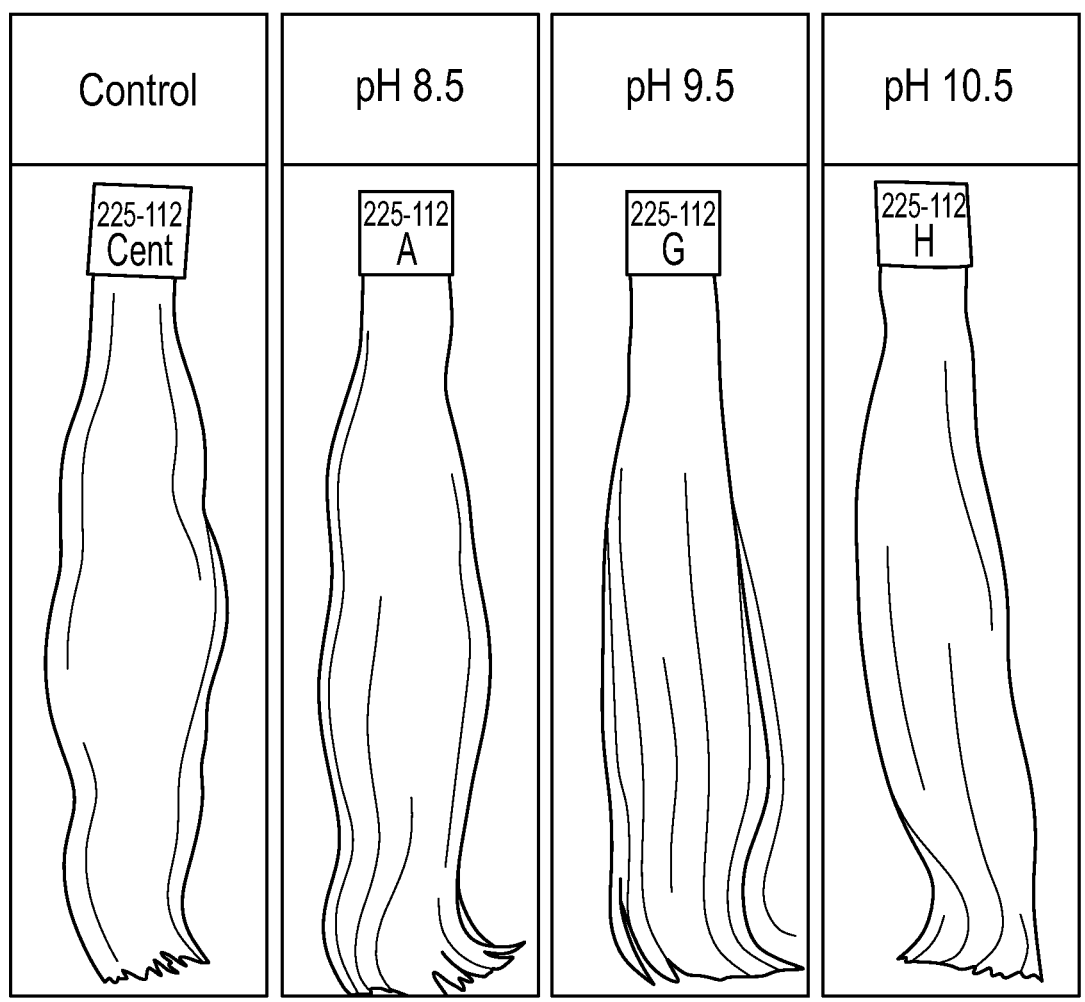
FIG. 36 depicts an image showing the straightening performance of hair after thiol delivery of an exemplary monothiol NALC followed by grafting at different alkaline pHs.

To confirm the successful thiol delivery of an exemplary monthiol NALC and further enhance straightening performance, grafting of PEG-diacrylate via thiol-Michael addition method was performed on the NALC delivered hair samples. In this study, the grafting process consisted of two steps, delivery of 5 wt % NALC at pH 2 for a reaction time of 30 min followed by application of a PEG-diacrylate aqueous solution with a monomer to hair —SH ratio of 0.38:1. Preliminary screening showed that grafting with a PEG-diacrylate monomer pH of 8.5 could achieve a substantial straightening performance. To further boost the performance, higher pH values, including 9.5 and 10.5, on the PEG-diacrylate monomer solution were also tested. In all cases, the pH of the monomer solution was adjusted with 10 mM Tris buffer. The grafting was performed at a monomer to thiol ratio of 0.38:1 for 30 min Before the grafting step, an optional rinsing step was also tested, in which the tress was rinsed with a Tris buffer solution for 20 s before the monomer application. The data suggested that the rinsing step did not seem to significantly affect straightening performance or grafting efficiency. Therefore, NALC thiol delivery followed by grafting without an intermediate rinsing step was used for all further testing. FIG. 34 shows the FTIR spectra of hair samples grafted at pH 8.5, 9.5, and 10.5. The detectable carbonyl peak (1680-1800 cm$^{-1}$) confirmed the successful grafting at all pH values. FIG. 35 shows that the hair denaturation temperatures all increased about 6-7° C. after the monothiol delivery and grafting treatment, suggesting improvements in hair strength. The results suggested that an exemplary pH for the monomer solution was about pH 9.5 for grafting after monothiol delivery (FIG. 36).

Effect of N-Acetyl-L-Cys Concentration

Figure 37:
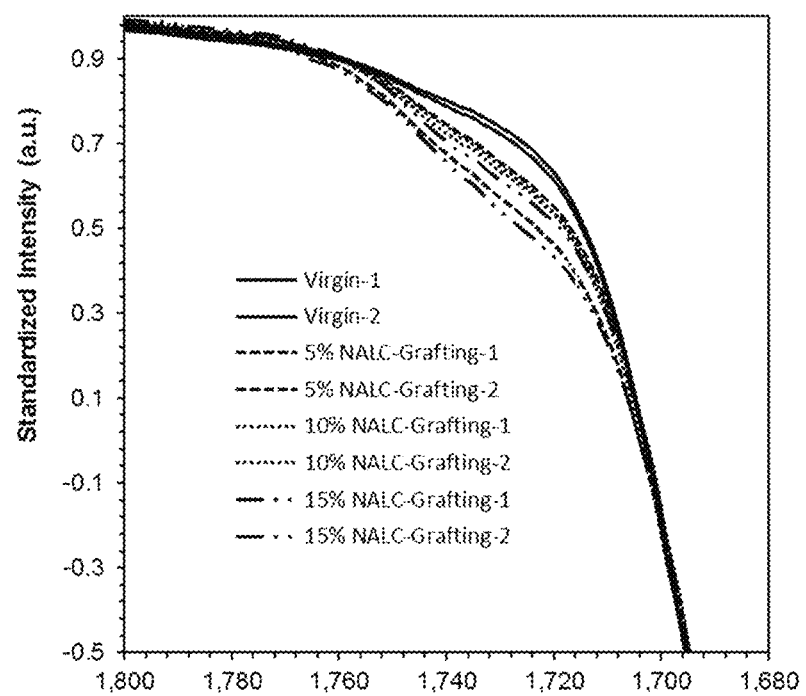
FIG. 37 depicts the carbonyl peak region of FTIR spectra of hair after thiol delivery of an exemplary monothiol NALC at different concentrations followed by grafting at pH 9.5.
Figure 38:
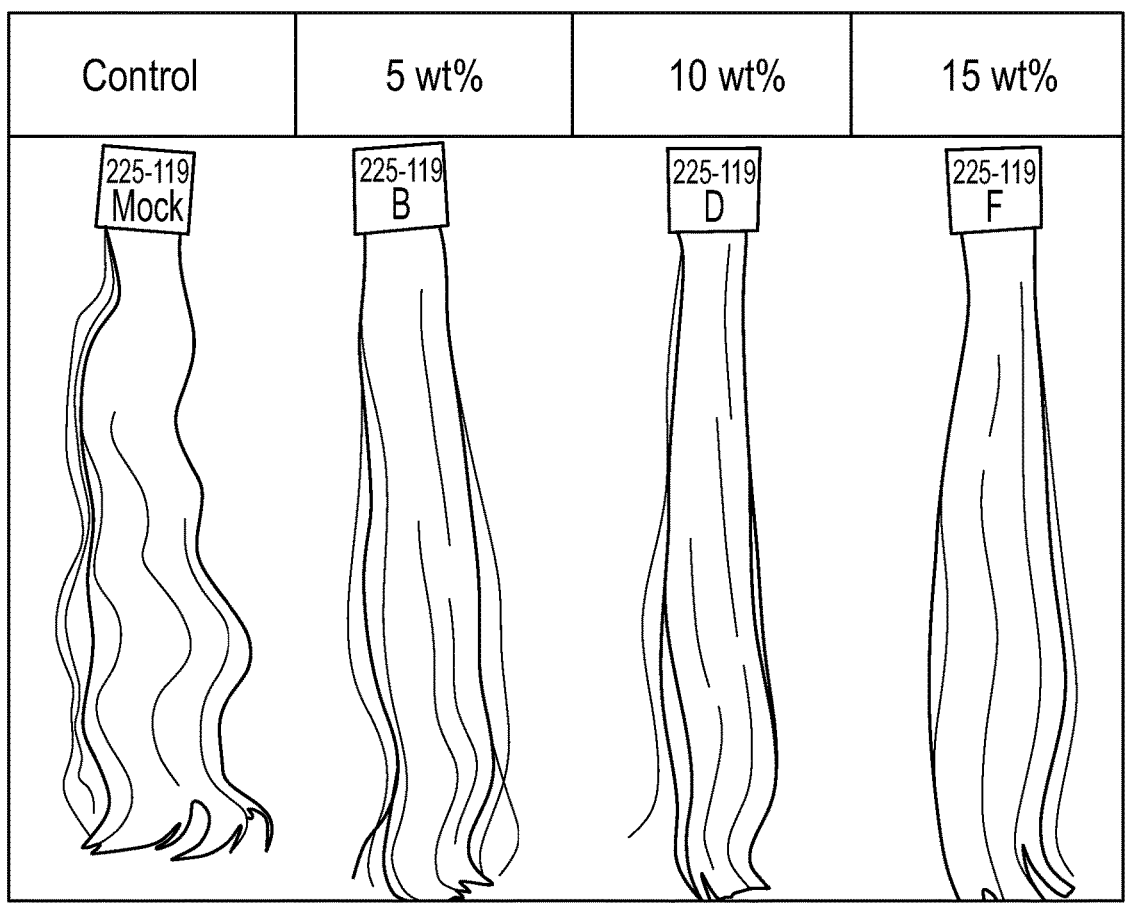
FIG. 38 depicts an image showing the straightening performance of hair after thiol delivery of an exemplary monothiol NALC at different concentrations followed by grafting at pH 9.5.
Figure 39:
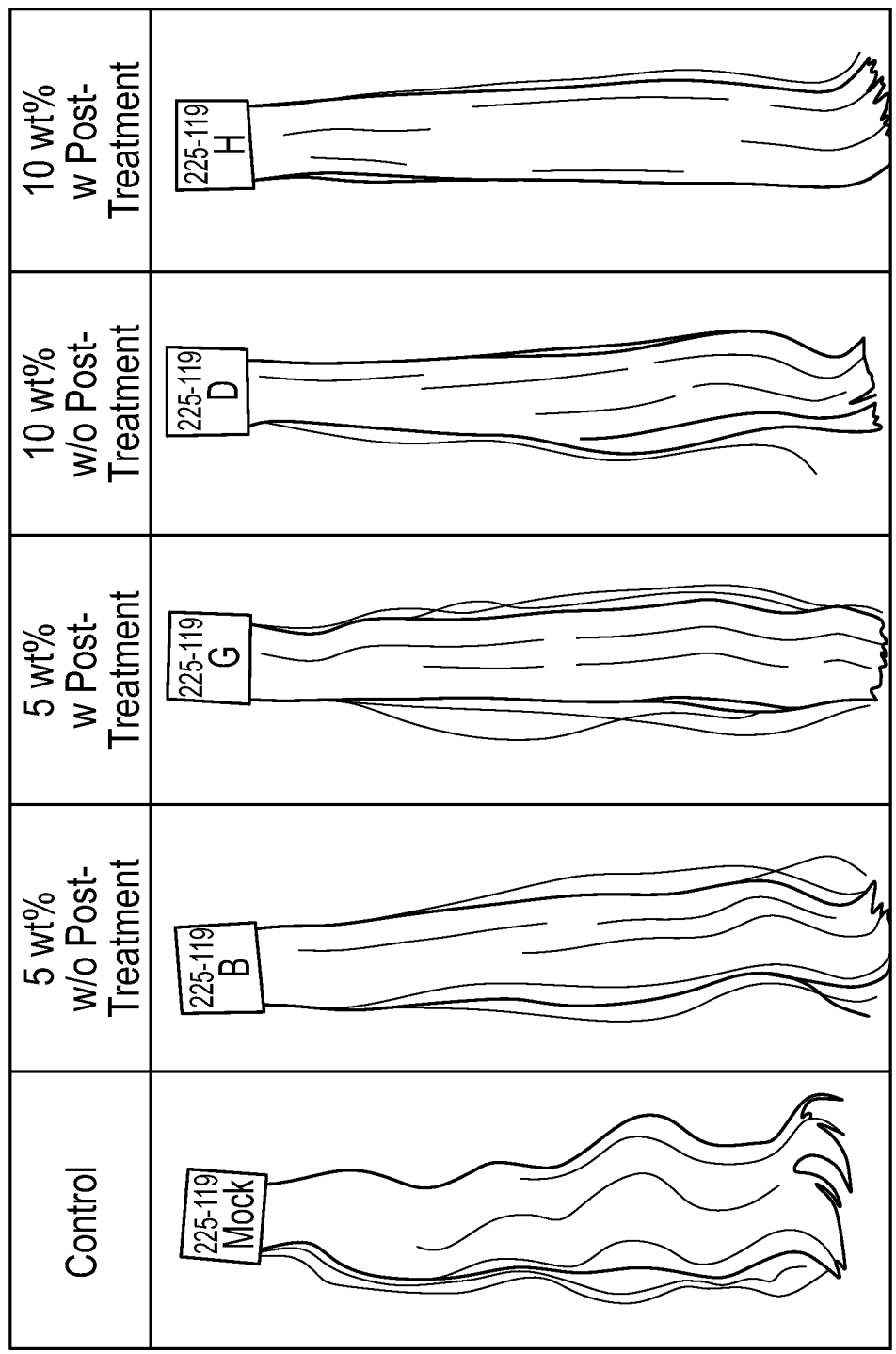
FIG. 39 depicts an image showing the straightening performance of hair after thiol delivery of an exemplary monothiol NALC at two different concentrations followed by grafting at pH 9.5 comparing before and after post-treatment with gluconolactone and citric acid.
Figure 40:
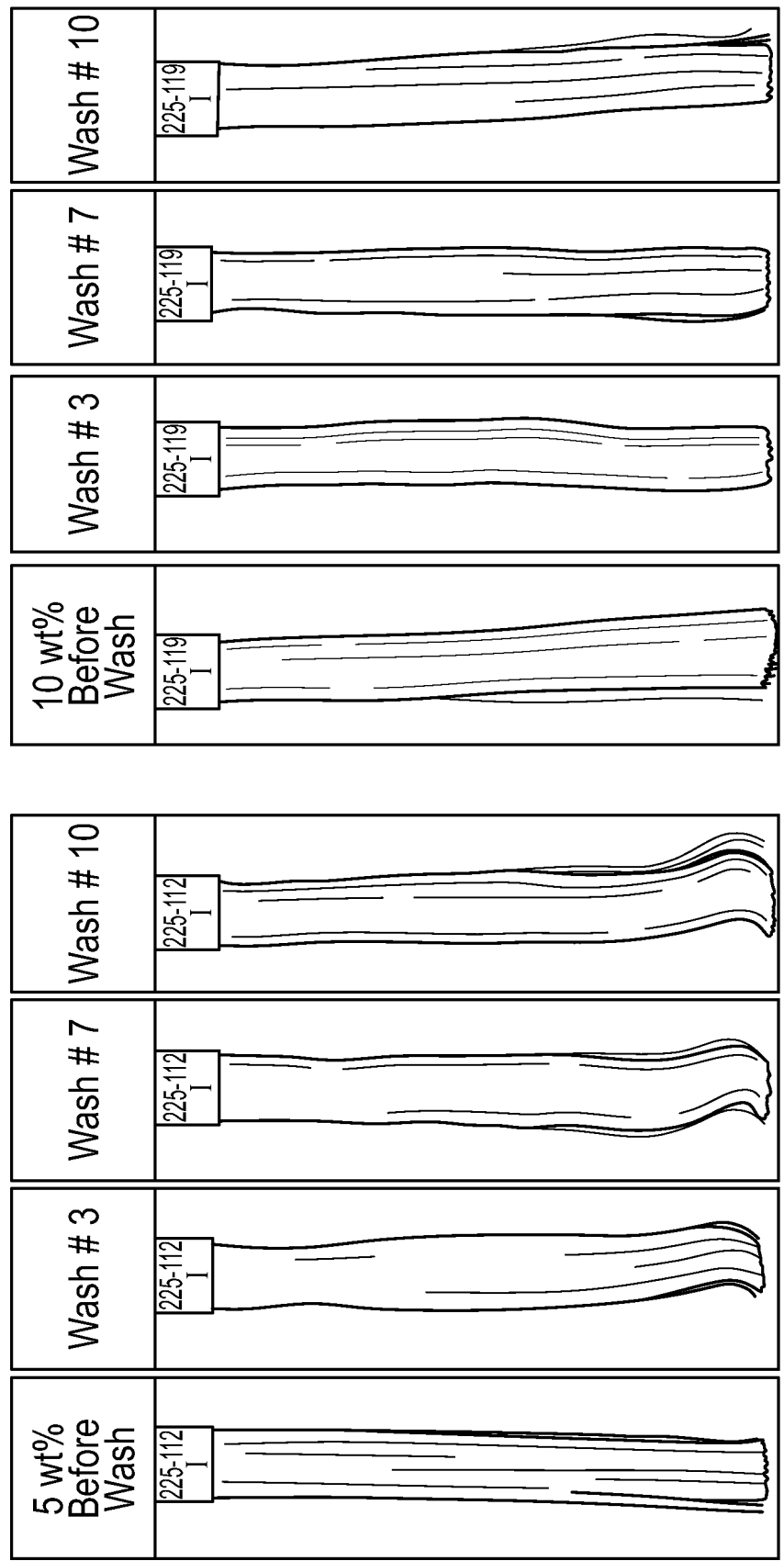
FIG. 40 depicts an image showing the long-lasting straightening performance over 10 shampoo and conditioner washes of hair after thiol delivery of an exemplary monothiol NALC at two different concentrations followed by grafting at pH 9.5, post-treatment with gluconolactone and citric acid and a flat iron step.

To further study the grafting efficiency and straightening performance, grafting of PEG-diacrylate on thiol-delivered hair at higher NALC concentrations were also explored. FIG. 37 shows the FTIR spectra of hair samples treated with 5 wt %, 10 wt %, and 15 wt % NALC at pH 2 followed by thiol-Michael grafting of PEG-diacrylate at pH 9.5 with a monomer to SH ratio of 0.38:1. The detectable carbonyl peak (1680-1800 cm$^{-1}$) confirmed the successful grafting on hair treated with all three different NALC concentrations. The results suggested that the tress treated with 10 wt % NALC followed by PEG-diacrylate 7000 grafting at pH 9.5 showed exemplary straightening performance (FIG. 38). Together with the monomer pH screening experiments, the results suggested that NALC delivery at a 10 wt % concentration followed by PEG-diacrylate grafting at pH 9.5 would achieve exemplary grafting efficiency and straightening performance N-Acetyl-L-Cys Delivery+Grafting+GLCA Post-Treatment To study the straightening performance for the NALC delivered and PEG-diacrylate grafted system, an additional polycarboxylic acids post-treatment step was explored. The NALC delivery and PEG-diacrylate grafting were performed with a 30 min thiol-delivery at pH 2.0 with 5 wt % or 10 wt % NALC followed by a 30 min grafting of 50 wt % PEG-diacrylate 700 at pH 9.5 with a monomer to thiol ratio of 0.38:1 on virgin black wavy hair. The post-treatment consisted of an aqueous solution of 2 wt % gluconolactone, 2 wt % citric acid, and 2 wt % N-acetyl glycine at pH 2.0, and was carried out for 15 min followed by flat ironing at 450° F. As shown in FIG. 39, for both 5 wt % and 10 wt % NALC-delivered systems, post-treatment led to improved initial straightening performance compared to the tresses without the post-treatment. To evaluate the durability of straightness, the treated hair tresses were also subjected to washing with shampoo and conditioner and the performance was evaluated after 3, 7, and 10 washes. The washing study as shown in FIG. 40 also shows that the straightening effect was well preserved after up to 10 washes.

N-Acetyl-L-Cys Delivery+GLCA Post-Treatment

Figure 41:
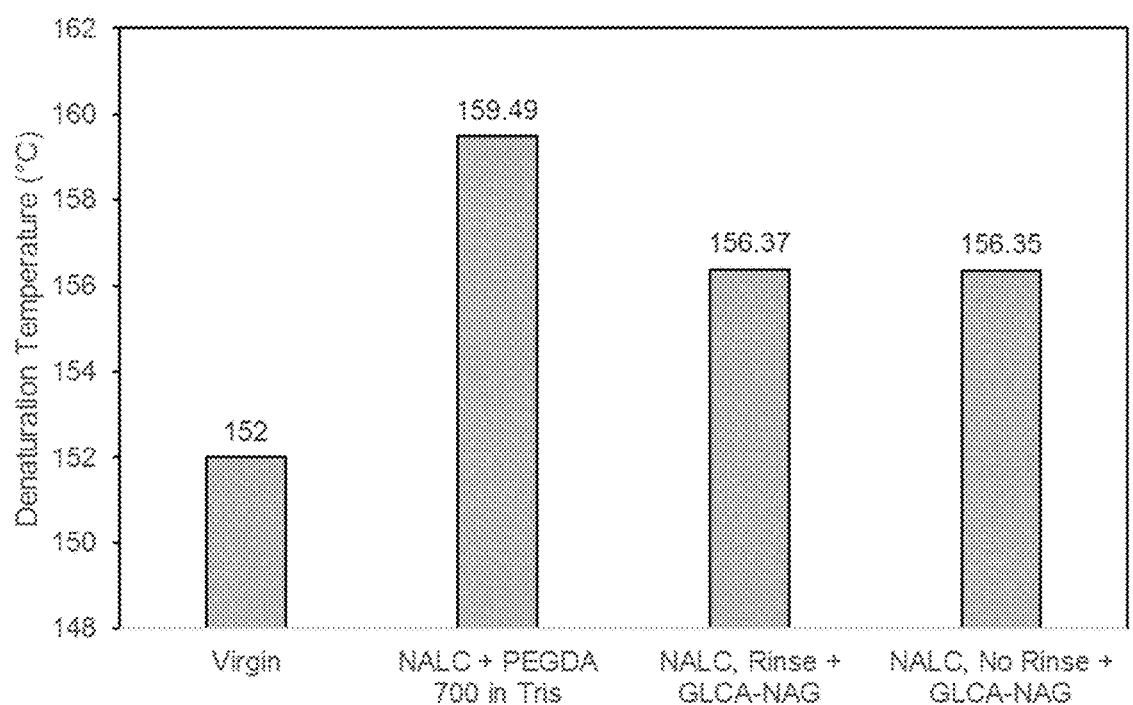
FIG. 41 depicts denaturation temperatures of untreated virgin hair after thiol delivery of an exemplary monothiol NALC followed by grafting with an exemplary PEG-diacrylate monomer or post-treatment with gluconolactone and citric acid.
Figure 42A:
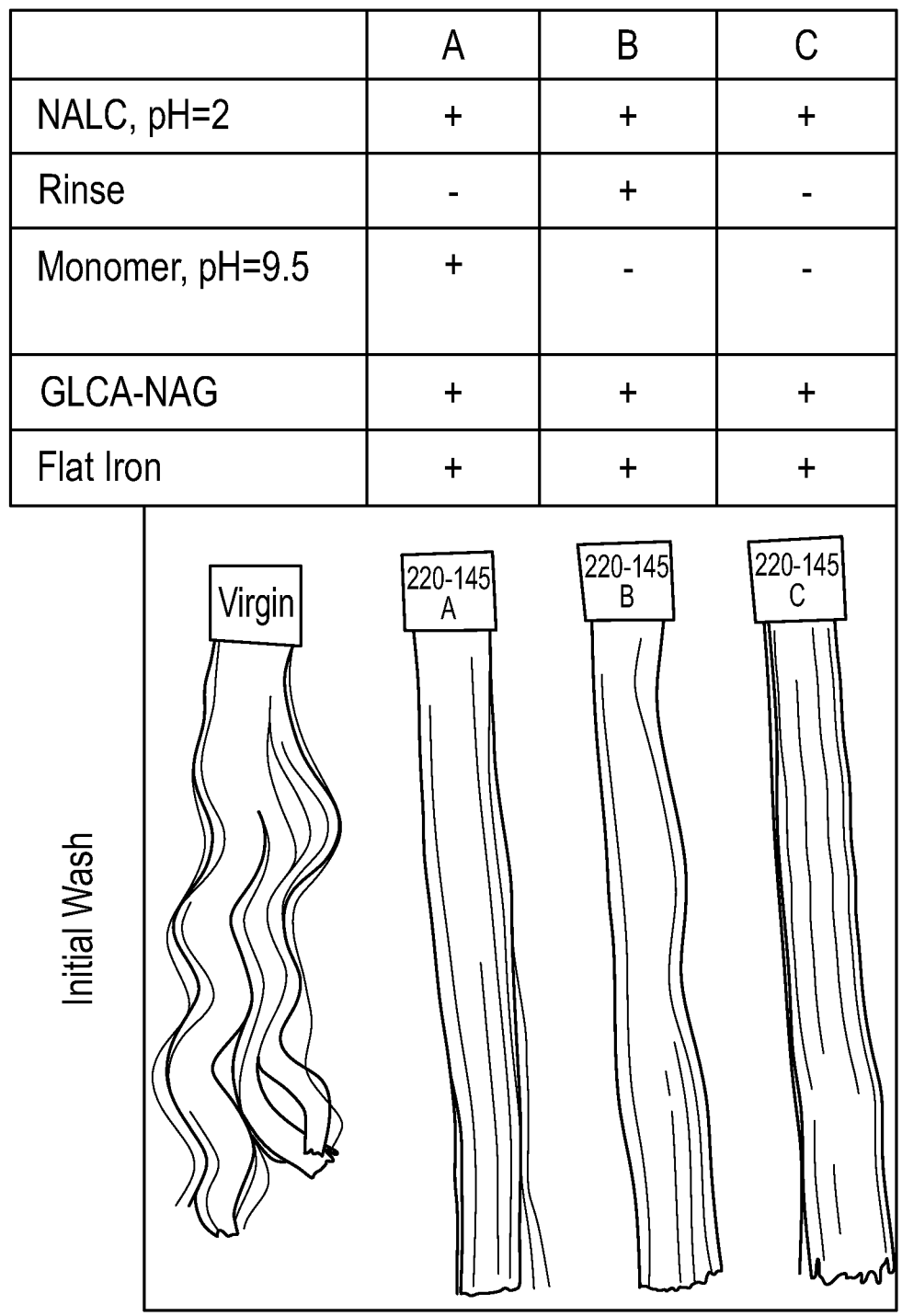
FIG. 42A depicts initial images of untreated hair and of hair after thiol delivery of an exemplary monothiol NALC followed by an exemplary post-treatment with gluconolactone and citric acid.
Figure 42B:
FIG. 42B depicts images of hair after thiol delivery of an exemplary monothiol NALC followed by an exemplary post-treatment with gluconolactone and citric acid after 15 shampoo and conditioner washes.

NALC delivery followed by a post-treatment with polycarboxylic acids by skipping the PEG-diacrylate grafting step was also explored. The delivery step was 30 minutes long and was followed by either no rinse or a quick water rinse. A GLCA post-treatment solution consisting of 2 wt % gluconolactone, 2 wt % citric acid, and 2 wt % N-acetyl glycine at pH 2.0 was then applied for another 15 minutes after which hair tresses were flat ironed at 450° F. FIG. 41 shows that hair denaturation temperatures increased under all conditions compared to untreated virgin wavy hair, suggesting improvements in hair strength. Although the tresses treated with NALC delivery followed by GLCA post-treatment without the PEG-diacrylate grafting step led to a slightly lower hair denaturation temperature increases compared to that with the grafting step, the various treatments did all achieve very similar initial straightening performance (FIG. 42A). The washing study showed that all tresses remained relatively straight after 15 shampoo and conditioner washes. The sample without rinse between NALC delivery and GLCA post-treatment showed exemplary durability of straightness (FIG. 42B).

REFERENCES CITED

1. Finlay, A. Y.; Frost, P.; Keith, A. D.; Snipes, W. An assessment of factors influencing flexibility on human fingernails. *Br. J. Dermatol.* 1980, 103, 357-365.

2. Robbins, C. R. *Chemical and Physical Behavior of Human Hair.* 5th ed. 2012.
3. Kalkbrenner, U.; Koener, H.; Hoecker, H.; Rivett, D. E. Studies on the composition of the wool cuticle. *Proc. 8th Int. Wool Text. Res. Conf.*, Christchurch, New Zealand. 1990, 1, 398-407.
4. Carr, C. M.; Leaver, I. H.; Hughes, A. E. X-ray photoelectron spectroscopic study of the wool fiber surface. *Textile Res.* 1986, 56, 457.
5. Breakspear, S.; Smith, J. R., Luengo, G. Effect of the covalently linked fatty acid 18-MEA on the nanotribology of hair's outermost surface. *J. Struct. Biol.* 2005, 149, 235-242.
6. Torre, C. A.; Bhusham, B.; Yang, J.-Z.; Torgerson, P. M. Nanotribological effects of silicone type, silicone deposition level, and surfactant type on human hair using atomic force microscopy. *J. Cosmet. Sci.*, 2006, 57, 37-56.
7. Kuzuhara, A., Hori, T. Diffusion behaviour of reducing agents into keratin fibers using microspectrophotometry. *J. Appl. Polym. Sci* 2004, 94, 1131-1138.
8. Kuzuhara, A. Hori, T. Analysis of heterogeneous reaction between reducing agents and keratin fibers using Raman spectroscopy and microspectrophotometry. *J. Mol. Struct.* 2013, 1037, 85-92.
9. Manuszak, M. A.; Borish, E. T.; Wickett, R. R. The kinetics of disulfide bond reduction in hair by ammonium thioglycolate and dithiglycolic acid. *J. Soc. Cosmet. Sci.* 1996, 47, 49-58.
10. Manuszak, M. A.; Borish, E. T.; Wickett, R. R. Reduction of human hair by cysteamine and ammonium thioglycolate: A correlation of amino acid analysis and single-fiber tensile kinetic data. *J. Soc. Cosmet. Sci.* 1996, 47, 213-227.
11. Chatani, S.; Nair, D. P.; Bowman, C. N. Relative reactivity and selectivity of vinyl sulfones and acrylates towards the thiol-Michael addition reaction and polymerization. *Polym. Chem.* 2013, 4, 1048-1055.
12. Lowe, A. B.; Hoyle, C. E.; Bowman, C. N. Thiol-yne click chemistry: A powerful and versatile method for materials synthesis. *J. Mater. Chem.* 2010, 20, 4745-4750.
13. Hoyle, C. E.; Bowman, C. N. Thiol-ene click chemistry. *Angew. Chem. Int. Ed.* 2010, 49, 1540-1573.
14. Mather, B. D.; Viswanathan, K.; Miller, K. M.; Long, T. E. Michael addition reactions in macromolecular design for emerging technologies. *Prog. Polym. Sci.* 2006, 31, 487-531.
15. Desmet, G. B.; Sabbe, M. K.; D'hooge, R.; Espeel, P.; Celasun, S.; Marin, G. B.; Du Prez, F. E.; Reyniers, M-F. Thiol-Michael addition in polar aprotic solvents: nucleophilic initiation or base catalysts? *Polym. Chem.* 2017, 8, 1341-1352.
16. Evans, T.; Wickett, R. R. *Practical Modern Hair Science.* 2012.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. A method for treating hair, comprising:
   i) providing a hair sample comprising a plurality of disulfide bonds; and
   ii) applying to the hair sample for a period of time a mixture, comprising one or more thiol compounds; and a catalyst, thereby producing a covalently bonded hair sample, wherein the covalently bonded hair sample comprises a plurality of disulfide bonds between the hair sample and the thiol compounds, wherein at least one of the one or more thiol compounds is alpha lipoic acid.

2. The method of claim 1, further comprising applying a monomer to the covalently bonded hair sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the covalently bonded hair sample and the monomers.

3. The method of claim 1, wherein the concentration of the one or more thiol compounds in the mixture is about 0.05% by weight to about 60% by weight.

4. The method of claim 1, wherein the ratio by weight of the mixture to the hair sample is about 1:1 to about 100:1.

5. The method of claim 2, wherein the monomer is selected from the group consisting of an acrylate, a methacrylate, a monomer comprising a vinyl group, and a monomer comprising a maleimide group.

6. The method of claim 2, wherein the molar ratio of the monomer to the free thiol groups is about 100:1 to about 1:500.

7. The method of claim 1, wherein the catalyst is selected from the group consisting of an amine, a phosphine, and a radical initiator.

8. The method of claim 1, wherein the mixture further comprises an oxidizing agent.

9. The method of claim 1, wherein the method further comprises a post-treatment comprising applying to the covalently bonded hair sample for a period of time an additive, wherein the additive is selected from the group consisting of a fatty acid, a fatty alcohol, a fatty acid ester, an amino acid mixture, a peptide mixture, an acidifier, a polycarboxylic acid, an oxidizing agent, or a mixture thereof.

10. The method of claim 2, wherein the method further comprises a post-treatment comprising applying to the covalently bonded hair sample for a period of time an additive, wherein the additive is selected from the group consisting of a fatty acid, a fatty alcohol, a fatty acid ester, an amino acid mixture, a peptide mixture, an acidifier, a polycarboxylic acid, an oxidizing agent, or a mixture thereof.

11. The method of claim 1, wherein the one or more thiol compounds is alpha lipoic acid and ammonium thioglycolate.

12. The method of claim 1, wherein the concentration of the one or more thiol compounds in the mixture is about 5% by weight to about 10% by weight.

13. The method of claim 11, wherein the concentration of the one or more thiol compounds in the mixture is about 5% by weight to about 10% by weight.

\* \* \* \* \*